(12) United States Patent
Kruse et al.

(10) Patent No.: US 7,294,647 B2
(45) Date of Patent: *Nov. 13, 2007

(54) KAPPA AGONIST COMPOUNDS AND PHARMACEUTICAL FORMULATIONS THEREOF

(75) Inventors: Lawrence I. Kruse, Haddonfield, NJ (US); An-Chih Chang, Bensalem, PA (US); Diane L. DeHaven-Hudkins, Chester Springs, PA (US); John J. Farrar, Chester Springs, PA (US); Forrest Gaul, Douglassville, PA (US); Virendra Kumar, Paoli, PA (US); Michael Anthony Marella, Philadelphia, PA (US); Alan L. Maycock, Malvern, PA (US); Wei Yuan Zhang, Collegeville, PA (US)

(73) Assignee: Adolor Corporation, Exton, PA (US)

( * ) Notice: Subject to any disclaimer, the term of this patent is extended or adjusted under 35 U.S.C. 154(b) by 439 days.

This patent is subject to a terminal disclaimer.

(21) Appl. No.: 10/455,545

(22) Filed: Jun. 5, 2003

(65) Prior Publication Data

US 2003/0236248 A1 Dec. 25, 2003

Related U.S. Application Data

(60) Division of application No. 09/769,450, filed on Jan. 26, 2001, now abandoned, which is a continuation of application No. 09/436,057, filed on Nov. 8, 1999, now Pat. No. 6,180,623, which is a division of application No. 09/307,517, filed on May 7, 1999, now Pat. No. 6,028,063, which is a division of application No. 09/045,522, filed on Mar. 21, 1998, now Pat. No. 5,981,513, which is a division of application No. 08/891,833, filed on Jul. 14, 1997, now Pat. No. 5,763,445, which is a continuation-in-part of application No. 08/796,078, filed on Feb. 5, 1997, now Pat. No. 5,688,955, which is a continuation-in-part of application No. 08/612,680, filed on Mar. 8, 1996, now Pat. No. 5,646,151.

(51) Int. Cl.
*A01N 43/38* (2006.01)
*A01N 43/36* (2006.01)
*A01N 43/64* (2006.01)
*A61K 31/40* (2006.01)
*A61K 31/41* (2006.01)

(52) U.S. Cl. .................. 514/411; 514/359; 514/408; 514/410; 514/424

(58) Field of Classification Search ............. 514/422; 548/518; 546/284.1
See application file for complete search history.

(56) References Cited

U.S. PATENT DOCUMENTS 4,065,573 A 12/1977 Lednicer ............ 424/278

(Continued)

FOREIGN PATENT DOCUMENTS

EP 0 108 602 5/1984

(Continued)

OTHER PUBLICATIONS

EPO Communication dated Feb. 26, 2004 (EP 98 935 477.4).

(Continued)

*Primary Examiner*—Sreeni Padmanabhan
*Assistant Examiner*—Yong S. Chong
(74) *Attorney, Agent, or Firm*—Woodcock Washburn LLP

(57) ABSTRACT

Compounds having kappa opioid agonist activity, compositions containing them and 5 method of using them as analgesics and pruritic agents are provided.

The compounds of formulae I, II, III and IV have the structure:

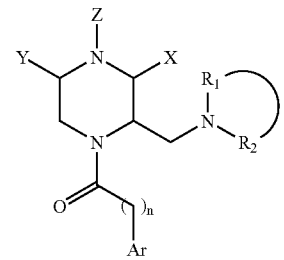

(I)

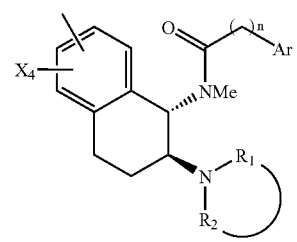

(II)

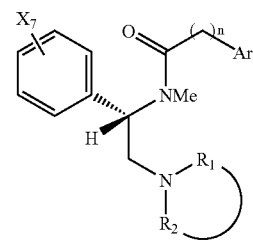

(III)

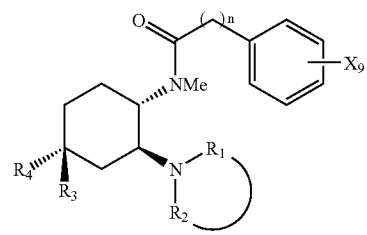

(IV)

wherein
$X, X_4, X_5, X_7, X_9$;
$R_1, R_2, R_3, R_4$; and
$Y, Z$ and $n$ are as described in the specification.

4 Claims, No Drawings

U.S. PATENT DOCUMENTS

| | | | |
|---|---|---|---|
| 4,098,904 A | 7/1978 | Szmuszkovicz | 424/324 |
| 4,145,435 A | 3/1979 | Szmuszkovicz | 424/274 |
| 4,212,878 A | 7/1980 | Lednicer et al. | 424/274 |
| 4,359,476 A | 11/1982 | Kaplan et al. | 424/274 |
| 4,360,531 A | 11/1982 | McMillan et al. | 424/274 |
| 4,438,130 A | 3/1984 | Kaplan | 424/274 |
| 4,463,013 A | 7/1984 | Collins et al. | 424/274 |
| 4,466,977 A | 8/1984 | McMillan et al. | 424/274 |
| 4,663,343 A | 5/1987 | Horwell et al. | 514/429 |
| 4,855,316 A | 8/1989 | Horwell et al. | 514/422 |
| 4,906,655 A | 3/1990 | Horwell et al. | 514/422 |
| 4,929,627 A | 5/1990 | Pennev et al. | 514/320 |
| 4,943,578 A | 7/1990 | Naylor et al. | 514/252 |
| 5,114,945 A | 5/1992 | Hayes et al. | 514/278 |
| 5,116,842 A | 5/1992 | Naylor et al. | 514/252 |
| 5,232,978 A | 8/1993 | Gottschlich et al. | 514/422 |
| 5,475,019 A | 12/1995 | Privette et al. | 514/408 |
| 5,532,266 A | 7/1996 | Gottschlich et al. | 514/428 |
| 5,610,271 A | 3/1997 | Dooley et al. | 530/328 |
| 5,646,151 A | 7/1997 | Kruse et al. | 514/255 |
| 5,688,955 A | 11/1997 | Kruse et al. | 546/276.4 |
| 5,744,458 A | 4/1998 | Kruse et al. | 514/91 |
| 5,760,023 A | 6/1998 | Farrar et al. | 514/150 |
| 5,763,445 A | 6/1998 | Kruse et al. | 514/255 |
| 5,804,595 A | 9/1998 | Portoghese et al. | 514/428 |
| 5,849,762 A | 12/1998 | Farrar et al. | 514/327 |
| 5,869,521 A | 2/1999 | Farrar et al. | 514/422 |
| 5,888,494 A | 3/1999 | Farrar et al. | 424/78.05 |
| 5,945,443 A | 8/1999 | Kruse et al. | 514/429 |
| 5,981,513 A | 11/1999 | Kruse et al. | 514/91 |
| 6,004,964 A | 12/1999 | Farrar et al. | 514/255 |
| 6,028,063 A | 2/2000 | Kruse et al. | 514/91 |
| 6,048,860 A | 4/2000 | Farrar et al. | 514/252 |
| 6,054,445 A | 4/2000 | Zhang et al. | 514/91 |
| 6,057,323 A | 5/2000 | Zhang et al. | 514/255 |
| 6,156,769 A | 12/2000 | Farrar et al. | 514/320 |
| 6,180,623 B1 | 1/2001 | Kruse et al. | 514/212.02 |
| 6,239,154 B1 | 5/2001 | Zhang et al. | 514/343 |
| 6,303,611 B1 | 10/2001 | Zhang et al. | 514/255 |

FOREIGN PATENT DOCUMENTS

| | | | |
|---|---|---|---|
| EP | 0 147 085 | | 12/1984 |
| EP | 0 207 773 | | 6/1986 |
| EP | 0 233 793 | | 1/1987 |
| EP | 0 254 545 | | 1/1988 |
| EP | 0 260 555 | | 3/1988 |
| EP | 0 261 842 | | 3/1988 |
| EP | 0 372 466 | | 6/1988 |
| EP | 0 329 563 | A | 2/1989 |
| EP | 0 330 461 | | 2/1989 |
| EP | 0 330 467 | | 2/1989 |
| EP | 0 325 406 | | 7/1989 |
| EP | 0 330 469 | | 8/1989 |
| EP | 0 343 900 | A | 8/1989 |
| EP | 0 333 427 | | 9/1989 |
| EP | 0 366 327 | | 10/1989 |
| EP | 0 374 054 | | 12/1989 |
| EP | 0 356 247 | | 2/1990 |
| EP | 0 393 696 | | 4/1990 |
| EP | 0 398 720 | | 11/1990 |
| EP | 0 409 489 | | 1/1991 |
| EP | 0 483 580 | | 10/1991 |
| EP | 0 569 802 | A | 5/1993 |
| EP | 0 577 847 | | 1/1994 |
| EP | 0 752 246 | | 1/1997 |
| WO | WO 90/07502 | | 7/1990 |
| WO | WO 92/20657 | | 11/1992 |
| WO | WO 94/18165 | | 8/1994 |
| WO | WO 95/03308 | | 2/1995 |
| WO | WO 96/06077 | | 2/1996 |
| WO | WO 96/06078 | | 2/1996 |
| WO | WO 97/20831 | | 6/1997 |
| WO | WO 97/32857 | | 9/1997 |
| WO | WO 98/23290 | | 6/1998 |
| WO | WO 99/03468 | | 1/1999 |
| WO | WO 99/03499 | | 1/1999 |
| WO | WO 00/14065 | | 3/2000 |

OTHER PUBLICATIONS

Raynor et al., "Pharmacological Characterization of the Cloned κ-, δ-, and μ-Opioid Receptors," *Molecular Pharmacol.*, 1994, 45, 330-334.

Wheeler-Aceto et al., "Standardization of the rat paw formalin test for the evaluation of analgesics," *Psychopharmacology*, 1991, 104, 35-44.

Ballantyne et al., "Itching After Epidural and Spinal Opiates," *Pain*, 1988, 33, 149-160.

Bernhard, J.D., "Itching in the Nineties," *J. Am. Acad. Derm.*, 1991, 24, 309-310.

Bernstein et al., "Antipruritic Effect of an Opiate Antagonist, Naloxone Hydrochloride," *Journal of Investigative Dermatology*, 1982, 78(2), 82-83.

McMahon et al., "Itching for an Explanation," *TINS*, 1992, 15(12), 497-501.

Thomas et al., "Microinjection of morphine into the rat medullary dorsal horn produces a dose-dependent increase in facial scratching," *Brain Research*, 1995, 695(2), 267-270.

Walter, M., "Neural Mechanisms of Itch Sensation," *LASP Newsletter*, Sep./Oct. 1996, 1-10.

Szmuszkovicz et al., "Benzeneacetamide Amines: Structurally Novel Non-mμ Opioids," *Journal of Medicinal Chemistry*, 1982, 25(10), 1125-6.

Change, et al., "Kappa opioid receptor selective affinity labels: Electrophilic benzeneaceatamides as kappa-selective opioid antagonist," *J. Med. Chem.*, 1994, 37, 4490-4498.

Freeman et al, "Naphto and Benzo Analogues of the κ Opioid Agonist trans-(±)-3,4-Dichloro-N-methyl-N-[2-(1-pyrrolidinyl)cyclohexyl]benzeneacetamide," *J. Med. Chem.*, 1991, 34(6), 1891-1896.

Lawhorn, et al., "Epidural morphine with butorphanol for postoperative analgesis after cesarean delivery," *Anesthesia and Analgesia*, 1991, 72(1), 53-57.

Magerl, W., "Neural Mechanisms of Itch Sensation," *IASP Newsletter*, Sep./Oct. 1996, 1-10.

Rajagopalan, P. et al., "DuP 747: Structure activity relationship study," *Bioorganic & Medicinal Chemistry Letters*, 1992, 2(7), 721-726.

Collins, et al., US 4,463,013, Jul. 31, 1984, *Chemical Abstracts*, Chemistry Abstract No. 101:204315; Chemical Abstract Registry No. 92953-42-9.

deCosta, B.R., et al., "Probes for narcotic receptor mediated phenomena as opioid receptor ligands," *J. Med. Chem.*, 1990, 33(4), 1171-1176, *Chemical* Abstracts, Chemical Abstract No. 112:138845; Chemical Abstract Registry Nos. 118243-29-1, 124942-79-6, 125072-90-4.

deCosta, B.R., et al., "Selective and enantiospecific acylation of kappa-opioid receptors by . . . ," *J. Med. Chem.*, 1989, 32(2), 281-283, *Chemical* Abstracts, Chemcial Abstract No. 110:75224; Chemical Abstract Registry 118243-29-1.

deCosta, B.R., "Synthesis of an affinity ligand ('UPHIT') for in vivo acylation of the κ-opioid receptor," *Elsevier Science Publishers B.V.*, Jun. 1989, XP-000940483, 249(2), 178-182.

Giardina, G., et al., "Central and peripheral analgesic agents: chemical strategies for limiting brain penetration in kappa-opioid agonists belonging to different chemical classes," Il Farmaco, 1995, 50(6), 405-418.

Hayward, N.J., et al., "The neuroprotective action of kappa-opioid agonists in the gerbil," *Mol. Neuropharmacol*, 1992, 2(3), 221-227, *Chemical* Abstracts, Chemical Abstract No. 117:245459; Chemical Abstract Registry No. 87173-94-2.

Kaplan, US 4,438,130 Mar. 20, 1984, *Chemical Abstracts*, Chemical Abstract No. 99:139741; Chemical Abstract Registry No. 87151-85-7.

Li, J.G., et al., "Comparative studies on the affinities of K-11 and U-50488H for kappa opiate receptor," *Yaoxue Wuebao*, 1991, 26(1), 10-14, *Chemical* Abstracts, Chemical Abstract No. 114:199538; Chemical Abstract Registry No. 106709-52-8.

Scopes, D.I.C., "Selective non-peptide kappa opioid recptor agonists," *Exp. Opin. Invest. Drugs*, 1994, 3(4), 369-376.

Szmuszkovicz, US 4,145,435, Mar. 20, 1979, Chemical Abstract No. 89:146631; Chemical Abstract Registry No. 67198-13-4.

Upjohn Co., EP 162690 A2, Nov. 27, 1985, *Chemical Abstracts*, Chemical Abstract No. 107:58832; Chemical Abstract Registry No. 109063-12-9.

Upjohn Co., EP 129991 A1, Jan. 2, 1985, *Chemical Abstracts*, Chemical Abstract No. 103:160382; Chemical Abstract Registry No. 67198-17-8.

Upjohn Co., EP 126612 A1, Nov. 28, 1984, *Chemical Abstracts*, Chemical Abstract No. 102:184969, Chemical Abstract Registry Nos. 95458-07-4, 95585-69-6.

Upjohn Co., EP 108601 A1, *Chemical Abstracts*, Chemical Abstract No. 102:24297, Chemical Abstract Registry No. 91873-43-7.

Weerawarna, S.A., et al., "Isothiocyanate-substituted κ-selective opioid receptor ligands derived from N-methyl-N[(1S)-1phenyl-2-(1-pyrrolidinyl)ethyl]phenylacetamide," *J. Med. Chem.*, 1994, XP-002148135, 37, 2856-2864.

KAPPA AGONIST COMPOUNDS AND PHARMACEUTICAL FORMULATIONS THEREOF

This application is a divisional of U.S. application Ser. No. 09/769,450, filed Jan. 26, 2001 now abandoned, which is a continuation of U.S. application Ser. No. 09/436,057, filed Nov. 8, 1999, now U.S. Pat. No. 6,180,623, which is a divisional of U.S. application Ser. No. 09/307,517, filed May 7, 1999, now U.S. Pat. No. 6,028,063, which is a divisional of U.S. application Ser. No. 09/045,522, filed Mar. 21, 1998, now U.S. Pat. No. 5,981,513, which is a divisional of U.S. application Ser. No. 08/891,833, filed Jul. 14, 1997, now U.S. Pat. No. 5,763,445, which is a continuation-in-part of U.S. application Ser. No. 08/796,078, filed Feb. 5, 1997, now U.S. Pat. No. 5,688,955, which is a continuation-in-part of U.S. application Ser. No. 08/612,680, filed Mar. 8, 1996, now U.S. Pat. No. 5,646,151.

BACKGROUND OF THE INVENTION

1. Field of the Invention

This invention relates to compounds, to processes of their preparation, to pharmaceutical compositions containing them and to their medical use as agonists at kappa opioid receptors.

The present invention also relates to compositions and method for the treatment and/or prevention of itch, also known as pruritus, which has many causes. The compositions, which are formulated for topical and systemic administration, contain kappa opiate receptor agonists that are substantially devoid of central nervous system effects, and, thus, have very little, if any potential for producing side effects associated with centrally acting kappa opiate receptor agonists.

2. Reported Developments

A) Kappa (κ)-Receptor Agonists as Analgesics

Opium and its derivatives are potent analgesics that also have other pharmacological effects, and exert their effects by interacting with high-affinity receptors.

It has been shown by investigators that there are at least three major opioid receptor types in the central nervous system (hereinafter CNS) and in the periphery. These receptors, known as mu (μ), delta (δ) and kappa (κ), have distinct pharmacological profiles, anatomical distributions and functions. [See, for example: Wood, P. L., *Neuropharmacology*, 21, 487-497, 1982; Simon, E., *J. Med. Res. Rev.*, 11, 357-374, 1991; Lutz et al., *J. Recept. Res.* 12, 267-286; and Mansour et. al., *Opioid I*, ed. Herz, A. (Springer, Berlin) pp. 79-106, 1993.] The δ receptors are abundant in CNS and mediate analgesia, gastrointestinal motility and various hormonal functions. The μ receptors bind morphine-like drugs and mediate the opiate phenomena associated with morphine, including analgesia, opiate dependence, cardiovascular and respiratory functions, and several neuroendocrine effects.

The κ receptors have a wide distribution in CNS and mediate a spectrum of functions including the modulation of drinking, water balance, food intake, gut motility, temperature control and various endocrine functions. They also produce analgesia. [See, for example: Leander et al., *J. Pharmacol. Exp. Ther.* 234, 463-469, 1985; Morley et al, *Peptides* 4, 797-800, 1983; Manzanares et al., *Neuroendocrinology* 52, 200-205, 1990; and Iyengar et al., *J. Pharmacol, Exp. Ther.*, 238, 429-436, 1986.]

Most clinically used opioid analgesics such as morphine and codeine act as μ receptor agonists. These opioids have well-known, undesirable and potentially dangerous dependence forming side effects. Compounds which are κ-receptor agonists act as analgesics through interaction with κ opioid receptors. The advantage of these agonists over the classical μ receptor agonists, such as morphine, lies in their ability to cause analgesia while being devoid of morphine-like behavioral effects and addiction liability.

A large number of classes of compounds which act as agonists at κ opioid receptors have been described in the art including the following illustrative classes of compounds.

U.S. Pat. No. 4,065,573 discloses 4-amino-4-phenylcyclohexane ketal compounds having analgesic activity.

U.S. Pat. No. 4,212,878 discloses phenylacetamide derivatives having analgesic properties and reduced physical dependence liability properties, relative to morphine and methadone.

U.S. Pat. No. 4,145,435 discloses N-(2-amino-cycloaliphatic)-phenylacetamide compounds having analgesic activity and narcotic antagonist activity.

U.S. Pat. No. 4,098,904 discloses N-(2-amino-cycloaliphatic)-benzoamides and naphthamides useful for relieving pain.

U.S. Pat. No. 4,359,476 discloses substituted cycloalkane-amides useful as analgesics and having low abuse liability.

U.S. Pat. No. 4,438,130 discloses 1-oxa-, aza- and thia-spirocyclic compounds having analgesic activity, low physical dependence and abuse liability properties and little dysphoric inducing properties.

U.S. Pat. No. 4,663,343 discloses substituted naphthalenyloxy-1,2-diaminocyclohexyl amides as analgesics.

U.S. Pat. No. 4,906,655 discloses 1,2-cyclohexylaminoaryl amides having high kappa-opioid affinity, selectivity and potency and useful as analgesics, diuretics, anti-inflammatory and psychotherapeutic agents.

B) Kappa (κ)-receptor Agonists as Anti-Pruritic Agents

The prior art has investigated the physiology and treatment of pruritus as illustrated hereunder.

Itch is a well known sensory state associated with the desire to scratch. As with pain, itch can be produced by a variety of chemical, mechanical, thermal or electrical stimuli. In addition to the difference in the sensory quality of itch and pain, they also differ in that (1) itch, unlike pain, can only be evoked from the superficial layers of skin, mucosa, and conjunctiva, and (2) itch and pain usually do not occur simultaneously from the same skin region; in fact, mildly painful stimuli, such as scratching, are effective in eliminating itch. In addition, the application of histamine to skin produces itch but not pain. Itch and pain are further dissociated pharmacologically: itch appears to be insensitive to opiate and non-steroidal anti-inflammatory drug (NSAID) treatment, both of which are effective in treating pain.

Although itch and pain are of a class in that both are modalities of nociception transmitted by small unmyelinated C fibers, evidence that itch is not just a variety of low-threshold pain is overwhelming. Itch leads to the reflex or urge to scratch; pain leads to withdrawal. Itch occurs only in the skin; pain arises from deeper structures as well. Heat may stop pain but usually increases pain. Removal of the epidermis eliminates itch but causes pain. Analgesics, particularly opioids, relieve pain but often cause itch (see, for example *J. Am. Acad. Derm.* 24: 309-310, 1991). There can be no doubt that itching is of eminent clinical importance; many systemic and skin diseases are accompanied by persistent or recurrent itch attacks. Current knowledge suggests that itch has several features in common with pain but exhibits intriguing differences as well (see, for example, W. Magerl, *IASP Newsletter*, pp. 4-7, September/October 1996).

McMahon et al. (*TINS*, Vol. 15, No. 12, pp. 497-501, 1992) provides a description of stimuli (Table a) and a comparison of the established features of itch and pain (Table b):

TABLE a

Stimuli that can elicit or augment itch

Physical

Mechanical. Light touch, pressure, suction.
Thermal. Warming.
Electrical. Focal transcutaneous repetitive stimulation,
transcutaneous constant current stimulation,
intraneural microstimulation.

Chemical

Non-specific irritants. Acids, alkalis.
Inflammatory mediators. Histamine, kallikrein,
bradykinin, prostaglandins.
Histamine-releasing substances. Compound 48/80, protamine, C3a.
Peptidases. Mucunain, papain, trypsin, mast cell chymase.
Neuropeptides. Substance P, vasoactive intestinal polypeptide,
neurotensin, secretin.
Opioids. Morphine, β-endorphin, enkephalin analogues.

TABLE b

Comparison of the established features of itch and pain

| | ITCH | PAIN |
|---|---|---|
| Psychophysiology | | |
| Tissue | Skin. Mucous membranes | Most tissues |
| Stimulus | See Table a | Many stimuli |
| Intraneural microstimulation | Occasionally | Yes |
| Secondary sensations | Alloknesis (itchy skin) | Hyperalgesia |
| Psychogenic modification | Pronounced | Present |
| Counterstimuli | Scratching, pain, cooling | Tactile stimuli, cooling |
| Neurophysiology | | |
| Primary afferent neurones | C- and Aδ-fibres | C- and Aδ-fibres |
| Flare size | Large | Small |
| Spinal pathway | Anterolateral funiculus | Anterolateral funiculus |
| Protective reflexes | Scratching, sneezing | Flexion, guarding |
| Autonomic reflexes | Yes | Yes |
| Pharmacology | | |
| Capsaicin sensitivity | Yes | Chemogenic pain; yes |
| NSAID sensitivity | Probably not | Yes |
| Morphine sensitivity | No | Yes |

Abbreviations:
NSAID, non-steroidal anti-inflammatory drugs.

Experimental focal itch stimuli are surrounded by a halo of seemingly unaffected tissue where light tactile stimuli are capable of eliciting itch-like sensations. The term itchy skin or alloknesis has been coined for these secondary sensations that are reminiscent of the features of secondary hyperalgesia evolving around a painful focus. A crucial observation is that itch and pain usually do not coexist in the same skin region and a mild noxious stimulus such as scratching is in fact the singly most effective way to abolish itch. This abolition of itch can be prolonged producing an 'antipruritic state'. Although mild scratch is often not painful, microneurographic recordings from humans have directly determined that such stimuli are among the most effective ways to excite cutaneous unmyelinated nociceptive afferents. (See, for example:

Shelly, W. B. and Arthur, R. P. (1957) *Arch. Dermatol.* 76. 296-323;
Simone, D. A. et al. (1987) *Somatosens. Res.* 5, 8 1-92;
Graham, D. T., Goodell, H. and Wolff, H. G. (1951) *J. Clin. Invest.* 30, 37-49;
Simone, D. A., Aireja, M. and LaMotte, R. H. (1991) *Somatosens Mot. Res.* 8, 27 1-279;
Torebjörk, E (1985) *Philos. Trans. R. Soc. London Ser.* B 308, 227-234; and
Vailbo, A. B., Hagbarth, K. E., Torebjörk, H. E. and Wallin, B. G. (1979) *Physiol. Rev.* 59,919-957).

Physiologically, there is evidence that substance P released from nociceptor terminals can cause the release of histamine from mast cells. Activation of mast cells, with release of the pruritogen histamine, occurs in immediate type hypersensitivity diseases, such as anaphylactic reactions and urticaria. Urticarial eruptions are distinctly pruritic and can involve any portion of the body, and have a variety of causes beyond hypersensitivity, including physical stimuli such as cold, solar radiation, exercise and mechanical irritation. Other causes of pruritus include: chiggers, the larval form of which secretes substance that creates a red papule that itches intensely; secondary hyperparathyroidism associated with chronic renal failure; cutaneous larva migrans, caused by burrowing larvae of animal hookworms; dermal myiasis, caused by maggots of the horse botfly, which can afflict horseback riders; onchocerciasis ("river blindness") caused by filarial nematodes; pediculosis, caused by lice infestations; enterobiasis (pinworm) infestations, which afflict about 40 million Americans, particularly school children; schistosome dermatitis (swimmer's itch); and asteatotic eczema ("winter itch"). The role of histamine or other endogenous pruritogens in mediating itch associated with these and other pruritic conditions, such as atopic dermatitis, it is not yet well established. For atopic dermatitis, in particular, it appears that itch is not inhibited by antthistamines, but by cyclosporin A, a drug which inhibits the production of cytokines which have been proposed as potential pruritogens.

Current therapies for the treatment of itch include a variety of topical and systemic agents, such as steroids, antihistamines, and some psychotherapeutic tricyclic compounds, such as doxepin hydrochloride. Many such agents are listed in *PDR Generics* (see Second Edition, 1996, p. cv for a listing of said agents). The limitations of these agents are well known to medical practitioners, and are summarized in the 'Warnings" and "Precautions" sections for the individual agents listed in *PDR Generics*. In particular, the lack of complete efficacy of antihistamines is well known, but antihistamines are frequently used in dermatology to treat pruritus due to urticaria, atopic dermatitis, contact dermatitis, psoriasis, and a variety of other conditions. Although sedation has been a frequent side effect of conventional systemically administered antihistamines, a new generation of antihistamines have been developed that are nonsedating, apparently due to their inability to cross the blood-brain barrier.

Intravenous administration of opiate analgesics, such as morphine and hydromorphone has been associated with pruritus, urticaria, other skin rashes, wheal and flare over the vein being injected. These itch and itch-related reactions are believed to be due to a histamine-releasing property of these opiates, via mast cell degranulation. These opiates are thought to act upon the mu subtype of opiate receptor, but the possibility of interactions at the other principal opiate receptor subtypes (delta and kappa) cannot be excluded since these and other pruritogenic analgesics are not pure mu agonists. The cellular loci of the receptor type(s) mediating the itching effect is not known, although the mast cell is a possible candidate since opiates cause histamine release from these cells. However, some investigators have suggested that the frequent inability of antihistamines to block morphine-induced itching suggests a non-histaminergic mediation of opiate-induced itching—a mechanism which could involve central opiate receptors. Although i.v. morphine only occasionally results in generalized itching (in about 1% of patients), pruritus is more prevalent in opiate analgesia with epidural (8.5%) or intraspinal (45.8%) administration. (See, for example: Bernstein et al., "Antipruritic Effect of an Opiate Antagonist, Naloxone Hydrochloride", *The Journal of Investigative Dermatology,* 78:82-83, 1982; and Ballantyne et al., "Itching after epidural and spinal opiates", *Pain,* 33: 149-160, 1988.)

To date, treatment with opiates has not only proven useless in the treatment of itch, but appears to exacerbate itch in man. The consistent findings from human studies indicate that whether by central or peripheral mechanisms, opiates appear to promote rather than prevent itching, and that opiate antagonists have anti-pruritic activity.

Human clinical studies have generally shown that opiates cause itching and there is evidence that these effects can be reproduced in animal models, where itching sensations per se cannot be reported, but scratching behavior can be observed. (See, for example: Thomas et al., "Microinjection of morphine into the rat medullary dorsal horn produces a dose-dependent increase in facial-scratching", *Brain Research,* 195: 267-270, 1996; Thomas et al., "Effects of central administration of opioids on facial scratching in monkeys", *Brain Res.,* 585: 315-3 17, 1992; and Thomas et al., "The medullary dorsal horn: A site of action of opioids in producing facial scratching in monkeys", *Anesthesiology,* 79: 548-554, 1993).

We have now surprisingly discovered that kappa agonist compounds, which are substantially devoid of central nervous system effects, in pharmaceutically acceptable vehicles for systemic and topical formulations possess anti-pruritic activity in addition to anti-hyperalgesic activity.

SUMMARY OF THE INVENTION

Compounds having kappa opioid agonist activity, compositions containing them and method of using them as analgesics are provided. The present invention further provides compositions comprising compounds having kappa opioid agonist activity for the prevention and treatment of pruritus.

In its compound aspect, the present invention provides a compound of the formulae I, II, III and IV, or a pharmaceutically acceptable salt thereof.

The compounds of formula (I) have the following structure:

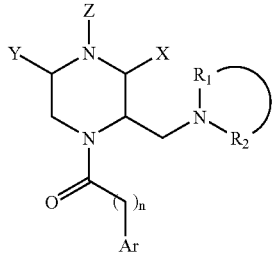

wherein n=1-3, where n=1 is preferred $R_1$ and $R_2$ are independently =CH; —$(CH_2)_m$, where m=4-8, m=4 is most preferred; —$CH_2CH(OH)(CH_2)_2$—;

$CH_2CH(F)(CH_2)_2$—; —$(CH_2)_2O(CH_2)_2$—; or —$(CH_2)_2CH=CHCH_2$—;

Ar=unsubstituted or mono- or di-substituted phenyl wherein said substituents are selected from the group consisting of halogen, $OCH_3$, $SO_2CH_3$, $CF_3$, amino, alkyl, and 3,4-dichloro; benzothiophenyl; benzofuranyl; naphthyl; diphenyl methyl; or 9-fluorene;

Z is

—P(O)(OBn)$_2$; —P(O)(OH)$_2$; —$(CH_2)_pC(O)NHOH$; —$(CH_2)_pCO_2H$; —$SO_2CH_3$—$SO_2NH_2$;

—$CO(CH_2)_pCH(NH_2)(CO_2H)$; —$COCH(NH_2)(CH_2)_pCO_2H$; —$CO_2CH_3$; —$CONH_2$;

—$(CH_2)_pO(CH_2)_pCO_2H$; —$(CH_2)_pO(CH_2)_pCONHOH$; —$(CH_2)_pSO_2CH_3$;

—$(CH_2)_pNHC(S)NHCH(CO_2H)(CH_2)_pCO_2H$; —$(CH_2)_pSO_3H$; or

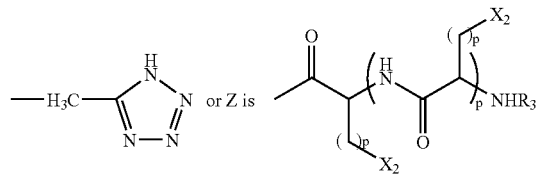

wherein p=0-20;

$R_3$=—H or —Ac $X_2$=—CO2H; —$NHSO_2CH_3$; $NHP(O)(OH)_2$; —$OP(O)(OBn)_2$; or $OP(O)(OH)_2$;

X and Y and independently

—$CH_2NHSO_2CH_3$; —$CH_2NHP(O)(OBn)_2$, —$CH_2NHP(O)(OH)_2$, —$CH_2OP(O)(OBn)_2$

—$CH_2OP(O)(OH)_2$; —$(CH_2)_qO(CH_2)_qCO_2H$; —$(CH_2)_qO(CH_2)_qSO_3H$;

—$(CH_2)_qO(CH_2)_qCHNHOH$;

—$CH_2NHC(S)NHCH(CO_2H)(CH_2)_qCO_2H$ or

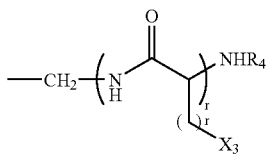

wherein
r=1-20
$R_4$=—H or —Ac
$X_3$=$CO_2H$; —$NHSO_2CH_3$; —NHP(O)(OBn)s; —NHP(O)(OH)$_2$; —OP(O)(OBn)$_2$ or —OP(O)(OH)$_2$ The compounds of formula II have the following structure:

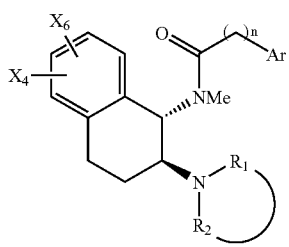

wherein
n=1-3, where n=1 is preferred
$R_1$ and $R_2$ are independently =$CH_3$; —$(CH_2)_m$, where m=4-8, m=4 is more preferred; —$(CH_2)_2O(CH_2)_2$—; $CH_2CH(F)(CH_2)_2$—; —$(CH_2)_2O(CH_2)_2$—; or —$(CH_2)_2CH$=$CHCH_2$—;
Ar=unsubstituted or mono- or di-substituted phenyl wherein said substituents are selected from the group consisting of halogen, $OCH_3$, $SO_2CH_3$, $CF_3$, amino, alkyl, and 3,4-dichloro; benzothiophenyl; benzofuranyl; naphthyl; diphenyl methyl; or 9-fluorene;

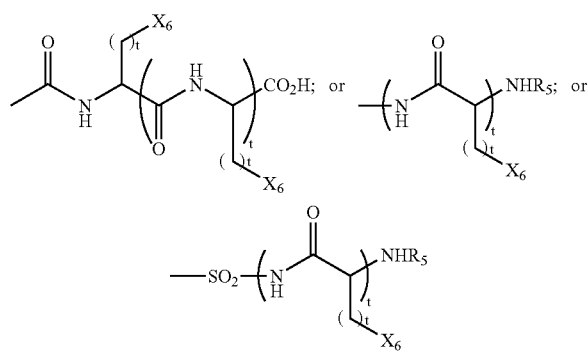

wherein
t=1-20
R5=—H or —Ac
X6=—$CO_2H$; —$NHSO_2CH_3$; —NHP(O)(OBn)$_2$; —NHP(O)(OH)2; —OP(O)(OBn)2; or —OP(O)(OH)2;

The compounds of formula HI have the following structure:

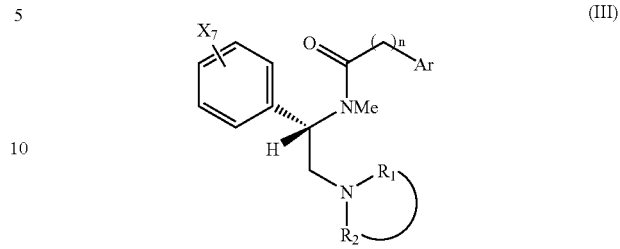

wherein
n=1-3, where n=1 is preferred
$R_1$ and $R_2$ are independently =$CH_3$; —$(CH_2)_m$, where m=4-8, m=4 is most preferred; —$CH_2CH(OH)(CH_2)_2$—; $CH_2CH_2(F)(CH_2)_2$—; $(CH_2)_2O(CH_2)_2$—; or —$(CH_2)_2CH$=$CHCH_2$—;
Ar=unsubstituted or mono- or di-substituted phenyl wherein said substituents are selected from the group consisting of halogen, $OCH_3$, $SO_2CH_3$, $CF_3$, amino, alkyl, and 3,4-dichloro; benzothiophenyl; benzofuranyl; naphthyl; diphenyl methyl; or 9-fluorene;
$X_7$ is $NHSO_2CH_3$; —NHP(O)(OBn)$_2$; —NHP(O)(OH)$_2$; —$(CH)_2NHSO_2CH_3$; —$(CH_2)_uNHC(S)NHCH(CO_2H)(CH_2)uCO_2H$; —CONHOH; or $(CH_2)_uCONHOH$:
wherein
u=1-5
or $X_7$ is

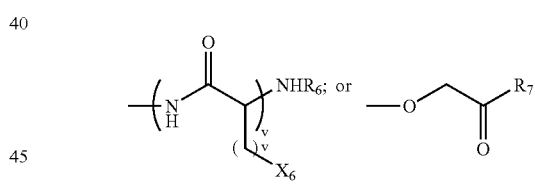

$R_6$=—H or —Ac
$X_6$=—$CO_2H$; —$NHSO_2CH_3$; —NHP(O)(OBn)$_2$ —NHP(O)(OH)$_2$; —OP(O)(OBn)$_2$; or —OP(O)(OH)$_2$
$R_7$=—$NH(CH_2)vCO_2H$; —$NH(CH_2)_vCH(NH_2)(CO_2H)$; —$NHCH(CO_2H)(CH_2)_vNH_2$; —$NH(CH_2)_vSO_3H$; —$NH(CH_2)_vPO_3H_2$; —$NH(CH_2)_vNHC(NH)NH_2$; or —$NHCH(CO_2H)(CH_2)_vCO_2H$; and
v=1-20

The compounds of formula IV have the following structure:

wherein:
t=120
$R_5$=—H or —Ac
$X_6$=$CO_2H$; —$NHSO_2CH_3$; —NHP(O)(OBn)$_2$; —NHP(O)(OH)$_2$; —OP(O)(OBn)$_2$ or —OP(O)(OH)$_2$.

DETAILED DESCRIPTION OF THE INVENTION

Peripherally-acting κ agonists can be prepared by the attachment of polar groups to non-peptide κ opioid receptor selective agonists, such as the arylacetamides. In designing the peripherally-acting ligands, the introduction of the polar groups may result in either retention or enhancement of antinociceptive potency and selectivity and also may increase the polarity of the ligand sufficient to reduce or eliminate CNS penetration across the blood-brain barrier (BBB). Thus, the identify and the positioning of the polar group(s) are important.

Using the prototypic arylacetamide, U50,488, as an example, the arylacetamide pharmacophore can be divided into three regions: the aromatic region, the central region, and the amine region. All three regions represent potential positions for the attachment of polar groups.

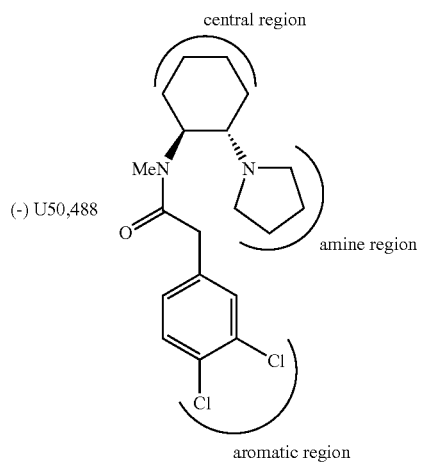

Compounds of formula (I) of the present invention are made as follows:

A series of novel compounds were made based on the class of arylacetamides reported by Glaxo (J. Med. Chem. 1993, 36, 2075). Specifically, compound 1 can be deprotected to yield intermediate 2, which can be derivatized by the attachment of a variety of polar groups (Scheme 1).

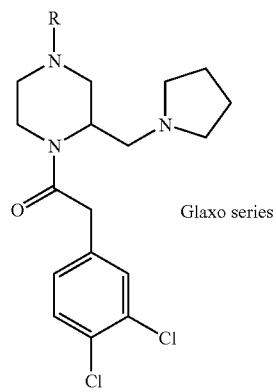

Glaxo series

The 3'-substituted series can be prepared via Scheme 2. The reduction of the Schiff base intermediate formed during the cyclization to 6 is expected to be stereoselective due to the directing effect of the neighboring hydroxymethyl group. Both intermediates 11 and 12 can be derivatized to confer peripheral selectivity.

The 5'-substituted series can be prepared via Schemes 3 and 4. Starting from N-t-Boc-O-MEM-D-serine, the 5'-(S) series can be prepared, and starting from N-t-Boc-O-MEM-L-serine allows the preparation of the 5'-(R) series.

Scheme 1

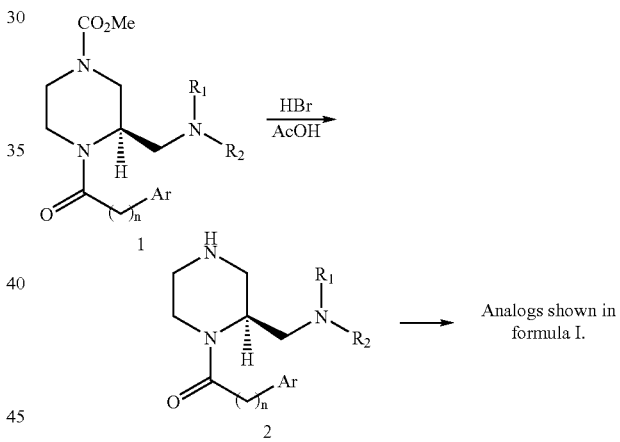

wherein Ar, $R_1$, $R_2$, and n are defined in formula I.

Scheme 2.

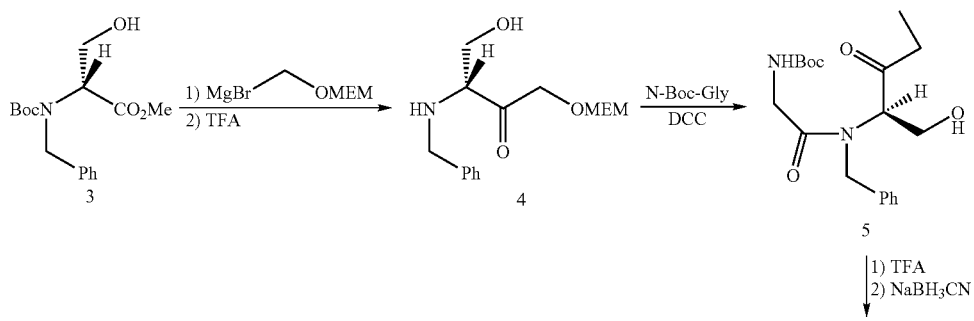

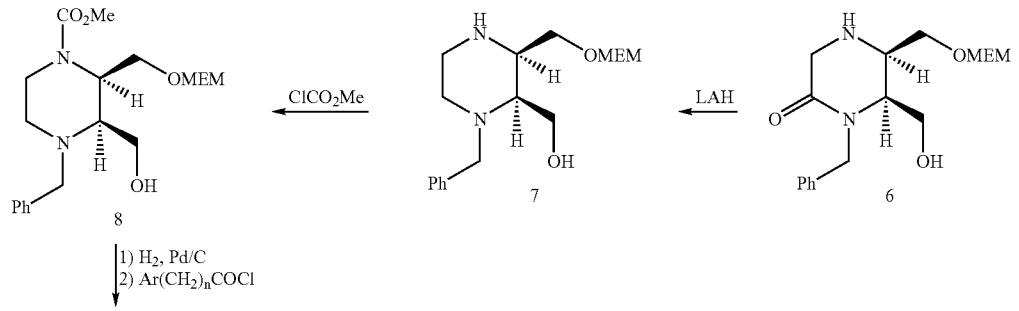
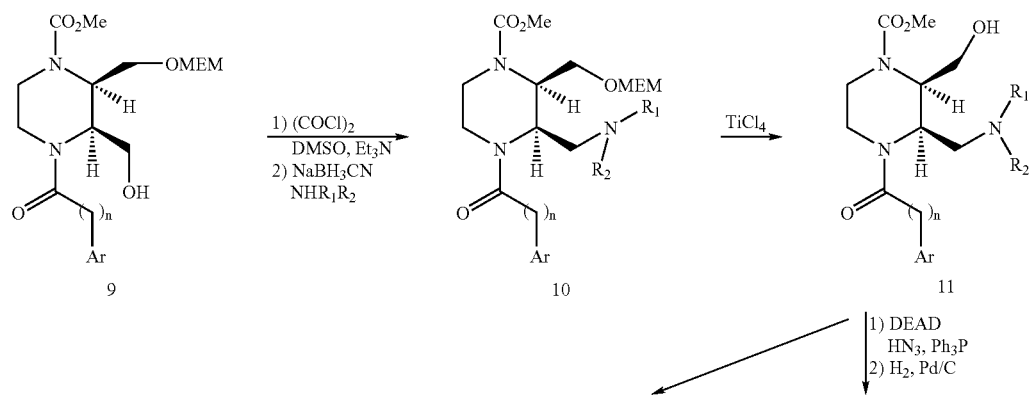
wherein Ar, $R_1$, $R_2$, and n are as defined in formula I.
Scheme 3.
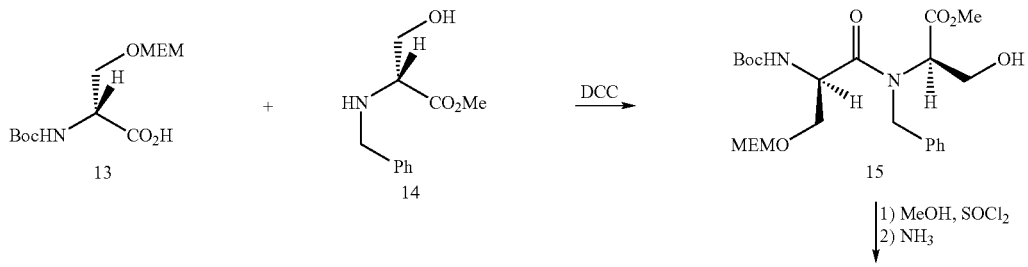

-continued
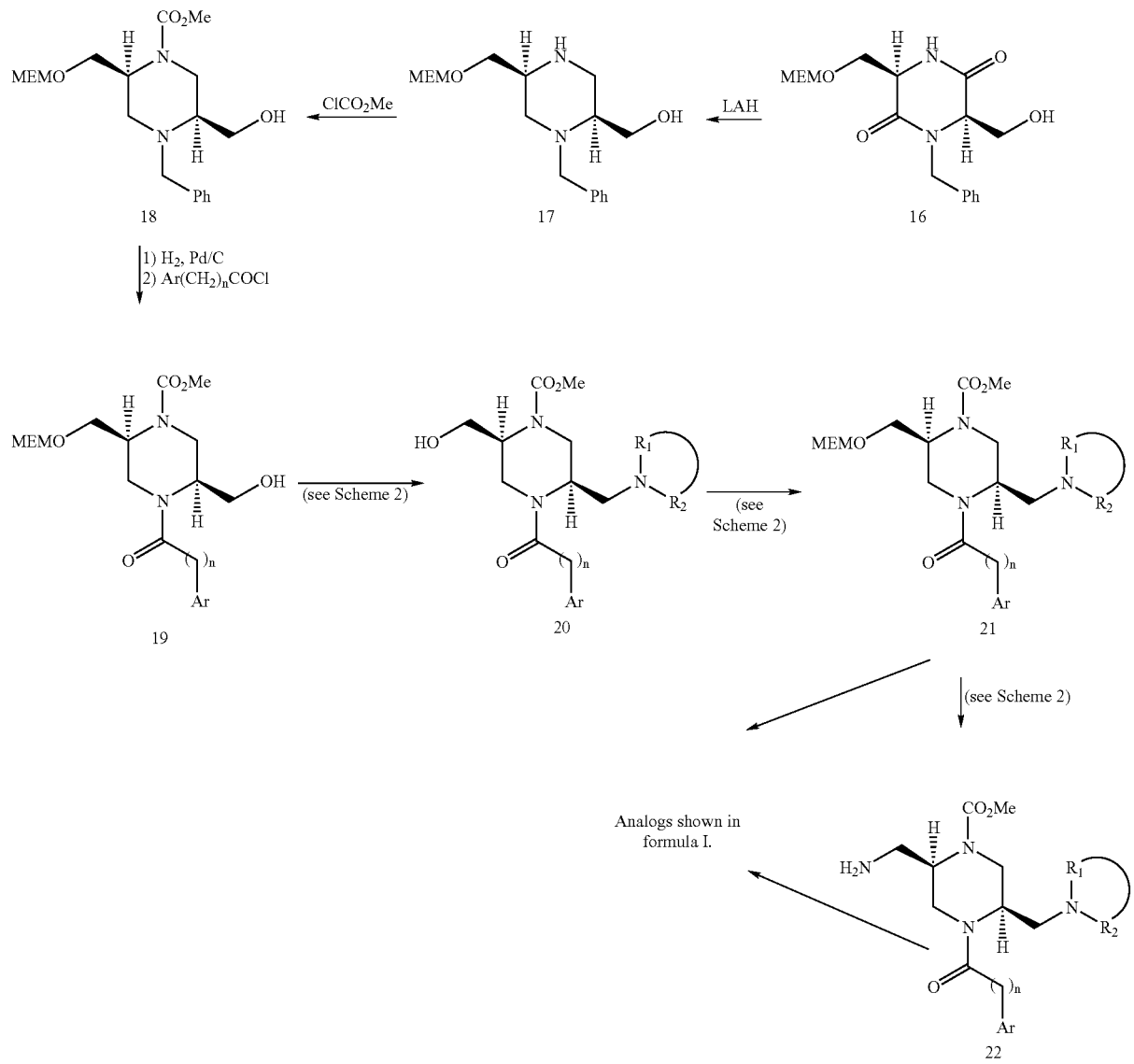
wherein Ar, $R_1$, $R_2$, and n are as defined in formula I.
Scheme 4
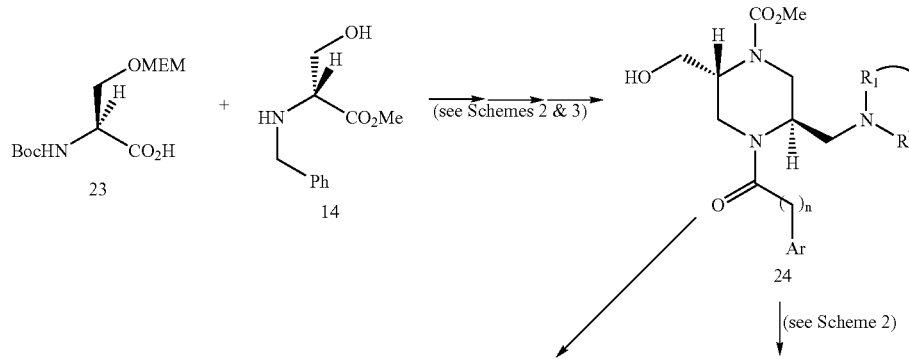

-continued
Analogs shown in formula I.

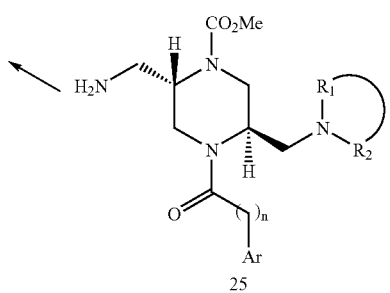

25 wherein Ar, $R_1$, $R_2$, and n are as defined in formula I.

Using Schemes 1-4 the following example compounds are made.

Intermediate 3 can be treated with t-butyl bromoacetate and deprotected to produce {4-[ 1-(3,4-Dichlorophenyl) acetyl-2R-(1-pyrrolidinyl)-methyl]piperazinyl } acetic acid (26).

Intermediate 3 can be reacted with methane sulfonyl chloride to produce [1-(3,4-Dichlorophenyl)acetyl-4-methanesulfonyl-2R-(1-pyrrolidinyl)methyl]piperazine (27).

Intermediate 3 can be coupled to N-t-Boc-L-asparticacid-β-benzyl ester and deprotected to produce [4-S-Aspartic acid-α-amido-1-(3,4-dichlorophenyl)acetyl-2R-(1-pyrrolidinyl)methyl]piperazine (28).

Intermediate 11 can be treated with t-butyl bromoacetate and deprotected to produce Methyl-[2R-(O-2-acetic acid)hydroxymethyl-4-(3,4-dichlorophenyl)acetyl-3R-(1-pyrrolidinyl)methyl]-1-piperazinecarboxylate (29).

Intermediate 11 can be coupled to N-t-Boc-L-aspartic acid-β-benzyl ester and deprotected to produce Methyl-[2R-(O-S-aspartic acid-α-acetyl)hydroxymethyl-4-(3,4-dichlorophenyl)acetyl-3R-(1-pyrrolidinyl)methyl]-1-piperazinecarboxylate (30).

Intermediate 12 can be treated with methanesulfonyl chloride to produce Methyl-[4-(3,4-dichlorophenyl)acetyl-2R-(N-methanesulfonamido)aminomethyl-3R-(1-pyrrolidinyl)methyl]-1-piperazinecarboxylate (31).

Intermediate 12 can be coupled to 2S-isothiocyanato-succinic acid-dibenzyl ester and deprotected to yield Methyl-{4-[3,4-dichlorophenyl]acetyl-3R-[1-pyrrolidinyl]methyl-2R-[N-(succinic acid-2S-thioureido)]aminomethyl)-1-piperazinecarboxylate (32).

Intermediate 21 can be treated with t-butyl bromoacetate and deprotected to produce Methyl-[2S-(O-2-acetic acid)hydroxymethyl-4-(3,4-dichlorophenyl)acetyl-5R-(1-pyrrolidinyl)methyl}-1-piperazinecarboxylate (33).

Intermediate 21 can be coupled to to N-t-Boc-L-aspartic acid-β-benzyl ester and deprotected to produce Methyl-[2S-(O-S-aspartic acid-α-acetyl)hydroxymethyl-4-(3,4-dichlorophenyl)acetyl-5R-(1-pyrrolidinyl)methyl]-1-piperazinecarboxylate (34).

Intermediate 22 can be treated with methanesulfonyl chloride to produce Methyl-[4-(3,4-dichlorophenyl)acetyl-2S-(N-methanesulfonamido)aminomethyl-5R-(1-pyrrolidinyl)methyl]-1-piperazinecarboxylate (35).

Intermediate 22 can be coupled to 2S-isothiocyanato-succinic acid-dibenzyl ester and deprotected to yield Methyl-{4-[3,4-dichlorophenyl]acetyl-5R-[1-pyrrolidinyl]methyl-2S-[N-(succinic acid-2S-thioureido)]aminomethyl } -1-piperazinecarboxylate (36).

The 2R isomers of 33-34 and 35-36 can be prepared from intermediates 24 and 25, respectively to produce Methyl-[2R-(O-2-acetic acid)hydroxymethyl-4-(3,4-dichlorophenyl)acetyl-5R-(1-pyrrolidinyl)methyl]-1-piperazinecarboxylate (37).

Methyl-[2R-(O-S-aspartic acid-α-acetyl)hydroxymethyl-4-(3,4-dichlorophenyl)acetyl-5R-(1-pyrrolidinyl)methyl]-1-piperazinecarboxylate (38).

Methyl-[4-(3,4-dichlorophenyl)acetyl-2R-(N-methanesulfonamido)aminomethyl-5R-(1-pyrrolidinyl)methyl]-1-piperazinecarboxylate (39).

Methyl-{4-[3,4-dichlorophenyl}acetyl-5R-[1-pyrrolidinyl]methyl-2R-[N-(succinic acid-2S-thioureido)]aminomethyl)-1-piperazinecarboxylate (40).

The corresponding structural formulas are shown hereunder.

FIG. 2

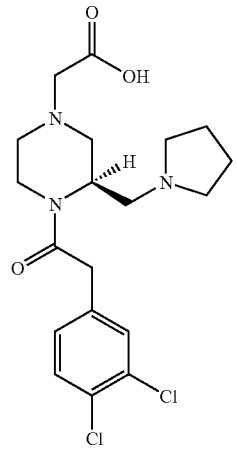

26

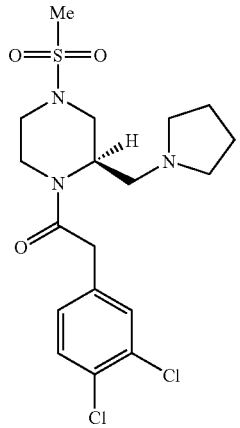

27

-continued
28
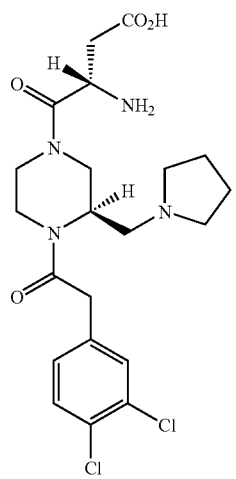
31
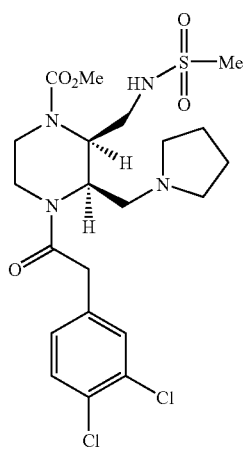
29
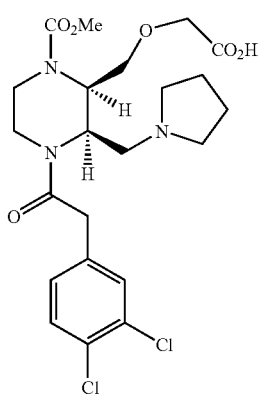
32
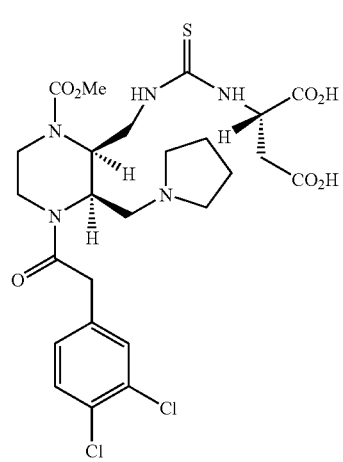
30
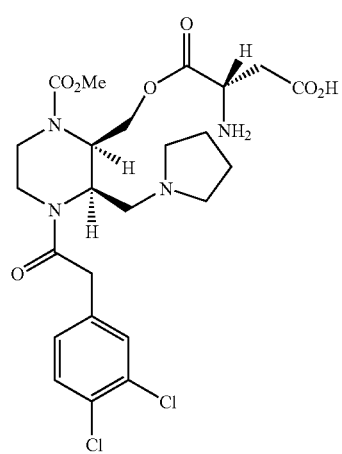
33
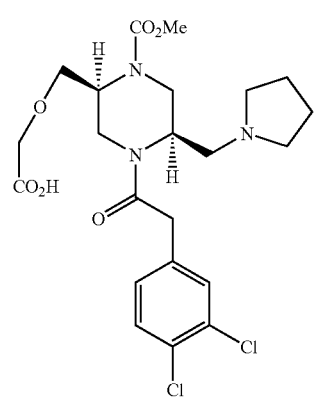

34
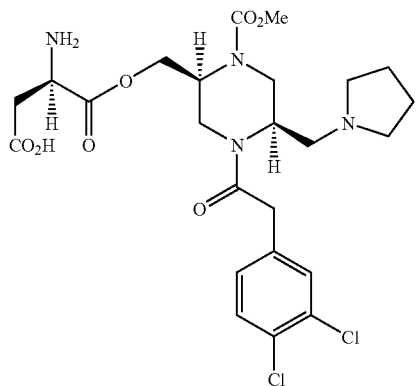
35
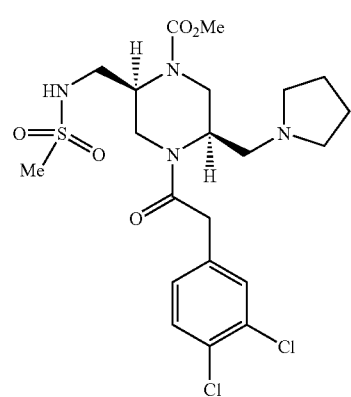
36
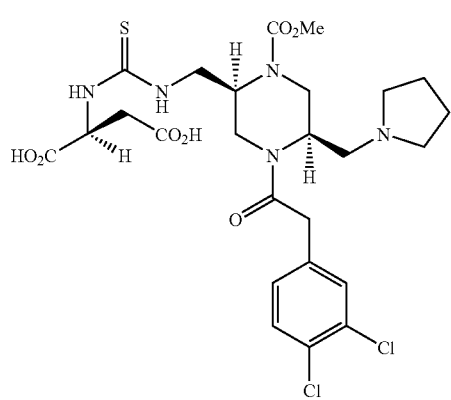
37
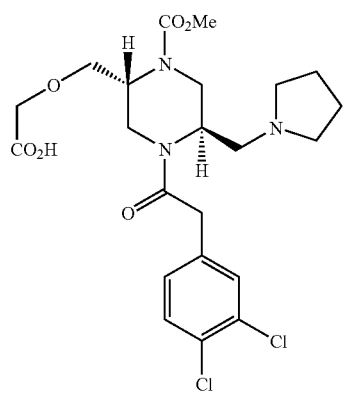
38
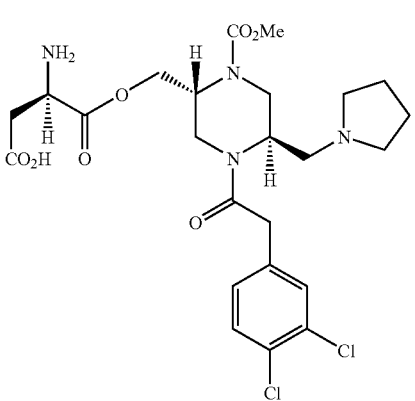
39
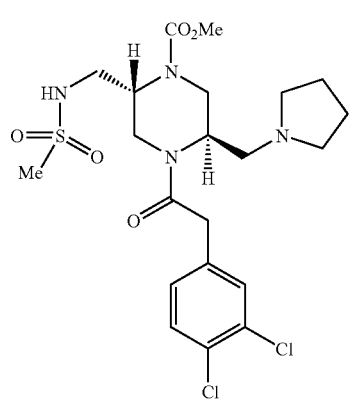

-continued

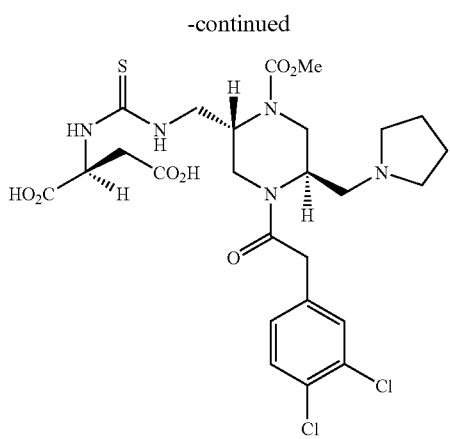
40

Compounds of formula II of the present invention are made by peripheralization by substitutions of the benzo portion of the tetrahydronaphthyl ring of the DuPont series of compounds with polar groups.

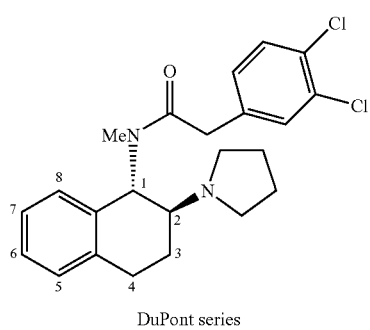

DuPont series

Starting material or precursors of the starting material are commercially available and thus allows regiospecific substitutions of the tetrahydronaphthyl ring (Scheme 5). While 5-hydroxytetralone, 6-hydroxytetralone, 7-hydroxytetralone, and 7-aminotetralone derivatives are readily available, 5-aminotetralone could be prepared from 5-hydroxytetralone (J. Org. Chem. 1972, 37, 3570).

The tetralone derivatives can be converted to dihydronaphthyl derivatives and subjected to chemistry similar to that employed in the preparation of U50,488 derivatives. The resulting compounds are racemic mixtures that can be derivatized to confer peripheral selectivity. If necessary, the final compounds or one of the intermediates can be resolved to test both enantiomers.

Scheme 5.

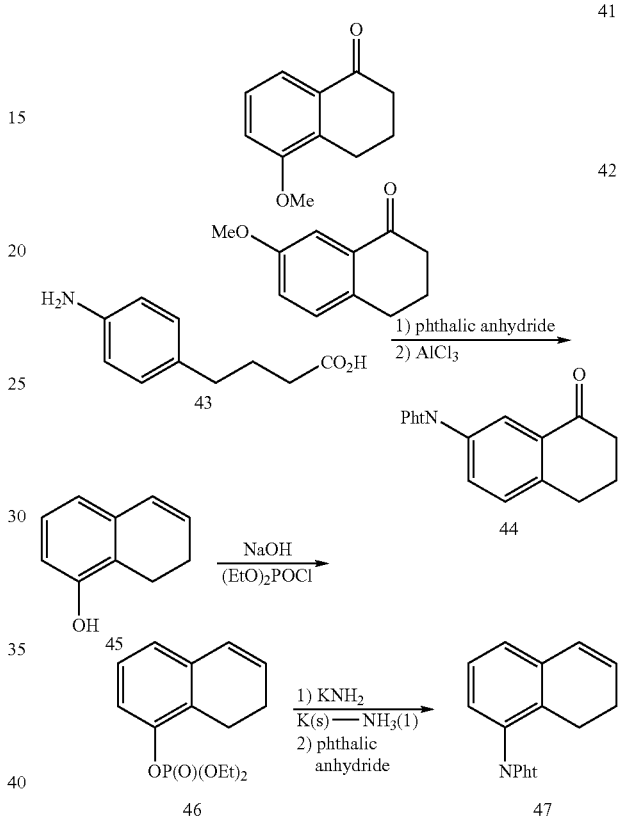

Scheme 6.

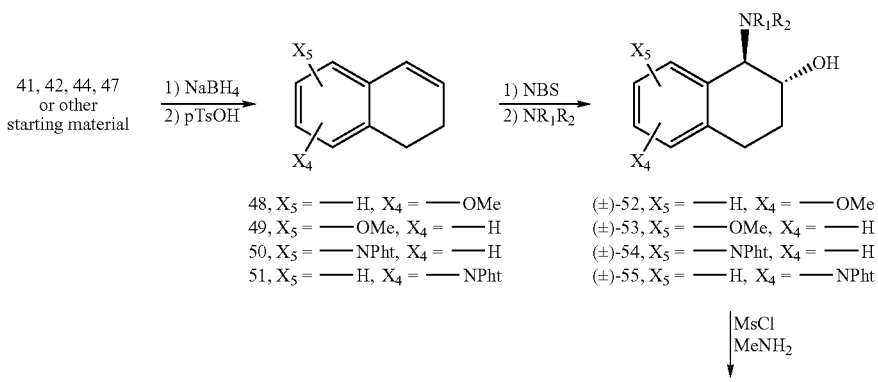

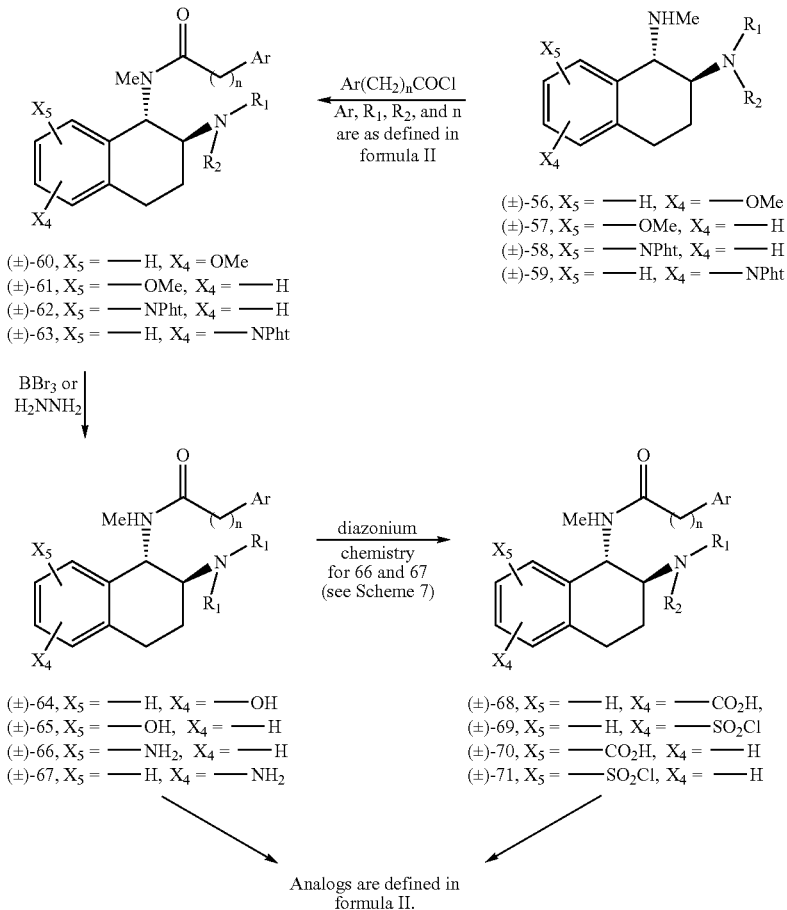
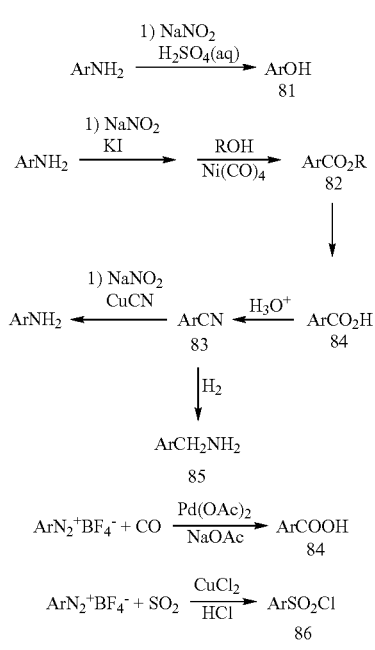
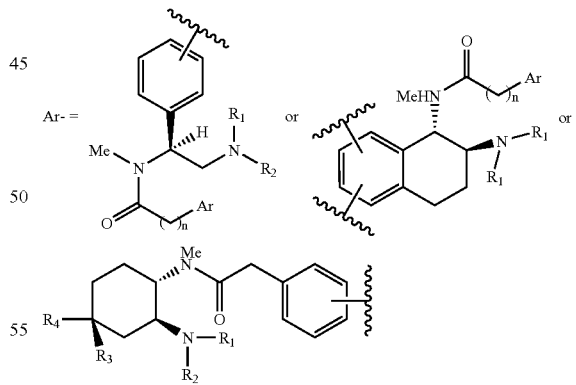
wherein $R_1$, $R_2$ are as defined in formula I.
Following the procedure shown in Schemes 5-7, the following example compounds are prepared.
Intermediate (±)-64 can be treated with t-butyl bromoacetate and deprotected to produce (±)-2-(3,4-dichlorophenyl)-N-methyl-N-1-[1,2,3,4-tetrahydro-5-(O-2-acetic acid)-hydroxy-2-(1-pyrrolidinyl)naphthyl]acetamide (72).

Intermediate (±)-65 can be treated with t-butyl bromoacetate and deprotected to produce (±)-2-(3,4-dichlorophenyl)-N-methyl-N-1-[1,2,3,4-tetrahydro-7-(O-2-acetic acid)-hydroxy-2-(1-pyrrolidinyl)naphthyl]acetamide (73).

Intermediate (±)-66 can be treated with methanesulfonyl chloride to produce (±)-2-(3,4-dichlorophenyl)-N-methyl-N-1-[1,2,3,4-tetrahydro-7-(N-methanesulfonamido)-amino-2-(1-pyrrolidinyl)naphthyl]acetamide (74).

Intermediate (±)-67 can be treated with methanesulfonyl chloride to produce (±)-2-(3,4-dichlorophenyl)-N-methyl-N-1-[1,2,3,4-tetrahydro-5-(N-methanesulfonamido)-amino-2-(1-pyrrolidinyl)naphthyl]acetamide (75).

Intermediate (±)-68 can be treated with glycine benzyl ester and deprotected to produce (±)-2-(3,4-dichlorophenyl)-N-methyl-N-1-[1,2,3,4-tetrahydro-5-(N-2-acetic acid)-carboxamido-2-(1-pyrrolidinyl)naphthyl]acetamide (76).

Intermediate (±)-69 can be treated with glycine benzyl ester and deprotected to produce (±)-2-(3,4-dichlorophenyl)-N-methyl-N-1-[1,2,3,4-tetrahydro-5-(N-2-acetic acid)-sulfonamido-2-(1-pyrrolidinyl)naphthyl]acetamide (77).

Intermediate (±)-70 can be treated with glycine benzyl ester and deprotected to produce (±)-2-(3,4-dichlorophenyl)-N-methyl-N-1-[1,2,3,4-tetrahydro-7-(N-2-acetic acid)-carboxamido-2-(1-pyrrolidinyl)naphthyl]acetamide (78).

Intermediate (±)-71 can be treated with glycine benzyl ester and deprotected to produce (±)-2-(3,4-dichlorophenyl)-N-methyl-N-1-[1,2,3,4-tetrahydro-7-(N-2-acetic acid)-sulfonamido-2-(1-pyrrolidinyl)naphthyl]acetamide (79).

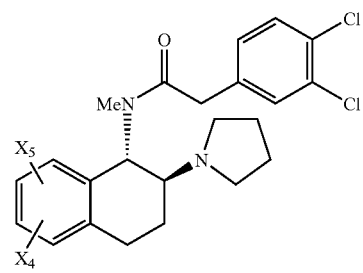

(±)-72, $X_5$ = ——H, $X_4$ = OCH$_2$CO$_2$H
(±)-73, $X_5$ = ——OCH$_2$CO$_2$H, $X_4$ =——H
(±)-74, $X_5$ = ——NHSO$_2$Me, $X_4$ =——H
(±)-75, $X_5$ = ——H, $X_4$ =——NHSO$_2$Me
(±)-76, $X_5$ = ——H, $X_4$ =——CONHCH$_2$CO$_2$H
(±)-77, $X_5$ = ——H, $X_4$ =——SO$_2$NHCH$_2$CO$_2$H
(±)-78, $X_5$ = ——CONHCH$_2$CO$_2$H, $X_4$ =——H
(±)-79, $X_5$ = ——SO$_2$NHCH$_2$CO$_2$H, $X_4$ =——H

The compounds of formula III of the present invention are prepared by substituting the central phenyl ring with polar groups.

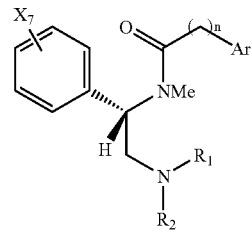

(III)

wherein Ar, $R_1$, $R_2$, $X_7$, and n are defined as in formula III.

Compound 80 and analogues undergo a variety of diazonium-involving reactions for the attachment of polar groups (Scheme 7).

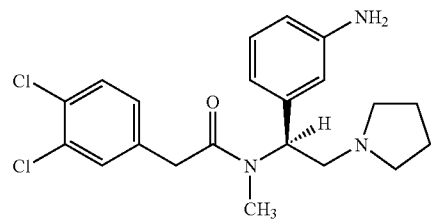

80

Using the procedure shown in Scheme 7, the following compounds are made.

Intermediate 81 can be treated with dibenzyl phosphoryl chloride followed by deprotection to produce 2-(3,4-dichlorophenyl)-N-methyl-N-{1-3-(O-phosphoryl)hydroxyphenyl-2-(1-pyrrolidinyl)ethyl}acetamide (87).

Intermediate 85 can be coupled to methanesulfonyl chloride to produce 2-(3,4-dichlorophenyl)-N-methyl-N-{1-[3-(N-methanesulfonamido)aminomethyl]phenyl-2-(1-pyrrolidinyl)ethyl}acetamide (88).

Intermediate 85 can be coupled to 2S-isothiocyanato succinic acid and deprotected to produce 2-(3,4-dichlorophenyl)-N-methyl-N-{1-[3-(N-succinic acid-2S-thioureido) aminomethyl phenyl-2-(1-pyrrolidinyl)ethyl}acetamide (89).

Intermediate 80 can be treated with dibenzyl phosphoryl chloride followed by deprotection to produce 2-(3,4-dichlorophenyl)-N-methyl-N-({-1-3-(N-phosphoramido) aminophenyl-2-(1-pyrrolidinyl)ethyl}acetamide (90).

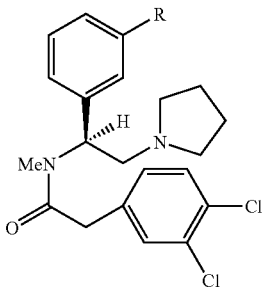

87, R = ——OPO$_3$H$_2$
88, R = ——CH$_2$NHSO$_2$Me
89, R = (S)-CH$_2$NHC(S)NHCH(CO$_2$H)CH$_2$CO$_2$H
90, R = ——NHPO$_3$H$_2$

The compounds of formula IV may be prepared by Scheme 8.

Scheme 8.

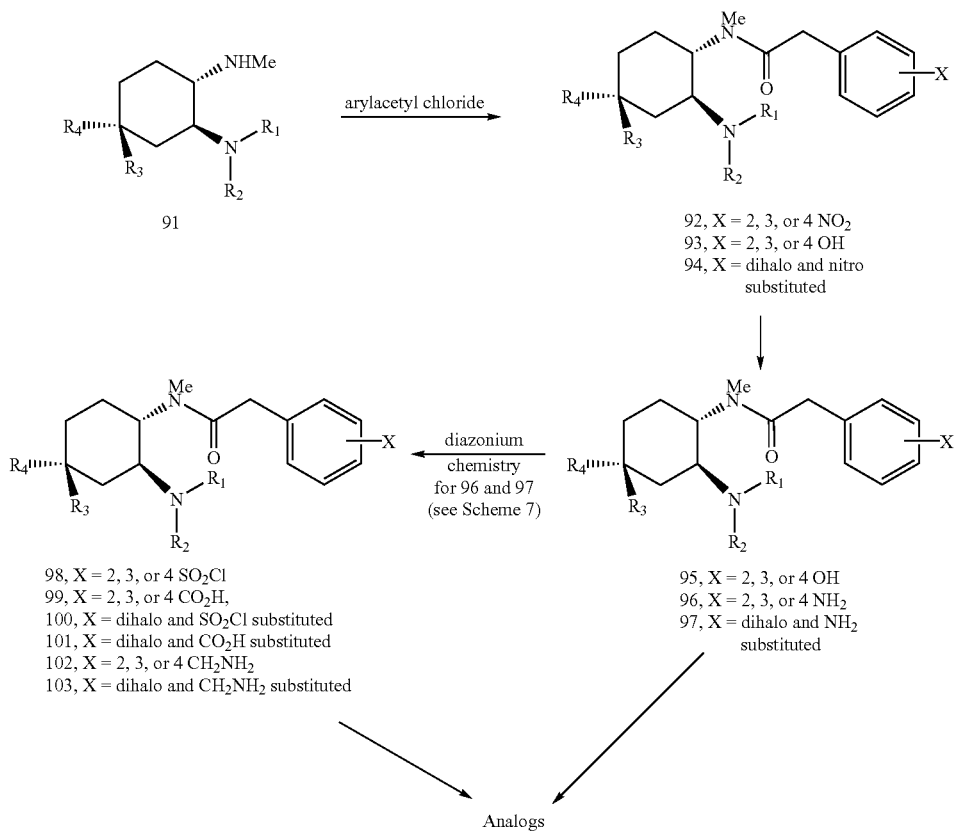

wherein $R_1$, $R_2$, $R_3$, and $R_4$ are defined in formulas III and IV.

The diamino intermediate 91 (J. Med. Chem. 1990, 33, 286) can be coupled to different regioisomers of nitrophenylacetic acid, which are all commercially available. Reduction of the nitro group provides an amino group for the attachment of polar groups. Alternatively, the amino intermediates 95-97 readily undergo diazonium chemistry that converts the amino groups to carboxyl and sulfonyl chloride groups. This allows the polar groups to be attached via different linkers.

Following the procedure in Scheme 8, the following compounds are made.

Intermediate 96 can be treated with methanesulfonyl chloride to produce (−)-(5α, 7α, 8β)-N-methyl-N-[7-(1-pyrrolidinyl)-1-oxaspiro-[4,5]dec-8-yl]-3-(N-methanesulfonamido)aminophenylacetamide (104).

Intermediate 98 can be coupled to glycine benzyl ester and deprotected to yield (−)-(5α, 7α, 8β)-N-methyl-N-[7-(1-pyrrolidinyl)-1-oxaspiro-[4,5]dec-8-yl]-3-(N-2-acetic acid)sulfonamidophenylacetamide (105).

Intermediate 99 can be coupled to glycine benzyl ester and deprotected to yield (−)-(5α, 7α, 8β)-N-methyl-N-[7-(1-pyrrolidinyl)-1-oxaspiro-[4,5]dec-8-yl]-3-(N-2-acetic acid)carboxamidophenylacetamide (106).

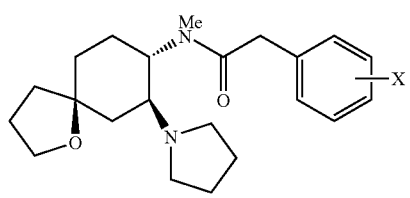

104, X = NHSO$_2$CH$_3$,
105, X = SO$_2$NHCH$_2$CO$_2$H
106, X - CONHCH$_2$CO$_2$H

Compounds of the above formulas may have one or more asymmetric carbon atoms. Pure stereochemically isomeric forms of the above compounds may be obtained, and diastereoisomers isolated by physical separation methods, including, but not limited to crystallization and chromatographic methods. Cis and trans diasteriomeric racemates may be further resolved into their isomers. If separated, active isomers may be identified by their activity. Such purification is not, however, necessary for preparation of the compositions or practice of the methods herein.

As used herein, the compounds provided herein also include pharmaceutically acceptable salts, acids and esters thereof, stereoisomers, and also metabolites or prodrugs thereof that possess activity as analgesics but do not cause substantial CNS effects when administered or applied. Metabolites include any compound that is produced upon administration of the compound and metabolism thereof.

More detailed preparations of the compounds of the present invention follow:

Compounds of Formula I

Preparatory for the compounds of formula I, the following intermediates were prepared.

N-Benzyl-D-serine (1)[1]: To a mixture of D-serine (25.0 g, 0.237 mol) and 200 mL anhydrous methanol was added sodium cyanoborohydride (11.95 g, 0.190 mol), while maintaining the temperature at 0° C. with an ice bath. Then, benzaldehyde (26.5 mL, 0.261 mol) was added to the reaction flask, dropwise, at 30° C. The mixture was stirred for 60 hr at room temperature. Then, the mixture was filtered and rinsed with methanol (50 mL). The white solid was dried in a vacuum oven at 40° C. and 10 mmHg over 2 nights: 24.5

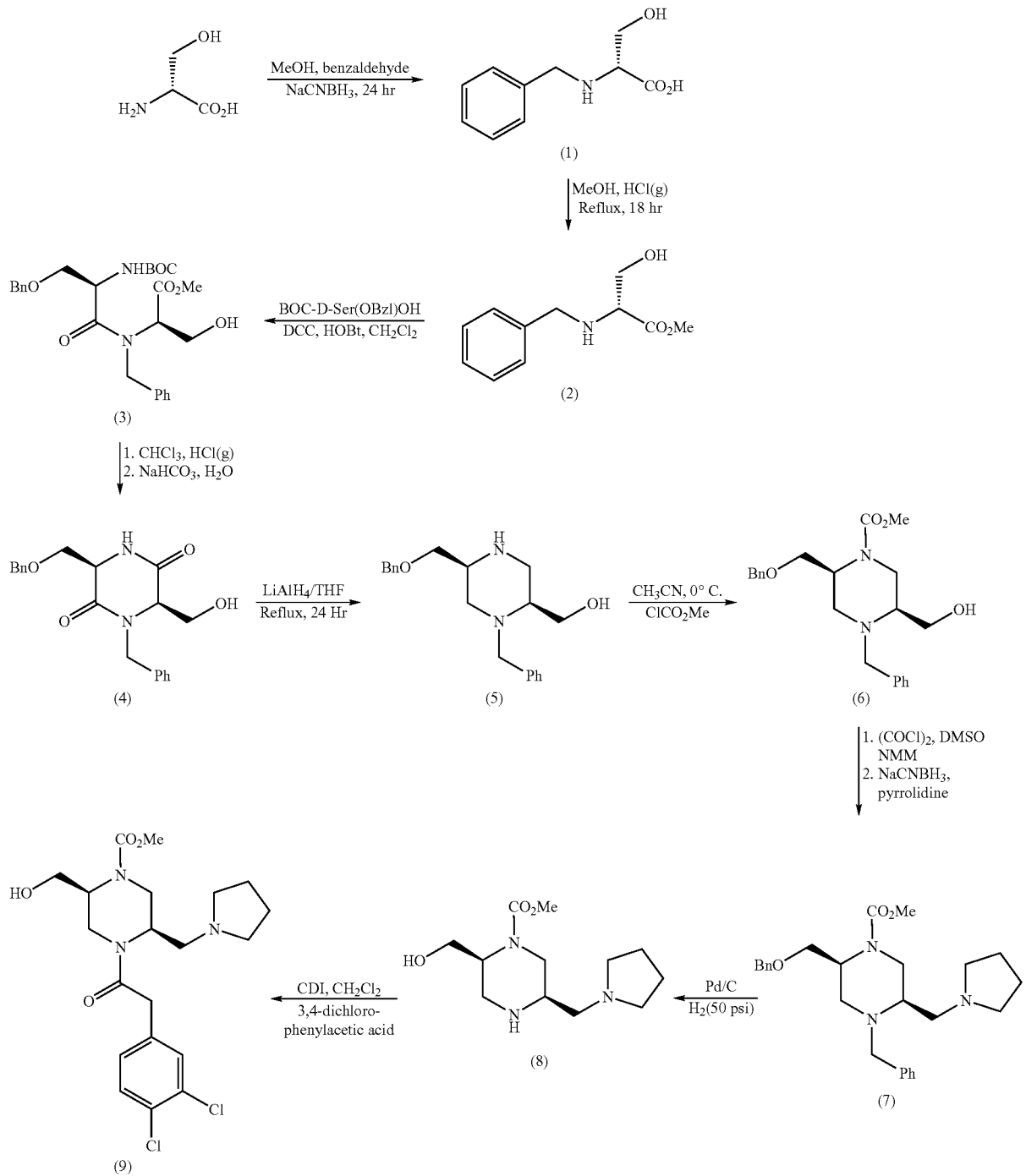

g. The filtrate was retained and the solvent was evaporated. This oil was passed through a silica gel column (10% MeOH/CH$_2$Cl$_2$) and 3.4 g of the desired compound was isolated. The total amount of the product was 27.9 g (60.0% yield). $^1$H NMR (DMSO-d$_6$) δ 3.25 (m, 1H, CH), 3.85 (m, 2H, CH$_2$), 4.11 (d, 2H, benzylic CH$_2$), 7.45-7.53 (m, 5H, ArH).

Ref.

(1) Ohfune, Y.; Kurokawa, N.; Higuichi, N.; Saito, M.; Hashimoto, M.; Tanaka, T. An efficient one-step reductive N-monoalkyation of amino acids. *Chemistry Letters*, 1984, 441-444.

N-Benzyl-D-serine methyl ester (2): Hydrogen chloride (gas) was bubbled into anhydrous methanol for 10 min. Then, the solution was allowed to cool to room temperature. Then, N-benzyl-D-serine (24.6 g, 0.126 mol) was added to the reaction flask and refluxed over night under dry nitrogen. Then, the solvent was evaporated and dissolved in dichloromethane (200 mL), and washed with a saturated solution of sodium bicarbonate. The dichloromethane layer was dried with magnesium sulfate and the solvent was evaporated (23 g, 87.2% yield).

$^1$H NMR (CDCl$_3$) δ 3.41 (d, 1H, CH), 3.52-3.80 (dd, 2H, benzylic), 3.69 (s, 3H, OMe), 7.27 (s, 5H, ArH).

N-[(1,1-Dimethylethoxy)carbonyl-D-Ser-(O-Bzl)-N-benzyl-D-Ser-OMe (3): To a solution of N-boc-D-serine-(O-bzl)OH (15 g, 50.76 mmol) in anhydrous dichloromethane (200 mL) was added HOBt (7.54 g, 55.8 mmol) at 0° C. under dry nitrogen. Then, DCC (11.5 g, 55.7 mmol) in dichloromethane (100 mL) was added dropwise to the reaction flask. Then, this mixture was stirred for 1 hr. Then, N-benzyl-D-serine-OMe (10 g, 47.8 mmol) in dichloromethane (100 mL) was added dropwise to the reaction flask, then, stirred for 4 days, filtered and rinsed with dichloromethane (100 ml). The white precipitate was DCU and HOBt. The filtrate was evaporated and re-dissolved in ethyl acetate (100 mL). Then, this was allowed to precipitate, overnight. This was filtered and rinsed with ethyl acetate. Then, this was isolated on a silica gel column (20% ethyl acetate/ exanes) to yield an oil-17.3 g, 74.3% yield.

$^1$H NMR (CDCl$_3$) δ 1.43 (s, 9H, t-Bu), 3.54 (t, 1H, OH), 3.72 (s, 3H, OMe), 3.75 (dd, 2H, CH$_2$) 3.79 (dd, 2H, CH$_2$), 4.41 (d, 2H, CH$_2$ benzylic), 4.43 (d, 2H, CH$_2$ benzylic), 7.27-7.30(m, 10H, ArH).

(2R,5R)-2-((Benzyloxy)Methyl)-5-(Hydroxymethyl)-4-(Phenylmethyl)-3,6-Piperazine Dione (4)$^2$:

Into anhydrous chloroform (300 mL) was bubbled hydrogen chloride (gas). Then, the dipeptide (3) (13.5 g, 27.7 mmol) in chloroform (100 ml) was added to the reaction flask. The flask was stoppered and stirred for 64 hr. Then, a saturated solution (100 ml) of sodium bicarbonate was added and stirred vigorously for 48 hr. The cyclization was completed at this point. The organic layer was separated from the aqueous layer in a 1L separatory funnel. The product was isolated from a silica gel column, eluting with dichloromethane-methanol-0.88 ammonia (96:2:2) to give (4) as an amorphous solid (6.0 g, 61.1% yield). $^1$H NMR (CDCl$_3$) δ 3.72-3.96 (m, 7H), 3.97-5.24 (dd, 2H, CH$_2$ benzylic), 4.45 (dd, 2H, CH$_2$ benzylic), 7.15-7.30 (m, 10H, ArH); MS (FAB) m/e 355 (MH$^+$).

Ref.

(2) Williams, T. M.; Ciccarone, T. M.; MacTough, S. C. et al., 2-Substituted piperazines as constrained amino acids. *J. Med. Chem.* 1996, 39, 1345-1348.

(2S,5S)-2-((Benzyloxy)methyl)4-(phenylmethyl)-5-piperazinemethanol (5): A suspension of lithium aluminum hydride (0.9 g, 23.7 mmol) in anhydrous tetrahydrofuran (40 mL) was treated with a solution of piperazinedione 4 (2.1 g, 5.92 mmol) in anhydrous tetrahydrofuran (200 mL). The reaction mixture was heated at reflux for 24 hr and then stirred at room temperature for 12 hr. Water (10 ml) was added followed by aqueous sodium hydroxide (1N, 10 mL) and water (10 mL). The mixture was filtered, and the filtrate was evaporated to give 5 (1.67 g, 86.4% yield) as a viscous oil. $^1$H NMR (CDCl$_3$) δ 2.58 (dd, 2H, CH$_2$), 2.61 (t, 1H, OH), 3.10 (dd, 2H, CH$_2$), 3.25 (dd, 2H, CH$_2$), 3.50 (dd, 2H, CH$_2$), 3.74 (s, 2H, CH$_2$), 4.41 (dd, 2H, CH$_2$ benzylic), 7.20-7.30 (m, 10H, ArH).

(2S,5S)-Methyl 2-[(Benzyloxy)methyl]-5-(hydroxymethyl)4-(phenylmethyl)-1-piperazine carboxylate (6)$^3$: A solution of 5 (1.67 g, 5.11 mmol) in acetonitrile (20 mL) was treated with a solution of methyl chloroformate (0.532 g, 5.63 mmol) in acetonitrile (10 mL) at 0° C. The mixture was stirred at ambient temperature for 30 min and then aqueous sodium carbonate solution (15 mL) was added. The organic solvent was removed, and the aqueous residue was extracted with chloroform (3×10 mL). The combined organic extracts were washed with aqueous sodium carbonate solution (10 mL), dried, and evaporated to give 6 (1.52 g, 77.3% yield) as an oil. $^1$H NMR (CDCl$_3$) δ 2.54 (dd, 2H, CH$_2$), 2.45 (t, 1H, OH). 2.72 (dd, 2H, CH$_2$), 3.51 (dd, 2H, CH$_2$), 3.67 (dd, 2H, CH$_2$), 3.69 (s, 3H, OMe), 3.81 (dd, 2H, CH$_2$), 4.44 (dd, 2H, CH$_2$ benzylic), 7.17-7.31 (10H, ArH).

(2S,5S)-Methyl 2-[(Benzyloxy)methyl]-5-[(1-pyrrolidinyl)methyl]-4-(phenylmethyl)-1-piperazinecarboxylate (7)$^3$: A solution of oxalyl chloride (0.545 mL, 6.24 mmol) in dichloromethane (10 mL) at −65° C. was treated with a solution of dimethyl sulfoxide (1.14 mL, 16.0 mmol) in dichloromethane (5 ml) maintaining the reaction temperature below −65° C. The mixture was stirred at −70° C. for 10 mm, and then a solution of the piperazinemethanol (6: 2 g, 5.19 mmol) in dichloromethane (20 mL) was added at such a rate that the reaction temperature was maintained below −65° C. The reaction mixture was stirred at −65° C. for 3 hr, and a solution of N-methylmorpholine (1.42 mL, 12.91 mmol) in dichloromethane (5 mL) was added. The mixture was stirred at −20° C. for 45 min and then washed with ice-cold hydrochloric acid (0.01 N, 100 mL and 50 mL), dried, evaporated, and placed on a high vacuum pump overnight. The residue was dissolved in methanol (10 mL) and was added to a solution of pyrrolidine (0.91 mL, 10.94 mmol) in methanol (10 mL) at −10° C., which had been adjusted to pH 6.0 by the addition of methanolic hydrogen chloride. Sodium cyanoborohydride (0.67 g, 10.66 mmol) and 4-Å molecular sieves (0.66 g) were added, and the mixture was stirred at ambient temperature for 18 hr. The mixture was filtered, and the ifitrate was evaporated to dryness. The residue was dissolved in aqueous sodium carbonate (1M, 25 mL) and extracted with dichloromethane (2×50 mL). The product was isolated from a silica gel column, eluting with clichioromethane-methanol (98:2) to give 71.0 g, 23.0% yield). $^1$H NMR (CDCl$_3$) δ 1.75 (m, 4H, CH$_2$CH$_2$), 2.46 (m, 3H), 2.48 (m, 4H, CH$_2$CH$_2$), 2.55 (dd, 2H, CH$_2$), 2.70-2.85 (m, 3H), 3.41 (dd, 2H, CH$_2$), 3.69 (s, 3H, OMe), 4.10 (m, 1H), 4.20 (m, 1H), 4.41 (dd, 2H, CH$_2$ benzylic), 7.10-7.3 1 (m, 10H, ArH); MS (FAB) m/e 438 (MH$^+$).

(3) Naylor, A.; Judd, D. B.; Lloyd, J. E.; Scopes, D. I. C.; Hayes, A. G.; Birch, P. J. A potent new class of K-10 Receptor agonist: 4-substituted 1-(arylacetyl)-2-[(dialkylamino)methyl] piperazines. *J. Med. Chem.* 1993, 36, 2075-2083.

(2S,5S)-Methyl 2-(Hydroxymethyl)-5-[(1-pyrrolidinyl)methyl]-1-piperazine carboxylate (8): A solution of 7 (0.25 g, 0.571 mmol) in ethanol (200 mL) was hydrogenated over 10% palladium on carbon (Degussa type EIOI NE/W) at 50 psi for 7 days, then filtered through celite and the filtrate was evaporated. (0.13 g, 0.5 mmol: 87% yield).

(2S,5S)-Methyl 4-[(3,4-Dichlorophenyl)acetyl]-2-(hydroxy)methyl-5-1(1-pyrrolidinyl)-methyl]-1-piperazinecarboxylate (9): To a solution of 1,1'-carbonyldiimiazole (0.20 g, 1.26 mmol) in dichloromethane (10 mL) was added portionwise 3,4-dichlorophenylacetic acid (0.25 g, 1.26 mmol) and the resulting solution stirred under nitrogen for 1 hr, at room temperature. A solution of 8 (0.13 g, 0.5 mmol) in dichloromethane (10 mL) was added and the mixture was allowed to stand at room temperature for 18 hr. The reaction mixture was washed with sodium carbonate solution (2 N, 2×10 mL), dried, and evaporated to give a viscous oil. This material was dissolved in a mixture of tetrahydrofuran (5 mL) and water (5 mL) and treated with lithium hydroxide (42 mg, 1.0 mmol). The reaction mixture was removed, and the aqueous residue was extracted with dichloromethane (3×10 mL). The combined organic extracts were dried and evaporated to give a colorless gum which was purified by flash column chromatography on silica gel, eluting with ethyl acetate-methanol (40:1) to give 9 (155 mg, 70%) as a colorless foam.

Utilizing the above-denoted intermediates, the following compounds were prepared.

Chiral Compounds

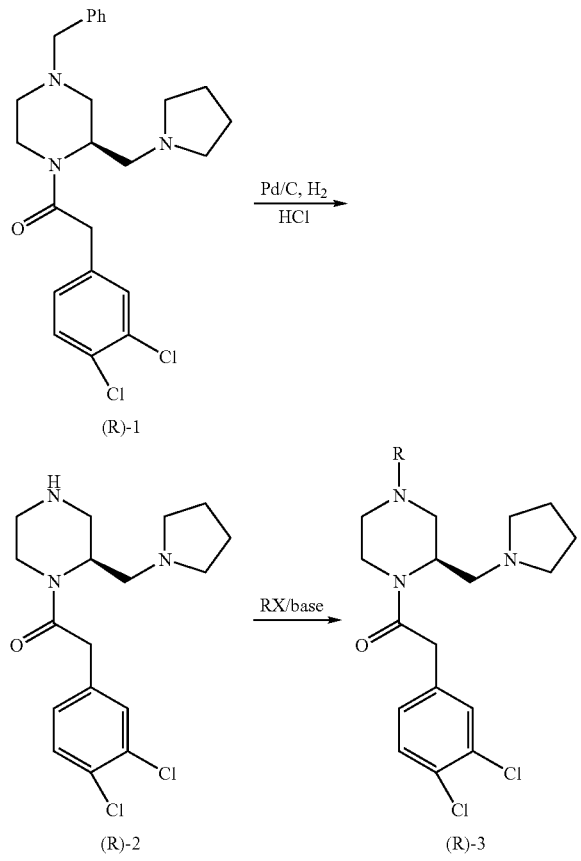

EXAMPLE 1

(R)-4-(Phenylmethyl)-1-[(3,4-dichlorophenyl)acetyl]-2-[(1-pyrrolidinyl)methyl]piperazine hydrochloride [(R)-1 HCl]

ADL-01-0143-6

The compound (R)-1 HCl was prepared following the literature procedure[3] in 54% yield; mp 168-170° C.; $^1$H NMR (free base, 200 MHz, CDCl$_3$) δ 1.65 (4H, m), 1.95-3.00 (6H, m), 3.10-3.80 (9H, m), 4.35 (1H, m), 4.70 (1H, m), 7.00 (1H, m), 7.30 (7H, m); MS (FAB) 448 (M+H)$^+$ Anal Calcd for C$_{24}$H$_{29}$Cl$_2$N$_3$O.2HCl.H$_2$O: C, 53.64; H, 6.19; N, 7.82. Found: C, 53.69; H, 5.88; N, 7.49.

EXAMPLE 2

(R)-1-[(3,4-dichlorophenyl)acetyl-2-[1-pyrrolidinyl)methyl]piperazine hydrochloride [(R)-2HCl]

ADL-01-0047-9

The compound was prepared by the catalytic hydrogenation of (R)-1 HCl following the procedure described in the above reference. The product was isolated as a free base as clear oil in 81% yield and the dihydrochioride salt was prepared from 1M etherial HCl; $^1$H NMR (free base, 200 MHz, CDCl$_3$) δ 1.67 (4H, m), 1.95-3.10 (6H, m), 3.10-3.80 (7H, m), 4.30 (1H, m), 4.65 (1H, m), 7.05 (1H, m), 7.35 (3H, m); MS (FAB) 356 (M+H)$^+$.

EXAMPLE 3

(R)-4-Methanesulfonyl-1-[(3,4-dichlorophenyl)acetyl-2-[(1-pyrrolidinyl)methyl]-piperazine hydrochloride [(R)-3αHCl]

ADL-01-0039-6

To the solution of (R)-2 (712 mg, 2 mmol in 10 ml CH$_2$Cl$_2$), methanesulfonyl chloride (573 mg, 5 mmol) and pyridine (1 ml) were added at 0° C., stirred overnight at that temperature, the solution was washed with aq. 5% K$_2$CO$_3$ solution, extracted with dichloromethane, dried and the solvent evaporated to give a crude oil. This material was purified by flash column chromatography on silica gel, eluting with dichloromethane-methanol-ammonia (100:5:1), to give the free base, which was dissolved into 2 ml of dichloromethane and HCl (3 ml, 1 M in Et$_2$O) was added to afford a white salt (R)-3a HCl (600 mg, 69%): mp 130-132° C.; $^1$H NMR (free base, 200 MHz, CDCl$_3$) δ 1.61-1.85 (4H, m), 2.38-2.65 (6H, m), 2.72 (3H, s), 2.80-3.06 (2H, m), 3.15-3.36 (1H, m), 3.50-3.96 (4H, m), 4.484.93 (1H, m), 7.00-7.10 (1H, m), 7.25-7.40 (2H, m); MS (FAB) 434 (M+H)$^+$; Anal. Calcd for C$_{18}$H$_{25}$Cl$_2$N$_3$O$_3$S. HCl0.5; CH$_3$OH: C, 45.64; H, 5.59; N, 8.63. Found: C, 45.69; H, 5.58; N, 8.73.

EXAMPLE 4

(R)-4-t-Butyl-acetyl-1-[(34-dichlorophenyl)acetyl]-2-[(1-pyrrolidinyl)methyl-piperazine [(R)-3b]

ADL-01-0040-4

To the solution of (R)-2 (356 mg, 1 mmol in 10 ml acetone), t-butyl bromoacetate (234 mg, 1.2 mmol) and K$_2$CO$_3$ (207 mg, 1.5 mmol) were added at 0° C., stirred overnight at that temperature, the solution was washed with aq. 5% $K_2CO_3$ solution, extracted with dichoromethane, dried and evaporated solvent to give crude oil. This material was purified by flash column chromatography on silica gel, eluting with dichloromethane-methanol-ammonia (100:5:1), to give (R)-3b (329 mg, 70%): $^1$H NMR (free base, 200 MHz, $CDCl_3$) δ 1.36 (9H, s), 1.91-2.37 (7H, m), 2.65-3.13 (7H, m), 3.58-4.20 (6H, m), 5.00 (1H, m), 7.12-7.21 (2H, m), 7.40 (1H, m). The compound was used directly into the following reaction.

EXAMPLE 5

(R)-4-[(3,4-dichlorophenyl)acetyl]-3-[(1-pyrrolidinyl)methyl]-1-piperazineacetic Acid dihydrochloride [(R)-3c 2HCl]

ADL-01-0042-0

Compound (R)-3b (329 mg, 0.7 mmol) was dissolved into 5 ml $THF/Et_2O$ (1:1), and HCl (5 ml, 1 M in $Et_2O$) was added, kept 12 hrs to afford a white salt (R)-3c HCl (275 mg, 61%): mp 190° C. (d). $^1$H NMR (free base, 200 MHz, $CDCl_3$) δ 1.85-2.20 (4H, m), 2.95-4.41 (17H, m), 5.18-5.35 (1H, m), 7.30-7.45 (1H, m), 7.56-7.72 (2H, m); MS (FAB) 414 (M+H+); Anal. Calcd for $C_{19}H_{25}Cl_2N_3O_3.2$ HCl.0.5 $H_2O$.: C, 45.16; H, 5.78; N, 8.32. Found: C, 44.91; H, 5.88; N, 856.

EXAMPLE 6

(R)-4-N-t-Boc-D-Aspartic Acid-13-benzyl Ester-1-[(3,4-dichlorophenyl)acetyl]-2-[(1-pyrrolidinyl]methyl-piperazine [(R)-3d]

ADL-01-0048-7

To the solution of N-t-Boc-D-aspartic acid-β-benzyl ester (646 mg, 2 mmol) and HOBt (270 mg, 2 mmol in 10 ml $CH_2Cl_2$), DCC (413 mg, 2 mmol) was added at 0° C., stirred 1 hr at that temperature, (R)-2 (356 mg, 1 mmol in 10 ml $CH_2Cl_2$) was added, stirred 24 hrs at room temperature, the solution was washed with aq. 5% $K_2CO_3$ solution, extracted with dichloromethane, dried and evaporated solvent to give a crude oil. This material was purified by flash column chromatography on silica gel, eluting with dichloromethane-methanol-ammonia (100:1:1), to give (R)-3d (628 mg, 95%), $^1$H NMR (free base, 200 MHz, $CDCl_3$) δ 1.35 (9H, s), 1.70-1.87 (4H, m), 2.32-3.16 (6H, m), 3.354.46 (6H, m), 4.80-5.68 (6H, m), 7.07-7.45 (8H, m). The compound was used directly into the reaction below.

EXAMPLE 7

(R)-4-Aspartic Acid-1-[(3,4-dichlorophenyl)acetyl]-2-[(1-pyrrolidinyl)methyl]-piperazine dihydrochloride [(R)-3e 2HCl]

ADL-01-0041-2

The compound (R)-3d was dissolved into 1 ml of HOAc, and HCl (1 ml, 2N) was added, standing 20 mm, then hydrogenated at 1 atm., 10% Pd on carbon at room temperature for 1 h to afford a white salt (R)-3e (430 mg, 91.5%): mp 168° C. (d). $^1$H NMR (DMSO-$d_6$) δ 1.92-2.16 (4H, m), 2.75-5.28 (18H, m), 2.72 (3H, s), 7.31-7.52 (3H, m), 8.45-8.80 (3H, m); MS (FAB) 471 (M+H)+ Anal. Calcd for $C_{21}H_{28}CL_2N_4O_4.2$ HCl: C, 46.34; H, 5.18; N, 10.29. Found: C, 45.52; H, 6.02; N, 9.73.

EXAMPLE 8

(R)-4-Acetyl-1-[(3,4-dichlorophenyl)acetyl]-2-[(1-pyrrolidinyl)methyl]-piperazine hydrochloride [(R)-3f HCl]

ADL-01-0148-5

The compound was prepared as reported in the literature (J. Med. Chem. 1993, 36, 2075-2083) from (R)-2. The hydrochloride salt was prepared from 1M etherial HCl to afford (R)-3f HCl in 88% yield; mp 153-155° C.; MS (FAB) 398 (M+H)$^+$. Anal. Calcd for $C_{19}H_{25}Cl_2N_3O_2.HCl.H_2O$: C, 52.49; H, 6.03; N, 9.66. Found: C, 50.40; H, 6.23; N, 9.28.

EXAMPLE 9

(R)-4-(Diethoxyphosphonate)-1-[(3,4-dichlorophenyl)acetyl]-2-[(1-pyrrolidinyl)methyl]-piperazine hydrochloride [(R)-3g HCl]

ADL-01-0149-3

To a solution of (R)-2 (0.178 g, 0.5 mmol) in 10 mL of $CH_2Cl_2$ was added $Et_3N$ (0.101 g, 1.0 mmol) and diethylchlorophosphonate (0.174 g, 1.0 mmol) under a nitrogen atmosphere. The reaction mixture was stirred at room temperature for 13 hr and then poured over aqueous 10% $K_2CO_3$. The organic layer was separated, dried over anhydrous $Na_2SO_4$, and evaporated to dryness under reduced pressure to give the compound as a yellow oil. The oil was purified on a silica gel column (solvent system: $CH_2Cl_2$:$CH_3OH$:28% $NH_4OH$, 95:5:2) and converted to hydrochloride salt by the usual method to give (R)-3g HCl, 0.10 g (38%); mp 168-170° C.; $^1$H NMR (free base, 200 MHz, $CDCl_3$) δ 1.20 (6H, t, J=7.0 Hz), 1.64 (4H, m), 2.30-2.70 (6H, m), 2.85-3.15 (1H, m), 3.45-3.80 (4H, m), 3.60 (2H, brs), 3.98 (4H, m), 4.35 (1H, m), 4,70 (1H, m), 7.00 (1H, m), 7.30 (2H, m); MS (FAB) 492, 494 (M+H)$^+$. Anal. Calcd for $C_{21},H_{32}Cl_2N_3O_4P.HCl.0.5H_2O$: C, 46.90; H, 6.37; N, 7.81. Found: C, 46.66; H, 5.90; N, 8.16.

EXAMPLE 10

(R)-4-Trifluoroacetyl-1-[(3,4-dichlorophenyl)acetyl]-2-[(1-pyrrolidinyl)methyl]-piperazine hydrochloride [(R)-3h) HCl]

ADL-01-0150-1

To a solution of (R)-2 (0.356 g, 1.0 mmol) in 10 mL of $CH_2Cl_2$ was added $Et_3N$ (0.202 g, 2.0 mmol) and trifluoroacetic anhydride (0.42 g, 2.0 mmol) in a nitrogen atmosphere. The reaction mixture was stirred at room temperature for 12 hr and TLC showed starting material was still present, added another equivalent of trifluoroacetic anhydride and stirring was continued for additional 12 hr. The reaction was worked up as above and the hydrochloride salt was prepared as usual to give (R)-3h HCl, 0.25 g (50%); mp 145-147° C.; $^1$H NMR (free base, 200 MHz, $CDCl_3$) δ 1.60 (4H, m), 2.20-2.75 (6H, m), 3.10 (1H, m), 3.45-3.80 (4H, m), 4.00 (1H, J=14.0 Hz, d), 4.25 (H, m), 4.45 (1H, J=14.0 Hz, d), 4.70 (1H, m), 7.00 (1H, m), 7.28 (2H, m); MS (FAB) 452, 454 (M+H)$^+$. Anal. Calcd for $C_{19}H_{22}Cl_2F_3N_3O_2.HClO.5H_2O$: C, 45.85; H, 4.86; N, 8.44. Found: C, 46.26; H, 4.82; N, 8.33.

EXAMPLE 11

(R)-4-[(3,4-Dichlorophenyl)acetyl]-3-[(1-pyrrolidinyl)methyl]-piperazinecarboxamide hydrochloride [(R)-3i HCl]

ADL-01-0151-9

To a solution of (R)-2 (0.356 g, 1.0 mmol) in acetic acid (0.186 g, 3.0 mmol) and water was added KOCN (0.244 g, 3.0 mmol) and the reaction mixture was stirred at room temperature for 72 h. An aqueous 10% $K_2CO_3$ was added to the reaction mixture to bring the pH to near 12.0 and the product was extracted with $CH_2Cl_2$, washed with saturated salt solution, and dried over anhydrous $Na_2SO_4$. The removal of solvent at reduced pressure gave the crude product which was purified on a silica gel column (solvent system: $CH_2Cl_2$:$CH_3OH$:28% $NH_4OH$, 95:5:1) to give the desired product as a white solid. The hydrochloride salt was prepared from 1M ethanol HCl to give (R)-3i HCl as a white solid, 0.15 g (31%); $^1$H NMR (free base, 200 MHz, $CDCl_3$) δ 1.65 (4H, m), 2.10-3.20 (6H, m), 3.40-3.70 (4H, m), 3.95 (2H, m), 4.20 (2H, J=14.0 Hz, d, m), 4.70 (1H, m), 5.35 (2H, bs), 7.00 (1H, m), 7.25 (2H, m); MS (FAB) 399, 401 (M+H)$^+$. Anal. Calcd for $C_{18}H_{24}Cl_2N_4O_2$·HCl·$H_2O$·0.125 $CH_2Cl_2$: C, 46.88; H, 5.91; N, 12.06. Found: C, 46.66; H, 5.50; N, 11.97.

EXAMPLE 12

(R)-4-[(3,4-Dichlorophenyl)acetyl]-3-1(1-pyrrolidinyl)methyl]-1-piperazinecarboxaldehyde hydrochloride [(R)-3 j HCl]

ADL-01-0156-8

To a solution of (R)-2 (0.356 g, 1.0 mmol) in 10 mL of $CH_2Cl_2$ was added 1.0 mL of methylformate (excess) at 0° C. under a nitrogen atmosphere. The reaction mixture was stirred for 24 h and solvent was removed at reduced pressure to give the crude product. The compound was purified on a silica gel column (solvent system: $CH_2Cl_2$:$CH_3OH$:28% $NH_4OH$, 95:5:1) and converted to the hydrochloride salt, (R)-3j HCl, 0.10 g (23%); mp 126° C. (d); $^1$H NMR (free base, 200 MHz, $CDCl_3$) δ 1.62 (4H, m), 2.10-3.20 (6H, m), 3.35-3.85 (5H, m), 4.25 (3H, m), 4.60 (1H, m), 7.00 (1H, m), 7.26 (2H, m), 7.90 (1H, s); MS (FAB) 384, 386 (M+H)$^+$.

EXAMPLE 13

(R)-4-[3,4-Dichlorophenyl)acetyl]-3-[(1-pyrrolidinyl)methyl]-1-piperazine-sulfonamide hydrochloride [(R)-3k. HCl]

ADL-01-0164-2

To a solution of (R)-2 (0.356 g, 1.0 mmol) in 5 mL of p-dioxane was added sulfamide[4] ($NH_2SO_2NH_2$, 0.96 g, 10 mmol) under a nitrogen atmosphere and the reaction mixture was heated to reflux for 2 h. The reaction mixture was evaporated to dryness under reduced pressure and the residue was redissolved in $CH_2Cl_2$ and washed with aqueous 10% $K_2CO_3$, saturated salt solution, and dried over anhydrous $Na_2SO_4$. The removal of solvent resulted in the free base of the product which was purified on a silica gel column (solvent system: $CH_2Cl_2$:$CH_3OH$:28% $NH_4OH$, 98:2:1). The hydrochloride salt was prepared from 1M etherial HCl to give (R)-3l HCl, 0.10 g (21%); mp 183-185° C.; $^1$H NMR (free base, 200 MHz, $CDCl_3$) δ 1.68 (4H, m), 2.30-3.00 (6H, m), 3.15-4.00 (5H, m), 4.15-4.65 (3H, m), 4.85 (1H, m), 7.00 (1H, m), 7.31 (4H, m); MS (FAB) 435 (M+H)$^+$. Anal. Calcd for $C_{17}H_{24}Cl_2N_4O_3S$·HCl: C, 43.28; H, 5.34; N, 11.87. Found: C, 42.90; H, 5.35; N, 11.43.

Ref.
(4) Alker, D. et. al. *J. Med. Chem.* 1990, 33, 585.

EXAMPLE 14

(R)-4-(4-Methylphenylsulfonyl)-1-[(3,4-dichlorophenyl)acetyl]-2-[(1-pyrrolidinyl)methyl]-piperazine hydrochloride [(R)-3l HCl]

ADL-01-0165-9

To a solution of (R)-2 (0.356 g, 1.0 mmol) in 5 mL of $CH_2Cl_2$ was added p-toluenesulfonyl chloride (0.38 g, 2 mmol) followed by 0.5 mL of pyridine under a nitrogen atmosphere. The reaction mixture was stirred at room temperature for 16 h and then poured onto aqueous 10% $K_2CO_3$. The organic layer was separated and dried over anhydrous $Na_2SO_4$. The removal of solvent gave the product which was purified on a silica gel column (solvent system: $CH_2Cl_2$:$CH_3OH$:28% $NH_4OH$, 98:2:1). The hydrochloride salt was prepared to give (R)-3l HCl, 0.15 g (27%); mp 240° C. (d); $^1$H NMR (free base, 200 MHz, $CDCl_3$) δ 1.65 (4H, m), 1.95-3.00 (6H, m), 2.38 (3H, s), 3.15-3.85 (5H, m), 4.45 (1H, m), 4.75 (1H, m), 6.95 (1H, m), 7.25 (4H, m), 7.50 (2H, J=8.0 Hz, d); MS (FAB) 510 (M+H)$^+$. Anal. Calcd for $C_{24}H_{29}Cl_2N_3O_3S$·HCl·0.25$H_2O$: C, 52.32; H, 5.35; N, 7.63. Found: C, 52.23; H, 5.50; N, 7.51.

Racemic Compounds

Racemic compounds were prepared as illustrated by the following steps.

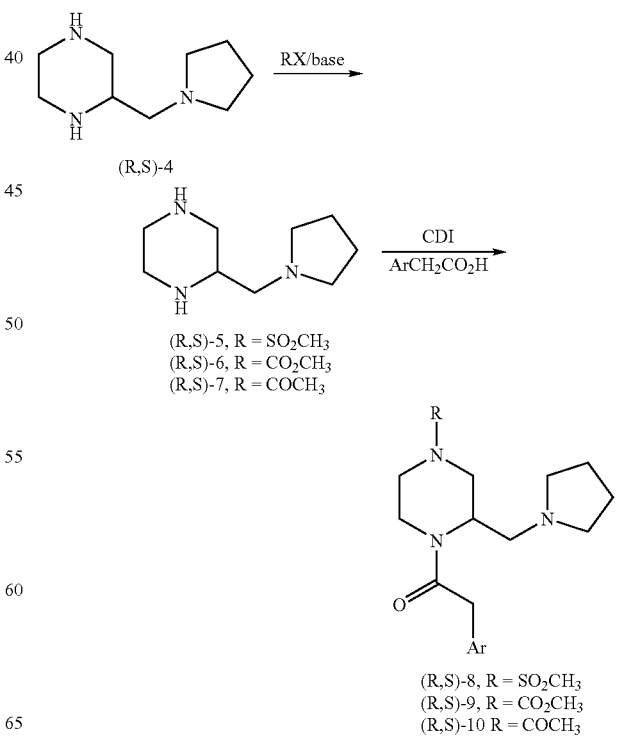

(R,S)-5, R = SO$_2$CH$_3$
(R,S)-6, R = CO$_2$CH$_3$
(R,S)-7, R = COCH$_3$ (R,S)-8, R = SO$_2$CH$_3$
(R,S)-9, R = CO$_2$CH$_3$
(R,S)-10 R = COCH$_3$ (R,S)-2-[(1-pyrrolidinyl)methyl]piperazine
hydrochloride [(R,S)-4 HCl]

The compound was prepared following the literature procedure and isolated as hydrochloride salt.

(R,S)-4-(R=SO$_2$CH$_3$, COCH$_3$)-2-[(1-pyrrolidinyl)
methyl]piperazine hydrochloride [(R,S)-5,6,7]

These compounds were also prepared according to the procedures described in the literature[1] and each of the products were purified as free base before utilizing below.

EXAMPLE 15

(R,S)-4-Methanesulfonyl-1-[(3,4-dichlorophenyl)
acetyl]-2-[(1-pyrrolidinyl)methyl]-piperazine hydrochloride [(R,S)-8a HCl](General Procedure)

ADL-01-0135-2

1,1'-Carbonyldiimidazole (0.324 g, 2.0 mmol) was added to a stirred solution of 3,4-dichlorophenylacetic acid (0.41 g, 2.0 mmol) in 10 mL of CH$_2$Cl$_2$ at room temperature under a nitrogen atmosphere, and the resulting solution was continued stirring for an additional 1 hr. The resulting solution was then added to a stirred solution of (R,S)-5 (0.247 g, 1.0 mmol) in 10 mL of CH$_2$Cl$_2$ at 0° C. and the reaction mixture was stirred for a further 20 h. The reaction mixture was diluted with CH$_2$Cl$_2$ and washed with aqueous 2M Na$_2$CO$_3$. The organic layer was dried and evaporated to dryness and the product was purified on a silica gel column (solvent system: CH$_2$Cl$_2$:CH$_3$OH:28% NH$_4$OH, 98:2:1). The hydrochloride salt was prepared by redissolving the compound in CH$_2$Cl$_2$ and treating the solution with 1M etherial HCl to give (R,S)-8a HCl as a white solid, 0.20 g (32%); NMR (see R-3a); MS (FAB) 434 (M+H)$^+$; Anal Calcd for C$_{18}$H$_{25}$Cl$_2$N$_3$O$_3$S.HCl.0.5H$_2$O: C, 45.13; H, 5.51; N, 8.77. Found: C, 45.46; H, 5.36; N, 8.71.

The following compounds were similarly prepared from (R,S)-5, 6, and 7:

EXAMPLE 16

(R,S)-4-Methanesulfonyl-1-[(4-methylsulfonylphenyl)acetyl]-2-[(1-pyrrolidinyl)-methyl]piperazine
hydrochloride [(R,S)-8b HCl]

ADL-01-0117-0

The compound was prepared from 4-methylsulfonylphenylacetic acid and the hydrochloride salt was recrystallized from CH$_3$OH to give (R,S)-8b HCl in 60% yield; mp 185-188° C.; $^1$H NMR (free base, 200 MHz, CDCl$_3$) δ 1.65 (4H, m). 2.30-2.70 (6H, m), 2.80 (3H, s), 2.85-3.10 (3H, m), 3.00 (2H, m), 3.25 (1H, m), 3.50-3.95 (4H, m), 4.50 (1H, m), 4.80 (1H, m)). 7.40 (2H, J=7.5 Hz, d), 7.80 (2H, J=7.5 Hz, d); MS (FAB) 444 (M+H)$^+$; Anal. Calcd for C$_{19}$H$_{29}$N$_3$O$_5$S$_2$.HCl: C, 47.54; H, 6.30; N, 8.75. Found: C, 46.03; H, 6.24; N, 8.80.

EXAMPLE 17

(R,S)-4-Methanesulfonyl-1-[(2-nitrophenyl)acetyl]-
2-[(1-pyrrolidinyl)-methyl]piperazine hydrochloride
[(R,S)-8c HCl]

ADL-01-0119-6

The compound was prepared from 2-nitrophenylacetic acid in 65% yield as hydrochloride salt; mp 253-255° C.; $^1$H NMR (free base, 200 MHz, CDCl$_3$) δ 1.70 (4H, m), 2.40-3.10 (6H, m), 2.75 (3H, s), 3.45 (1H, m), 3.70-4.00 (4H, m), 4.05-4.30 (2H, m), 4.50 (1H, m), 4.72 (1H, m), 7.45 (3H, m), 8.05 ($^1$H, J=8.0 Hz, d); MS (FAB) 411 (M+H)$^+$; Anal. Calcd for C$_{18}$H$_{26}$N$_4$O$_5$S.HCl: C, 48.37; H, 6.09; N, 12.54. Found: C, 48.36; H, 5.66; N, 12.29.

EXAMPLE 18

(R,S)-4-Methanesulfonyl-1-[(4-trifluoromethylphenyl)acetyl]-2-[(1(1-pyrrolidinyl)-methyl]piperazine
hydrochloride [(R,S)-8d HCl]

ADL-01-01204

The compound was prepared as a hydrochloride salt from 4-trifluoromethylphenylacetic acid in 82% yield; 182-185° C.; $^1$H NMR (free base, 200 MHz, CDCl$_3$) δ 1.65 (4H, m), 2.35-3.05 (6H, m), 2.71 (3H, s), 3.25 (1H, m), 3.50-3.95 (5H, m), 4.55 (1H, m), 4.85 (1H, m), 7.30 (2H, m), 7.50 (2H, J=7.8 Hz, d); MS (FAB) 434 (M+H)$^+$ Anal. Calcd for C$_{19}$H$_{26}$F$_3$N$_3$O$_3$S.HCl.0.5H$_2$O: C, 47.65; H, 5.89; N, 8.77. Found: C, 48.36; H, 5.80; N, 8.51.

EXAMPLE 19

(R,S)-4-Methanesulfonyl-1-[(3-indolylacetyl]-2-[(1-
pyrrolidinyl)-methyl]piperazine hydrochloride [(R,
S)-8e HCl]

ADL-01-0134-5

The compound was prepared from 3-indoleacetic acid and isolated as free base in 40% yield and converted to hydrochloride salt; mp 219-221° C.; $^1$H NMR (free base. 200 MHz, CDCl$_3$) δ 45 1.65 (4H, m), 2.10-3.00 (6H, m), 2.55 (3H, 5), 3.10-3.45 (2H, m), 3.45-3.90 (4H, m), 4.05 (1H, m), 4.55 (1H, m), 4.90 (1H, m), 7.05 (3H, m), 7.25 (1H, m), 7.50 (1H, m), 8.95 (1H, bs); MS (FAB) 405 (M+H)$^+$; Anal. Calcd for C$_{20}$H$_{28}$N$_4$O$_3$S.HCl.05H$_2$O: C, 58.09; H, 7.07; N, 13.55. Found: C, 58.37; H, 6.68; N, 13.30.

EXAMPLE 20

(R,S)-Methyl 4-[(4-methylsulfonylphenyl)acetyl]-3-
[(1-pyrrolidinyl)-methyl]-1-piperazinecarboxylate
hydrochloride [(R,S)-9a HCl]

ADL-01-0092-5

The compound was prepared from 4-methylsulfonylphenylacetic acid and the hydrochloride was prepared from 1M etherial HCl to give (R,S)-9a HCl in 46% yield; mp 225° C.; $^1$H NMR (free base, 200 MHz, CDCl$_3$) δ 1.60 (4H, m), 2.15-2.95 (6H, m), 2,98 (3H, s), 3.15 (2H, m), 3.35 (3H, m), 3.60 (3H, s), 3.95 (2H, m), 4.30 (1H, m), 4.72 (1H, m), 7.45 (2H, m), 7.75 (2H, J=7.5 Hz, d); MS (FAB) 424 (M+H)$^+$ Anal. Calcd for C$_{20}$H$_{29}$N$_3$O$_5$S.HCl.0.25H$_2$O: C, 51.72; H, 6.62; N, 9.05. Found: C, 51.93; H, 6.47; N, 8.44.

EXAMPLE 21

(R,S)-Methyl 4-[(4-trifluoromethylphenyl)acetyl]-3-[(1-pyrrolidinyl)-methyl]-1-piperazinecarboxylate hydrochloride [(R,S)-9b HCl]

ADL-01-0094-1

The compound was prepared as a hydrochloride salt from 4-trifluoromethylphenylacetic acid to give (R,S)-9b HCl.05 in 48% yield; mp 210° C.; $^1$H NMR (200 MHz, CDCl$_3$) δ 1.50 (4H, m), 1.95-2.30 (6H, m), 2.35-3.50 (4H, m), 3.65 (3H, S), 3.70-4.50 (5H, m), 7.45 (4H, m); MS (FAB) 414 (M+H)$^+$; Anal. Calcd for $C_{20}H_{26}F_3N_3O_3$.HCl.0.25H$_2$O: C, 52.86; H, 6.10; N, 9.25. Found: C, 53.03; H, 5.94; N, 8.94.

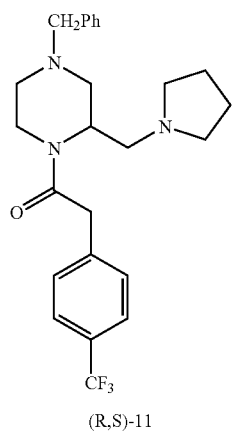

(R,S)-11

Another minor product (R,S)-11 (ADL-01-0093-3) was isolated as a hydrochloride salt from this reaction in 10% yield; mp 190° C.; MS (FAB) 446 (M+H)$^+$.

EXAMPLE 22

(R,S)-Methyl 4-[(3-indolyl)acetyl]-3-4(1-pyrrolidinyl)-methyl]-1-piperazinecarboxylate hydrochloride [(R,S)-9c HCl]

ADL-01-0095-8

The compound was prepared from 3-indoleacetic acid and the hydrochloride salt was prepared to give (R,S)-9c HCl in 75% yield; mp 143° C.; $^1$H NMR (200 MHz, CDCl$_3$) δ 1.55 (4H, m), 1.90-2.52 (6H, m), 2.70-3.75 (9H, m), 3.35 (3H, 5), 6.60 (2H, m), 6.85 (2H, m), 7.20 (1H, s), 107.65 (1H, brs); MS (FAB) 385 (M+H)$^+$.

EXAMPLE 23

(R,S)-Methyl 4-[(2-nitrophenyl)acetyl]-3-[(1-pyrrolidinyl)-methyl]-1-piperazinecarboxylate hydrochloride [(R,S)-9d HCl]

ADL-01-0096-6

The compound was prepared from 2-nitrophenylacetic acid and hydrochloride was prepared from 1M etherial HCl to give (R,S)-9d HCl in 42% yield; mp 228° C.; $^1$H NMR (free base, 200 MHz, CDCl$_3$) δ 1.60 (4H, brs), 1.80-2.30 (4H, m), 2.70 (2H, m), 3.05 (2H, m), 3.60 (3H, s), 3.55-4.10 (4H, m), 4.35 (2H, J=14.0 Hz, dd), 5.10 (1H, m), 7.50 (3H, m), 8.05 (1H, J=7.5 Hz, d); MS (FAB) 391 (M+H)$^+$ Anal. Calcd for $C_{19}H_{26}N_4O_5$.HCl: C, 53.46; H, 6.37; N, 13.12. Found: C, 54.29; H, 6.38; N, 12.58.

EXAMPLE 24

(R,S)-Methyl 4-[(2-methoxyphenyl)acetyl]-3-[(1-pyrrolidinyl)-methyl]-1-piperazinecarboxylate hydrochloride [(R,S)-9e HCl]

ADL-01-0097-4

The compound was prepared as above from 2-methoxyphenylacetic acid to give (R,S)-9e HCl in 12% yield; mp 120° C.; $^1$H NMR (free base, 200 MHz, CDCl$_3$) δ 1.65 (4H, m), 2.25-2.95 (6H, m), 3.10 (1H, m), 3.30-4.10 (5H, m), 3.60 (3H, s), 3.70 (3H, s), 4.40 (1H, m), 4.70 (1H, m), 6.84 (2H, m), 7.15 (3H, m); MS (FAB) 376 (M+H)'; Anal. Calcd for $C_{20}H_{29}N_3O_4$.HCl.H$_2$O: C, 55.87; H, 7.50; N, 9.77. Found: C, 55.78; H, 6.97; N, 9.42.

EXAMPLE 25

(R,S)-Methyl 4-[(2-aminophenyl)acetyl]-3-[(1-pyrrolidinyl)-methyl]-1-piperazinecarboxylate dihydrochloride [(R,S)-9f 2HCl]

ADL-01-0098-2

The compound was prepared by the hydrogenation of (R,S)-9e HCl on 10% Pd/C following the procedure described in the literature. The compound, (R,S)-9f 2HCl, was isolated as dihydrochloride in 84% yield; mp 195° C. (d); $^1$H NMR (200 MHz, DMSO-D$_6$) 62.00 (4H, m), 3.05-4.45 (16H, m), 3.75 (3H, s), 5.00 (1H, m), 7.45 (4H, brs); MS (FAB) 361 (M+H)$^+$; Anal. Calcl for $C_{19}H_{28}N_4O_3$.2HCl.H$_2$O: C, 50.56; H, 7.15; N, 12.41. Found: C, 50.36; H, 7.26; N, 12.05.

EXAMPLE 26

(R,S)-4-Acetyl-1-[(4-methylsulfonylphenyl)acetyl]-3-[(1-pyrrolidinyl)-methyl]-piperazine hydrochloride [(R,S)-10a HCl]

ADL-01-0144-4

The compound was prepared as above from 4-methylsulfonylphenylacetic acid and the hydrochloride salt was prepared in usual fashion to give (R,S)-10a HCl in 45% yield; mp 145-147° C.; $^1$H NMR (200 MHz, DMSO-d$_6$) δ 1.90 (4H, m), 2.17 (3H, s), 2.65-3.80 (6H, m). 3.32 (3H, s), 3.85-4.45 (8H, m), 5.05 (1H, m), 7.65 (2H, J=8.0 Hz, d), 7.95 (2H, J=8.0 Hz, d); MS (FAB) 408 (M+H)$^+$.

EXAMPLE 27

(R,S)-4-Acetyl-1-(4-trifluoromethylphenyl)acetyl]-3-[(1-pyrrolidinyl)-methyl]-piperazinecarboxylate hydrochloride [(R,S)-10b HCl]

ADL-01-0145-1

The compound was prepared from 4-trifluoromethylphenylacetic acid and isolated as hydrochloride salt, (R,S)-10b HCl, in 30% yield; mp 110° C.; $^1$H NMR (200 MHz, DMSO-d$_6$) δ 2.00 (4H, m), 2.15 (3H, s), 2.70-3.25 (6H, m), 3.50-4.45 (8H, m), 5.05 (1H, m), 7.70 (4H, m); MS (FAB) 398 (M+H)$^+$.

EXAMPLE 28

(R,S)-4-Acetyl-1-[(2-trifluoromethylphenyl)acetyl]-3-[(1-pyrrolidinyl)-methyl]piperazinecarboxylate hydrochloride [(R,S)-10c HCl]

ADL-01-0157-6

The compound was prepared from 2-trifluoromethylphenylacetic acid and the hydrochloride salt was made from 1M etherial HCl to give (R,S)-10c HCl in 57%; 220° C. (d); $^1$H NMR (free base, 200 MHz, CDCl$_3$) δ 1.65 (4H, m), 2.05 (3H, s), 2.25-3.25 (6H, m), 3.40-4.10(611, m), 4.50 (2H, m), 4.70 (1H, m), 7.30 (2H, m), 7.60 (2H, m); MS (FAB) 398 (M+H)$^+$.

EXAMPLE 29

(R,S)-4-Acetyl-1-[(3-nitrophenyl)acetyl]-3-[(1-pyrrolidinyl)-methyl]-piperazinecarboxylate hydrochloride [(R,S)-10d HCl]

ADL-01-0158-4

The compound was prepared from 3-nitrophenylacetic acid and the hydrochloride salt, (R,S)-40 10d HCl was isolated as a white solid in 69% yield; mp 143-145° C.; $^1$H NMR (free base, 200 MHz, CDCl$_3$) δ 1.63 (4H, brs), 2.05 (3H, s), 2.20-2.80 (6H, m), 2.90-3.25 (2H, m), 3.50-3.90 (3H, m), 4.00 (1H, J=14.0 Hz, d), 4.45 (21-1, m), 4.65 (1H, m), 7.45 (211, m), 8.00 (2H, m); MS (FAB) 375 (M+H)$^+$ Anal. Calcd for C$_{19}$H$_{26}$N$_4$O$_4$.HCl.H$_2$O: C, 53.21; H, 6.81; N, 13.06. Found: C, 53.51; H, 6.13; N, 12.91.

EXAMPLE 30

(R,S).4-Acetyl-1-[(2-nitrophenyl)acetyl]-3-[(1-pyrrolidinyl)-methyl]-piperazinecarboxylate hydrochloride [(R,S)-10e HCl]

ADL-01-0163-4

The compound was prepared as above from 2-nitrophenylacetic acid to give (R,S)-10e HCl as white solid in 50% yield; mp 180° C. (d); $^1$H NMR (free base, 200 MHz, CDCl$_3$) δ 1.63 (4H, m), 2.04 (3H, s), 2.20-2.85 (6H, m), 2.98-3.35 (3H, m), 3.60-4.25 (4H, m), 4.60 (2H, m), 7.3 (3H, m), 8.00 (1H, J=7.0 Hz, d); MS (FAB) 375 (M+H)$^+$; Anal. Calcd for C$_{19}$H$_{26}$N$_4$O$_4$.HCl.0.5H$_2$O: C, 55.54; H, 6.62; N, 13.64. Found: C, 54.38; H, 6.35; N, 13.58.

EXAMPLE 31

(R,S)-4-Acetyl-1-[4-nitrophenyl)acetyl]-3-[(1-pyrrolidinyl)-methyl]-piperazinecarboxylate hydrochloride (R,S)-10f HCl]

ADL-01-0159-2

The compound was prepared from 2-nitrophenylacetic acid as before to give (R,S)-1Of HCl in 52% yield; 146-148° C.; $^1$H NMR (free base, 200 MHz, CDCl$_3$) δ 1.68 (4H, m), 2.07 (3H, s), 2.20-2.75 (6H, m), 3.40-3.90 (3H, m), 4.05 (111, J=13.5 Hz, d), 4.50 (211, m), 7.35 (2H, J=8.0 Hz, d), 8.10 (2H, J=8.0 Hz, d); MS (FAB) 375 (M+H)$^+$; Anal. Calcd for C$_{19}$H$_{26}$N$_4$O$_4$.HCl.0.5H$_2$O.0.125CH$_2$Cl$_2$: C, 53.36; 6.61; 13.01. Found: C, 53.16; H, 6.27; N, 13.36.

EXAMPLE 32

(R,S)-4-(Phenylmethyl)-1-[(4,5,-dichloro-2-nitrophenyl)acetyl]-2-[(1-pyrrolidinyl)methyl]piperazine dihydrochloride [(R,S)-12 2HCl]

ADL-01-0166-7

The compound was prepared from 4-phenylmethyl-2[(1-pyrrolidinyl)methyl]piperazine (Ref. 1) and 4,5-dichloro-2-nitrophenylacetic acid following the method described above to give (R,S)-12 2HCl in 63% yield; mp 235° C. (d); $^1$H NMR (free base, 200 MHz, CDCl$_3$) δ 1.66 (4H, m), 2.05-3.00 (8H, m), 3.45 (4H, m), 4.00 (5H, m), 4.60 (1H, m), 7.35 (6H, m), 8.15 (1H, s); MS (FAB) 493 (M+H)$^+$; Anal. Calcd for C$_{24}$H$_{29}$Cl$_2$N$_4$O$_3$.2HCl: C, 50.99; 5.53; 9.91. Found: C, 50.55; H, 5.16; N, 9.44.

Compounds of Formula II

General procedure for DCC/pyr coupling. With stirring at 25° C. under N$_2$, DCC (2.06 eq) and CH$_2$Cl$_2$ were added to a mixture of the acid (2 eq) and pyridine (2.06 eq) in CH$_2$Cl$_2$. After 1-2 min, a solution of the amine (1 eq) in CH$_2$Cl$_2$ was added, and the mixture was stirred at 25° C. under N$_2$ overnight. The final concentration of the mixture is around 0.1-0.3 mM with respect to the amine. Sat'd. NaHCO$_3$ (2 mL) was added to destroy excess active esters before the mixture was filtered through celite, and the DCU was washed with CH$_2$Cl$_2$. The filtrate was then partitioned between sat'd NaHCO$_3$ and CH$_2$Cl$_2$, which was dried

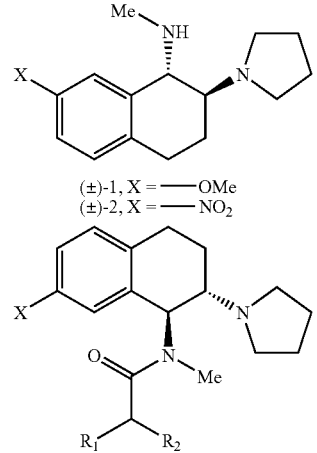

(±)-1, X = ——OMe
(±)-2, X = ——NO$_2$ (Na$_2$SO$_4$), filtered through celite, and evaporated. Toluene was added to azeotrope off pyridine before the crude product was chromatographed and converted to the HCl salt.

Compounds having the following structures were prepared:

(±)-3, ADL-01-0017-2, X=—OMe, R$_1$=—H, R$_2$=3,4-Cl$_2$-phenyl
(±)-4, ADL-01-0018-0, X=—OH, R$_1$=—H, R$_2$=3,4-Cl$_2$-phenyl
(±)-5, ADL-01-0019-8, X=—OCH$_2$CO$_2$H, R$_1$=—H, R$_2$=3,4-Cl$_2$-phenyl
(±)-6, ADL-01-0020-6, X=—OMe, R$_1$=R$_2$=phenyl
(±)-7, ADL-01-0021-4, X=—OH, R$_1$=R$_2$=phenyl
(±)-8, ADL-01-0029-7, X=—NO$_2$, R$_1$=—H, R$_2$=2-NO$_2$-4,5-Cl$_2$-phenyl
(±)-9, ADL-01-0031-3, X=—NO$_2$, R$_1$=—H, R$_2$=3,4-Cl$_2$-phenyl (±)-10, ADL-01-0032-1, X=—NH$_2$, R$_1$=—H, R$_2$=3,4-Cl$_2$-phenyl (±)-11, ADL-01-0034-7, X=—NO$_2$, R$_1$=—H, R$_2$=4-methylsulfonylphenyl (±)-12, ADL-01-0037-0, X=—N(CH$_2$CO$_2$tBu)$_2$, R$_1$=—H, R$_2$=3,4-Cl$_2$-phenyl (±)-13, ADL-01-0044-6, X=—N(CH$_2$CO$_2$H)$_2$, R$_1$=—H, R$_2$=3,4-Cl$_2$-phenyl (±)-14, ADL-01-0052-9, X=—N(CH$_2$CO$_2$Et)$_2$, R$_1$=—H, R$_2$=3,4-Cl$_2$-phenyl (±)-15, ADL-01-0053-7, X=—NHPO$_3$Et$_2$, R$_1$=—H, R$_2$=3,4-Cl$_2$-phenyl (±)-16, ADL-01-0070-1, X=—NH(CH$_2$)$_2$PO$_3$Et$_2$, R$_1$=—H, R$_2$=3,4-Cl$_2$-phenyl Intermediates (±)-1 and (±)-2 were prepared via reported methods from the appropriate starting materials.[5] Compounds (±)-3 and (±)-4 are known compounds prepared via reported methods.[5] Compounds (±)-5 through (±)-16 were prepared by DCC coupling of either (±)-1 or (±)-2 to an arylacetic acid followed by demethylation or reduction to allow peripheralization.

Ref.

(5) Rajagopalan, P. et al., Bioorg. Med. Chem. Letters 1992, 2, 721-726.

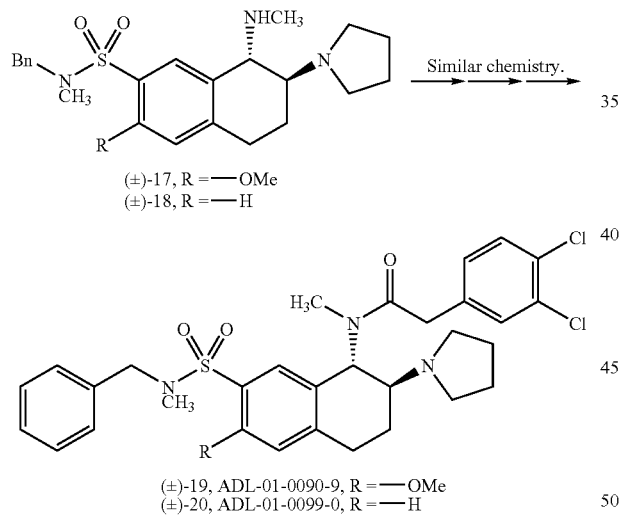

Intermediates 17 and 18 were prepared via known methods from 6-methoxy-1-tetralone and 1-tetralone, respectively. Intermediates 17 and 18 were coupled to 3,4-dichlorophenylacetic acid to produce (±)-19 and (±)-20.

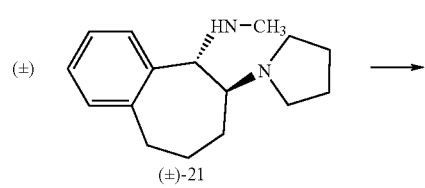

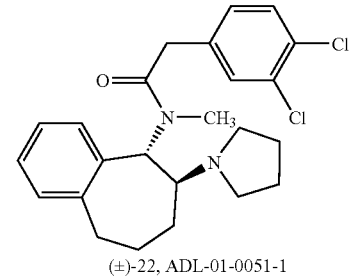

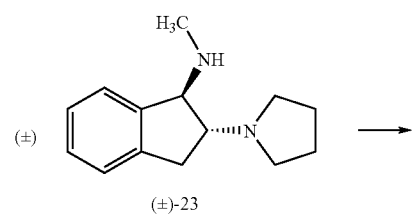

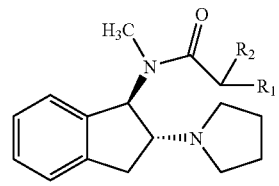

Intermediates (±)-21 and (±)-23 were prepared via similar chemistry from 1-benzosuberone and (±)-trans-2-bromo-1-indanol. 1 Compounds (±)-22, (±)-25 (Niravoline),[6] and (±)-27 are known compounds prepared via reported chemistry.[1] Compounds (±)-24 through (±)-29 were prepared by DCC coupling to the appropriate arylacetic acid.

Ref.

(6) Bellissant, E. et al., J. Pharmacol. Exp. Ther. 1996, 278, 232-242.

Representative examples follow.

EXAMPLE 33

2-{7-[(±)-trans-1-(N-34-dichlorophenylacetamido-N-methylamino)-2-(1-pyrrolidinyl)-1,2,3,4-tetrahydronaphthoxy]}Acetic Acid ((±)-5, ADL-01-0019-8)

With stirring at 25° C. under N$_2$, t-butyl bromoacetate (0.35 mL, 2.38 mmol) was added to a mixture of (±)-4 (0.688 g, 1.59 mmol) and K$_2$CO$_3$ (0.5 g 3.6 mmol) in DMF (8 mL), and the mixture was stirred at 25° C. under N$_2$ overnight before the mixture was evaporated under high vacuum. The residue was partitioned between sat'd NaHCO$_3$ and CH$_2$Cl$_2$ (2×100 mL), which was dried (Na$_2$SO$_4$), filtered through celite, and evaporated. The t-butyl ester intermediate was flash column chromatographed twice eluting with CH$_2$Cl$_2$:2% NH$_3$:2% MeOH and CH$_2$Cl$_2$:2% NH$_3$:1% MeOH, respectively. The t-butyl ester was then deprotected in a mixture of THF (4 mL) and conc. HCl (2 mL) with stirring at 25° C. overnight and at 50° C. for 1 hr before the mixture was evaporated. The residue was then dissolved in a mixture of trifluoroacetic acid (2 mL), 4 N HCl (2 mL), and anisole (1 drop), and stirred at 25° C. for 2.5 days before the mixture was evaporated. The oily residue was triturated with Et$_2$O and sonicated to yield (±)5HCl (0.259 g, 31%): imp. (HCl salt) 138° C. (dec); $^1$H NMR (HCl salt, DMSO-d$_6$) δ 1.7-2.1 (br s, 4H, —CH$_2$CH$_2$—), 2.2-4.8 (complex, 13H, 6—CH$_2$— and 1—CH—), 2.79 (s, 3H, —NCH$_3$), 5.98 (d, J=10.3 Hz, 1H, —CH-), 6.40 (s, 1H, aromatic), 6.82 (m, 1H, aromatic), 7.12 (d, J 8.2 Hz, 1H, aromatic), 7.39 (d, J=8.3 Hz, 1H, aromatic), 7.63 (m, 2H, aromatic). MS (FAB) m/z 491. Anal. (C, H, N) C$_{25}$H$_{28}$N$_2$O$_4$Cl$_2$HCl.

EXAMPLE 34

2.2-Diphenyl-N-methyl-N-[(±)-trans-2-(1-pyrrolidinyl)-7-Methoxy-1,2,3,4-tetrahydronaphth-1-yl]acetamide ((±)-6, ADL-01-0020-6)

ADL-01-0020-6 was prepared via the general DCC/pyr coupling method from (±)-1 (1.453 g, 5.58 mmol), diphenylacetic acid (2.369 g, 11.16 mmol), DCC (2.373 g, 11.50 mmol), and pyridine (0.93 mL, 11.5 mmol). The product was flash column chromatographed eluting with CH$_2$Cl$_2$:2% NH$_3$: 1% MeOH before it was converted to the HCl salt with 1.0 M HCl in Et$_2$O and crystallized from MeOH-Et$_2$O to yield (±)-6HCl (1.7 g, 63%): m.p. (HCl salt) >250° C.; $^1$H NMR (HCl salt, DMSO-d$_6$) δ 1.8-2.0 (br s, 4H, —CH$_2$CH$_2$-), 2.2-3.9 (complex, 9H, 4-CH$_2$— and 1 —CH—), 2.79 (s, 3H, —NCH$_3$), 3.48 (s, 3H, —OCH$_3$), 5.66 (s, 1H, —CH—), 6.1 (d, J=9.4 Hz, 1H, —CH—), 6.23 (s, 1H, aromatic), 6.77 (d of d, J=2.4 Hz and 8.4 Hz, 1H, aromatic), 7.09 (d, J=8.5 Hz, 1H, aromatic), 7.2-7.5 (complex, 10H, aromatic). MS (FAB) m/z 455. Anal. (C, H, N) C$_{30}$H$_{34}$N$_2$O$_2$HCl.

EXAMPLE 35

2,2-Diphenyl-N-methyl-N-[(±)-trans-2-(1-pyrrolidinyl)-7-hydroxy-1,2,3,4-tetrahydronaphth-1-yl]acetamide ((±)-7, ADL-01-0021-4)

With stirring in dry ice-acetone under N$_2$, 1.0 M Br$_3$ in CH$_2$Cl$_2$ (19.7 mL) was added at a fast drop rate to a solution of (±)-6 (1.49 1 g, 3.28 mmol) in CH$_2$Cl$_2$ (20 mL), and the mixture was allowed to slowly warm to 25° C. under N$_2$ as the dry ice sublimed. After 6.5 h, the mixture was quenched with MeOH with ice-H$_2$O cooling and diluted with CH$_2$CL$_2$ (50 mL). The mixture was partitioned between sat'd NaHCO$_3$ and CH$_2$Cl$_2$. Some yellowish precipitate was extracted into CH$_2$Cl$_2$ by adding some MeOH. The organic fraction was dried (Na$_2$SO$_4$), filtered through celite, and evaporated. The product was flash colum chromatographed eluting with CHCl$_3$:2% NH$_3$:2% MeOH to yield (±)-7 (0.426 g, 30%). Part of the free base was converted to the HCl salt with 1.0 M HCl in Et$_2$O: $^1$H NMR (free base, CDCl$_3$) δ 1.5-1.8 (br s, 4H, —CH$_2$CH$_2$—), 1.8-2.9 (complex, 9H, 4—CH$_2$- and I —CH—), 2.55 (s, 3H, —NCH$_3$), 5.21 (s, 1H, —CH—), 5.83 (d, J=8.6 Hz, 1H, —CH—), 6.22 (s, 1H, aromatic), 6.46 (m, 1H, aromatic), 6.78 (d, J=8.1 Hz, 1H, aromatic), 7-7.4 (complex, 1OH, aromatic). MS (FAB) m/z 441. Anal. (C, H, N) C$_{29}$H$_{32}$N$_2$O$_2$HCl.H$_2$O.

EXAMPLE 36

2-(2-Nitro-4,5-dichlorophenyl)-N-methyl-N-[(±)-trans-2-(1-pyrrolidinyl)-7-nitro-1,2,3,4-tetrahydronaphth-1-yl]Acetamide ((±)-8. ADL-01-0029-7)

ADL-01-0029-7 was prepared via the general DCC/pyr coupling method from (±)-2 (0.5790 15 g, 2.103 mmol), 2-nitro-4,5-dichlorophenylacetic acid (1.0512 g, 4.204 mmol), DCC (0.8948 g, 4.34 mmol), and pyr (0.35 mL, 4.3 mmol). After stirring at 25° C. overnight, more 2-nitro-4,5-dichlorophenylacetic acid (1.05 10 g, 4.203 mmol), DCC (0.8946 g, 4.34 mmol), and CH$_2$Cl$_2$ (10 mL) were added, and after 5 h, the reaction was worked up according to the general procedure. The crude product was purified by gravity column eluting with CH$_2$Cl$_2$:2% NH$_3$ before it was converted to the HCl salt with 1.0 M HCl in Et$_2$O and washed with hot MeOH to yield (±)-8:HCl (0.4948 g, 43% yield): m.p. (HCl salt) >250° C.; $^1$H NMR (HCl salt, DMSO-d$_6$) δ 61.8-2. (br s, 4H, —CH$_2$CH$_2$—), 2.2-4.6 (complex, 11H, 5 —CH$_2$— and 1 —CH—), 2.9 (s, 3H, —NCH$_3$), 6.1 (d, J=10.2 Hz, 1H, —CH—), 7.53 (d, J=8.5 Hz, 1H, aromatic), 7.89 (s, 1H, aromatic), 7.91 (s, 1H, aromatic), 8.12 (d of d, J=2.2 Hz and 8.5 Hz, 1H, aromatic), 8.4 (s, 1H, aromatic). MS (FAB) m/z 507. Anal. (C, H, N) C$_{23}$H$_{24}$N$_4$O$_5$Cl$_2$HCl.

EXAMPLE 37

2-(3,4-Dichlorophenyl)-N-methyl-N-[((±)-trans-2-(1-pyrrolidinyl)-7-nitro-1,2,3,4-tetrahydronaphth-1-yl]acetamide ((±)-9, ADL-01-0031-3)

ADL-01-0031-3 was prepared via the general DCC/pyr coupling procedure from (±)-2 (1.8173 g, 6.600 mmol), 3,4-dichlorophenylacetic acid (2.7066 g, 13.20 mmol), DCC (2.8057 g, 13.60 mmol), and pyr (1.10 mL, 13.6 mmol). The product was purified by flash column eluting with CH$_2$Cl$_2$: 2% NH$_3$:1% MeOH before it was converted to the HCl salt with Et$_2$O—HCl and washed with hot MeOH to yield (±)-9.HCl (2.49 g 76%): m.p. (HCl salt) 255-257° C.; $^1$H NMR (HCl salt, DMSO-d$_6$) 61.8-2 (br s, 4H, —CH$_2$CH$_2$-), 2-4.2 (complex, 11H, 5 —CH$_2$— and 1 —CH—), 2.83 (s, 3H, —NCH$_3$), 6.1 (d, J=9.8 Hz, 1H, —CH—), 7.3-7.7 (complex, 5H, aromatic), 8.06 (d of d, J=2.4 Hz and 8.6 Hz, 1H, aromatic). MS (FAB) m/z 462. Anal. (C, H, N) C$_{23}$H$_{25}$N$_3$O$_3$Cl$_2$HCl.

EXAMPLE 38

2-(3,4-Dichlorophenyl)-N-methyl-N-(t)-trans-2-(1-pyrrolidinyl)-7-amino-1,2,3,4-tetrahydronaphth-1-yl]acetamide ((±)-10, ADL-01-0032-1)

With stirring at 55° C., Raney nickel (50% slurry in H$_2$O) was added in small portions to a mixture of (±)-9 (2.10 g, 4.54 mmol) and hydrazine hydrate (4 mL) in EtOH (60 mL) until all hydrazine was decomposed in 30 mm. The mixture was filtered through celite, and the Raney nickel was washed with hot MeOH (120 mL). The filtrate was evaporated and dried in vacuo before the residue was partitioned between sat'd NaHCO$_3$ and CH$_2$Cl$_2$, which was dried (Na$_2$SO$_4$), filtered through celite, and evaporated. The product was purified by gravity column eluting with CHCl$_3$:2% NH$_3$: 0.5% MeOH before it was converted to the HCl salt with Et$_2$O—HCl to yield (±)-10.HCl (0.3 g, 14%, unoptimized): m.p. (HCl salt) >250° C.; $^1$H NMR (free base, CDCl$_3$) δ 1.64

(br s, 4H, —CH$_2$CH$_2$—), 1.9-3.8 (complex, 11H, 5—CH$_2$— and 1 —CH—), 2.59 (s, 3H, —NCH$_3$), 5.8 (d, J=9.7 Hz, 1H, —CH—), 6.29 (s, 1H, aromatic), 6.43 (d, J=8 Hz, 1H, aromatic), 6.8 (d, J=8 Hz, 1H, aromatic), 7.17 (d, J=8 Hz, 1H, aromatic), 7.3 (m, 2H, aromatic). MS (FAB) m/z 432. Anal. (C, H, N) C$_{23}$H$_{27}$N$_3$OCl$_2$.2HCl.

EXAMPLE 39

2-(4-Methylsulfonylphenyl)-N-methyl-N-[(±)-trans-2-(1-pyrrolidinyl)-7-nitro-1,2,3,4-tetrahydronaphth-1-yl]acetamide ((±)-11, ADL-01-0034-7)

ADL-01-0034-7 was prepared via the general DCC/pyr coupling procedure from (±)-2 (0.3414 g, 1.240 mmol), 4-methylsulfonylphenylacetic acid (0.5309 g, 2.478 mmol), DCC (0.5288 g, 2.563 mmol), and pyr (0.21 mL, 2.55 mmol). After stirring at 25° C. overnight, more of 4-methylsulfonylphenylacetic acid (0.5307 g, 2.477 mmol), DCC (1.1356 g, 5.504 mmol), and CH$_2$Cl$_2$ (13 mL) were added, and the mixture was worked up according to the general procedure after another night of stirring. The product was purified by gravity column eluting with CHCl$_3$:2% NH$_3$:1% MeOH before it was converted to the HCl salt with Et$_2$O—HCl and washed with hot MeOH to yield (±)-11.HCl (0.4455 g, 76%): m.p. (HCl salt) 284-285° C.; $^1$H NMR (HCl salt, DMSO-d$_6$) δ 1.96 (br s, 4H, —CH$_2$CH$_2$—), 2.1-4.3 (complex, 11H, 5 —CH$_2$— and 1 —CH—), 2.88 (s, 3H, —NCH$_3$), 3.24 (s, 3H, —SO$_2$CH$_3$), 6.13 (d, J=10 Hz, 1H, —CH—), 7.51 (d, J=8.8 Hz, 1H, aromatic), 7.68 (m, 3H, aromatic), 7.9 (d, J=8.7 Hz, 2H, aromatic), 8.08 (d of d, J=2.6 Hz and 8.5 Hz, 1H, aromatic). MS (FAB) m/z 472. Anal. (C, H, N) C$_{24}$H$_{29}$N$_3$O$_5$.HCl.0.25CH$_2$Cl$_2$.

EXAMPLE 40

2-(3,4-dichlorophenyl)-N-methyl-N-{[±]-trans-2-[1-pyrrolidinyl]-7-[N,N-bis-(t-butoxycarbonylmethyl)-amino]-1,2,3,4-tetrahydronaphth-1-yl}acetamide ((±)-12, ADL-01-0037-0)

With stirring in ice-H$_2$O under N$_2$, t-butyl bromoacetate (0.34 mL, 2.32 mmol) was added dropwise to a mixture of (±)-10 (0.4014 g, 0.928 mmol) and NEt(iPr)$_2$ (0.81 mL, 4.64 mmol) in dry THF (10 mL). After 10 mm, the mixture was stirred at 25° C. under N$_2$ overnight before more t-butyl bromoacetate (0.30 mL) was added at 25° C. After stirring overnight, more NEt(iPr)$_2$ (0.40 mL) and t-butyl bromoacetate (0.30 mL) were added, and after one more night of stirring, the mixture was partitioned between sat'd NaHCO$_3$ and CH$_2$Cl$_2$. The aqueous fraction was extracted with more CH$_2$Cl$_2$, and the combined organic fraction was dried (Na$_2$SO$_4$), filtered through celite, and evaporated. The crude product was purified by gravity column eluting with CH$_2$Cl$_2$:2% NH$_3$: 1% MeOH before part of the free base was converted to the HCl salt with 1.0 M HCl in Et$_2$O with stirring in ice-H$_2$O. The residue was sonicated in hexane to yield (±)-12.2HCl (0.1610 g, 25%, unoptimized): m.p. (HCl salt) 143° C. (dec); $^1$H NMR (free base, CDCl$_3$) δ 1.39 (s, 9H, t-butyl), 1.43 (s, 9H, t-butyl), 1.65 (br s, 4H, —CH$_2$CH$_2$—), 1.9-4.1 (complex, 15H, 7 —CH$_2$— and 1 —CH—), 2.58 (s, 3H, —NCH$_3$), 5.8 (m, 1H, —CH—), 6.2-7.4 (complex, 6H, aromatic). MS (FAB) 660. Anal. (C, H, N) C$_{35}$H$_{47}$N$_3$O$_5$Cl$_2$.2HCl.0.5CH$_3$CN.

EXAMPLE 41

2-(3.4-Dichlorophenyl)-N-methyl-N-{[±]-trans-2-[1-pyrrolidinyl]-7[N,N-bis-(carboxymethyl)amino]-1,2,3,4-tetrahydronaphth-1-yl}acetamide ((±)-13, ADL-01-0044-6)

A solution of (±)-12 (0.35 g, 0.5 mmol) in 1:1 AcOH and 3 N HCl (8 mL) with some anisole 10 (2 drops) was stirred at 25° C. overnight before conc. HCl (0.5 mL) was added, and the mixture was warmed to 40° C. for 1 h. Then some anisole (4 drops) was added, and the mixture was stirred at 25° C. for 5 h before it was evaporated. The residue was sequentially evaporated from iPrOH and PhCH$_3$ before it was sonicated with Et$_2$O to yield (±)-13.HCl (0.2360 g, 81%): m.p. (HCl salt) 160° C. (dec); $^1$H NMR (HCl salt, DM50-d$_5$) δ 1.93 (br s, 15 4H, —CH$_2$CH$_2$—), 2.2-4.3 (complex, 15H, 7—CH$_2$- and 1—CH—), 2.79 (s, 3H, —NCH$_3$—), 5.93 (d, J=10.7 Hz, 1H, —CH—), 6.37 (s, 1H, aromatic), 6.68 (d, J=8.8 Hz, 1H, aromatic), 7.00 (d, J=8.1 Hz, 1H, aromatic), 7.40 (d, J 8.1 Hz, 1H, aromatic), 7.63 (m, 2H, aromatic). MS (FAB) m/z 490 (M+1-CH$_2$CO$_2$H). Anal. (C, H, N) C$_{27}$H$_{31}$N$_3$O$_5$Cl$_2$.HCl.

EXAMPLE 42

2-(3,4-Dichlorophenyl)-N-methyl-N-{[±]-trans-2-[1-pyrrolidinyl]-7-[N,N-bis-(ethoxycarbonylmethyl)-amino]-1,2,3,4, tetrahydronaphth-1-yl}acetamide ((±)-14, ADL-01-0052-9)

With stirring in ice-H$_2$O under N$_2$, ethyl bromoacetate (0.47 mL, 4.21 mmol) was added dropwise to a mixture of (±)-10 (0.3640 g, 0.842 mmol) and NEt(iPr)$_2$ (0.88 mL, 5.05 mmol) in dry THF (6 mL). After 10 mm, the mixture was stirred at 25° C. under N$_2$ overnight before it was partitioned between sat'd NaHCO$_3$ and CH$_2$Cl$_2$. The aqueous fraction was extracted with more CH$_2$Cl$_2$, and the combined organic fraction was dried (Na$_2$SO$_4$), filtered through celite, and evaporated. The product was purified by gravity column eluting with CH$_2$Cl$_2$:2% NH$_3$:1% MeOH before it was converted to the HCl salt with 1.0 M HCl in Et$_2$O and washed with Et$_2$O to yield (±)-14HCl (0.27 g, 47%): m.p. (HCl salt) 128° C. (dec); $^1$H NMR (HCl salt, DMSOd$_6$) δ 1.2 (m, 6H, 2 —CH$_3$), 1.9 (br s, 4H, —CH$_2$CH$_2$—), 2.2-4.4 (complex, 19H, 9-CH$_2$— and 1 —CH—), 2.78 (s, 3H, —NCH$_3$), 5.9 (d, J=10.3 Hz, 1H, —CH—), 6.14 (s, 1H, aromatic), 6.49 (d, J=8.2 Hz, 1H, aromatic), 6.91 (d, J=8.3 Hz, 1H, aromatic), 7.39 (d, J=8.3 Hz, 1H, aromatic), 7.6 (m, 2H, aromatic). MS (FAB) m/z 605. Anal. (C, H, N) C$_{31}$H$_{39}$N$_3$O$_5$Cl$_2$.1.25HCl.0.3CH$_3$CN.

EXAMPLE 43

2-(3,4-Dichlorophenyl)-N-methyl-N-[(±)-trans-2-(1-pyrrolidin-7-(N-diethylphosphoramidato-amino)-1,2,3,4-tetrahydronaphth-1-yl]acetamide ((±)-15 ADL-01-0053-7)

With stirring in ice-H$_2$O under N$_2$, diethyl chlorophosphate (0.57 mL, 3.92 mmol) was added dropwise to a mixture of (±)-10 (0.3393 g, 0.785 mmol) and NEt(iPr)2 (0.82 mL, 4.71 mmol) in dry THF (6 mL). After 10 mm, the mixture was stirred at 25° C. under N$_2$ overnight before the mixture was evaporated and dried in vacuo. The residue was partitioned between sat'd NaHCO$_3$ and CH$_2$Cl$_2$. The aqueous fraction was extracted with more CH$_2$Cl$_2$, and the combined organic fraction was dried ($Na_2SO_4$), filtered through ceite, and evaporated. The product was purified by gravity column eluting with $CH_2Cl_2$:2% $NH_3$:1.5% MeOH before it was converted to the HCl salt with 1.0 M HCl in $Et_2O$ and sonicated in $Et_2O$ to yield (±)-15HCl (0.4205 g, 89%): m.p. (HCl salt) 247-249° C.; $^1H$ NMR (HCl salt, DMSO-$d_6$) δ 1.2 (m, 6H, 2 —$CH_3$), 1.95 (br s, 4H, —$CH_2CH_2$-), 2.24.1 (complex, 15H, 7 —$CH_2$— and 1 —CH—), 2.75 (s, 3H, —$NCH_3$), 5.98 (d, J=10.3 Hz, 1H, —CH—), 6.7 (s, 1H, aromatic), 6.9 (m, 1H, aromatic), 7.03 (d, J=8.4 Hz, 1H, aromatic), 7.3 (d of d, J=2 Hz and 8.2 Hz, 1H, aromatic), 7.6 (m, 2H, aromatic), 7.92 (d, J=9.7 Hz, —NHP). MS (FAB) m/z 568. Anal. (C, H, N) $C_{27}H_{36}N_3O_4PCl_2$.HCl.0.25$H_2O$.

EXAMPLE 44

2-(3,4-Dichlorophenyl)-N-methyl-N-{[±]-trans-2-[1-pyrrolidinyl]-7-[N-2-(diethylphosphoryl)ethylamino]-1,2,3,4-tetrahydronaphth-1-yl}acetamide ((±)-16, ADL-01-0070-1)

With stirring in ice-$H_2O$ under $N_2$, diethyl 2-bromoethylphosphonate (0.8601 g, 3.52 mmol) was added to a mixture of (±)-10 (0.3042 g, 0.704 mmol) and NEt(iPr)$_2$ (0.74 mL, 4.2 mmol) in dry THF (4 mL). After 10 min., the mixture was stirred at 25° C. under $N_2$ for 2.5 days 20 before more diethyl 2-bromoethylphosphonate (0.8546 g) and NEt(iPr)$_2$ (0.74 mL, 4.2 mmol) were added. After stirring for 14 more days, the mixture was evaporated to dryness and dried in vacuo before the residue was partitioned between sat'd $NaHCO_3$ and $CH_2Cl_2$. The aqueous fraction was extracted with more $CH_2Cl_2$, and the combined organic fraction was dried ($Na_2SO_4$), filtered through celite, and evaporated. The product was purified by gravity column eluting with $CH_2Cl_2$:2% $NH_3$:1% MeOH and then by radial chromatography eluting with $CH_2Cl_2$:2% $NH_3$. The product was converted to the HCl salt with. 1.0 M HCl in $Et_2O$ and solidified by evaporation from $CH_2Cl_2$ and sonication with $EtO_2$ to yield (±)-16.HCl (0.2466 g, 52%): m.p. (HCl salt) 151° C. (dec); $^1H$ NMR (HCl salt, DMSO-$d_6$) δ 1.24 (t. J 7 Hz, 6H, 2 —Cl—I$_3$), 1.93 (br s, 4H, —$CH_2CH_2$—), 2-4.3 (complex, 19H, 9 —$CH_2$— and 1 —CH—), 2.8 (s, 3H, $NCH_3$), 5.96 (d, J=10.2 Hz, 1H, —CH—), 6.69 (br s, 1H, aromatic), 6.87 (d, J=7.5 Hz, 1H, aromatic), 7.11 (d, J=8.1 Hz, 1H, aromatic), 7.43 (d, J=8.3 Hz, 1H, aromatic), 7.64 (m. 2H, aromatic). MS (FAB) m/z 596. Anal. (C, H, N) $C_{29}H_{40}N_3O_4PCl_2$2HCl.

EXAMPLE 45

2-(3,4-Dichlorophenyl)-N-methyl-N-{(±)-trans-2-(1-pyrrolidinyl)-6-methoxy-7-(N-benzyl-N-methylaminosulfonyl)-1,2,3,4-tetrahydronaphth-1-yl]acetamide ((±)-19, ADL 01-0090-9)

ADL-01-0090-9 was prepared via the general DCC/pyr coupling procedure from (±)-17 (0.6213 g, 1.40 mmol), 3,4-dichlorophenylacetic acid (0.5764 g, 2.81 mmol), DCC (0.595 1 g, 2.88 mmol), and pyr (0.23 mL, 2.88 mmol). The product was gravity column chromatographed eluting with $CH_2Cl_2$:2% $NH_3$:1% MeOH and further purified by radial chromatography eluting with $CH_2Cl_2$:2% $NH_3$. The product was converted to the HCl salt with 1.0 M HCl in $Et_2O$ to yield (±)-19HCl (0.3 g, 32%): m.p. (HCl salt) 150° C. (dec); $^1H$ NMR (HCl salt, DMSO-$d_6$) 6 191 (br s, 41-1, —$CH_2CH_2$—), 2.2 4.1 (complex, 11H, 5 —$CH_2$— and 1 —CH—), 2.55 (s, 3H, —$NCH_3$), 2.77 (s, 3H, —$NCH_3$), 3.88 (s, 3H, —$OCH_3$), 4.2 (s, 2H, —$CH_2Ph$), 6.0 (d, J=9.7 Hz, 1H, —CH—), 7.10 (s, 1H, aromatic), 7.2-7.4 (complex, 7H, aromatic), 7.55 (m, 2H, aromatic). MS (FAB) m/z 630. Anal. (C, H, N) $C_{32}H_{37}N_3O_4Cl_2S$.HCl.0.5$H_2O$.

EXAMPLE 46

2-(3,4-Dichlorophenyl)-N-methyl-N-{(±)-trans-2-(1-Pyrrolidinyl)-7-(N-benzyl-N-methylaminosulfonyl)-1,2,3,4-tetrahydronaphth-1-yl]acetamide ((±)-20, ADL-01-0099-0)

ADL-01-0099-0 was prepared via the general DCC/pyr coupling procedure from (±)-18 (0.4530 g, 1.095 mmol), 3,4-dichlorophenylacetic acid (0.4485 g, 2.19 mmol), DCC (0.4677 g, 2.27 mmol), and pyr (0.18 mL, 2.26 mmol). The product was purified by flash column eluting with $CH_2Cl_2$: 2% $NH_3$ and then by radial chromatography eluting with $CH_2Cl_2$:2% $NH_3$. The product was converted to the HCl salt with 1.0 M HCl in $Et_2O$ and then washed with hot MeOH to yield (±)-20.HCl (0.33 g, 47%): m.p. (HCl salt) 25 1-254° C.; 1H NMR (HCl salt, DMSO-$d_6$) δ 1.97 (br s, 4H, —$CH_2CH_2$-), 2.34.2 (complex, 13H, 6 —$CH_2$— and 1 —CH—), 2.49 (s, 3H, —$NCH_3$), 2.90 (s, 3H, —$NCH_3$), 6.17 (d, J=10.4 Hz, 1H, —CH—), 7.2-7.8 (complex, 11H, aromatic). MS (FAB) m/z 600. Anal. (C, H, N) $C_{31}$, $H_{35}N_3SO_3Cl_2$.HCl.

EXAMPLE 47

2-(2-Nitro.4,5-dichlorophenyl)-N-methyl-N-[(±)-trans-2-(1-pyrrolidinyl)-indan-1-yl]acetamide ((±)-24, ADL-01-0104-8)

ADL-01-0104-8 was prepared via the general DCC/pyr coupling procedure from (±)-23 (0.4265 g, 1.97 1 mmol), 2-nitro-4,5-dichlorophenylacetic acid (0.9859 g, 3.943 mmol), DCC (0.8350 g, 4.047 mmol), and pyr (0.33 mL, 4.06 mmol). The crude product was purified by silica gel column eluting with $CH_2Cl_2$:2% $NH_3$ before it was converted to the HCl salt with 1.0 M HCl in $Et_2O$ and crystallized from MeOH to yield (±)-24HCl (0.3630 g, 38%, first crop): m.p. (HCl salt) 284-287° C.; 1H NMR (HCl salt, DM50-$d_6$) δ 1.8-2.1 (br s, 4H, —$CH_2CH_2$—), 2.84 (s, 3H, —$NCH_3$), 3-4.4 (complex, 9H, 4 —$CH_2$— and 1 —CH—), 6.37 (d, J=8 Hz, 1H, —CH30), 7.08 (br s, 1H, aromatic), 7.3 (m, 3H, aromatic), 7.92 (s, 1H, aromatic), 8.41 (s, 1H, aromatic). MS (FAB) m/z 448. Anal. (C, H, N) $C_{22}H_{23}N_3O_3Cl_2$.HCl.

EXAMPLE 48

2-(2-Nitro-1-trifluoromethylphenyl)-N-methyl-N-[(±)-trans-2-(1-pyrrolidinyl)-indan-1-yl]acetamide ((±)-26, ADL-01-0106-3)

ADL-01-0106-3 was prepared via the general DCC/pyr coupling procedure from (±)-23 (0.3229 g, 1.492 mmol), 2-nitro-4-trifluoromethylphenylacetic acid (0.5579 g, 2.24 mmol), DCC (0.5512 g, 2.67 mmol), and pyr (0.19 mL, 2.31 mmol). The crude product was gravity column chromatographed eluting with $CH_2Cl_2$:2% $NH_3$ before it was converted to the HCl salt with 1.0 M HCl in $Et_2O$ and crystallized from MeOH-$Et_2O$ to yield (±)-26HCl (0.3643 g, 50%): m.p. (HCl salt) 249-250° C.; $^1$H NMR (HCl salt, DMSO-$d_6$) δ 1.8-2.1 (br s, 4H, —$CH_2CH_2$—), 2.89 (s, 3H, —$NCH_3$), 34.6 (complex, 9H, 4 —$CH_2$— and 1 —CH—), 6.40 (d, J=8.1 Hz, 1H, —CH—), 7.1 (br s, 1H, aromatic), 7.3 (m, 3H, aromatic), 7.83 (d, J=8.1 Hz, 1H, aromatic), 8.17 (d, J=7.8 Hz, 1H, aromatic), 8.41 (s, 1H, aromatic). MS (FAB) m/z 448. Anal. (C, H, N) $C_{23}H_{24}N_3O_3F_3$·HCl.

EXAMPLE 49

2,2-Diphenyl-N-methyl-N-[(±)-trans-2-(1-pyrrolidinyl)-indan-1-yl]acetamide ((±)-28, ADL-01-0108-9)

ADL-01-108-9 was prepared via the general DCC/pyr coupling procedure from (±)-23 (0.2615 g, 1.209 mmol), diphenylacetic acid (0.5123 g, 2.41 mmol), DCC (0.5138 g, 2.49 mmol), and pyr (0.20 mL, 2.5 mmol). The crude product was purified by gravity column eluting with $CH_2Cl_2$:2% $NH_3$ before it was converted to the HCl salt with 1.0 M HCl in $Et_2O$ and crystallized from MeOH to yield (±)-28HCl (0.38 15 g, 7 1%): m.p. (HCl salt) >300° C.; $^1$H NMR (HCl salt, DMSO-$d_6$; the cis-trans rotamers are observed in about 3.6 to 1 ratio. Only peaks for the major rotamer are reported.) δ 1.88 (br s, 4H, —$CH_2CH_2$-), 2.75 (s, 3H, —$NCH_3$), 3-4.2 (complex, 7H, 3 —$CH_2$— and 1 —CH—), 5.61 (s, 1H, —CH—), 6.5 (d, J=8 Hz, 1H, —CH—), 6.88 (d, J=6.5 Hz, 1H, aromatic), 7.1-7.4 (complex, 13H, aromatic). MS (FAB) m/z 411. Anal. (C, H, N) $C_{28}H_{30}N_2O$·HCl·0.75 $H_2O$.

EXAMPLE 50

2-(4-Methylsulfonylphenyl)-N-methyl-N-[(±)-trans-2-(1-pyrrolidinyl)-indan-1-yl]acetamide ((±)-29, ADL-01-0109-7)

ADL-01-0 109-7 was prepared via the general DCC/pyr coupling procedure from (±)-23 (0.3271 g, 1.51 mmol), 4-methylsulfonylphenylacetic acid (0.6464 g, 3.017 mmol), DCC (0.6438, 3.12 mmol), and pyr (0.25 mL, 3.1 mmol). The product was purified by gravity 25 column eluting with $CH_2Cl_2$:2% $NH_3$ before it was converted to the HCl salt with 1.0 M HCl in $Et_2O$ and crystallized from MeOH-$Et_2O$ to yield (±)-29HCl (0.5295 g, 78%): m.p. (HCl salt) 246-248° C.; $^1$H NMR (HCl salt, DMSO-$d_6$) δ 1.8-2 (br s, 4H, —$CH_2Cl_2$—), 2.81 (s, 3H, —$NCH_3$), 2.9-4.2 (complex, 9H, 4 —$CH_2$— and 1 —CH—), 3.21 (s, 3H, —$SO_2CH_3$), 6.4 (d, J=8.1 Hz, 1H, —CH—), 7 (m, 1H, aromatic), 7.3 (m, 3H, aromatic), 7.58 (d, J=8.1 Hz, 2H, aromatic), 7.9 (d, J=7.8 Hz, 2H, aromatic). MS (FAB) m/z 413. Anal. (C, H, N) $C_{22}H_{28}N_2SO_3$·HCl·0.25$H_2O$.

Compounds of Formula III

Compounds having the following structrues were prepared.

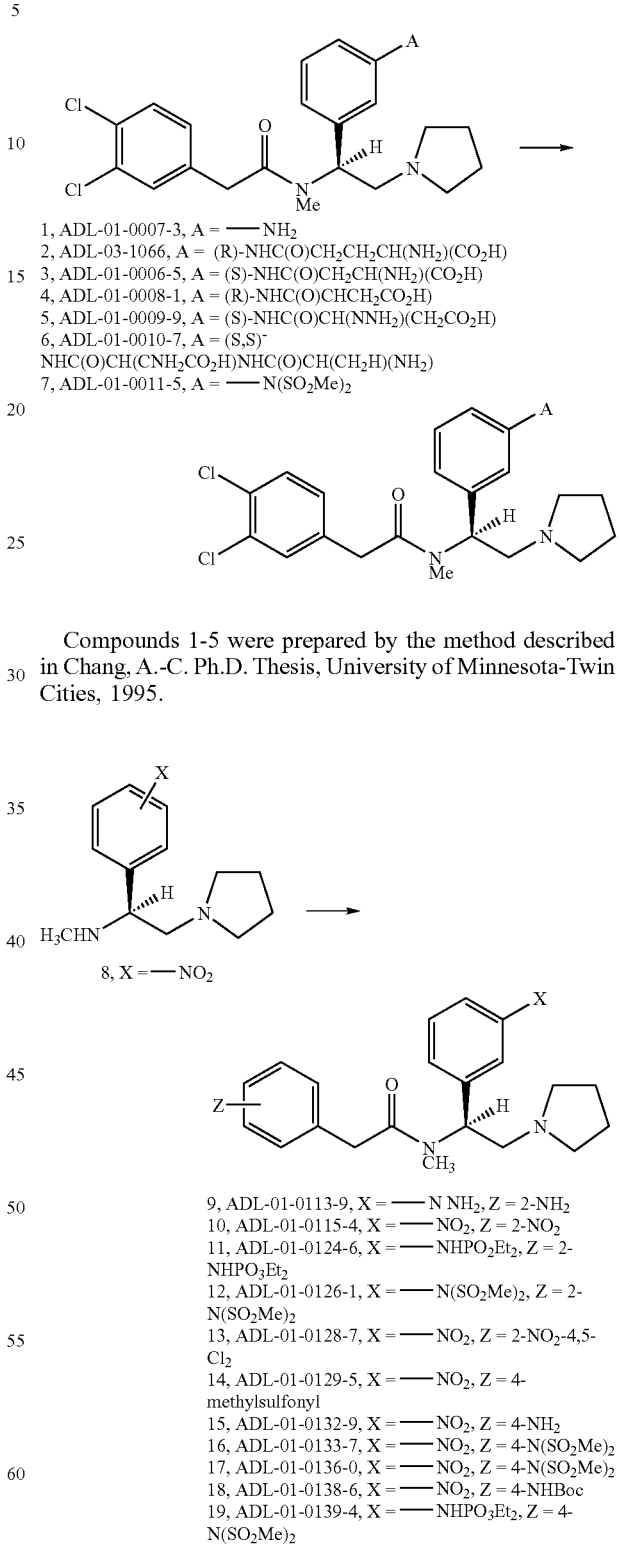

Compounds 1-5 were prepared by the method described in Chang, A.-C. Ph.D. Thesis, University of Minnesota-Twin Cities, 1995.

Compounds 9-19 were prepared from the appropriate arylacetic acids via DCC/pyr coupling, followed by reduction, deprotection, and/or derivatization via known chemistry. Intermediate 8 was prepared via the method described in Chang, A.-C. Ph.D. Thesis, University of Minnesota-Twin Cities, 1995.

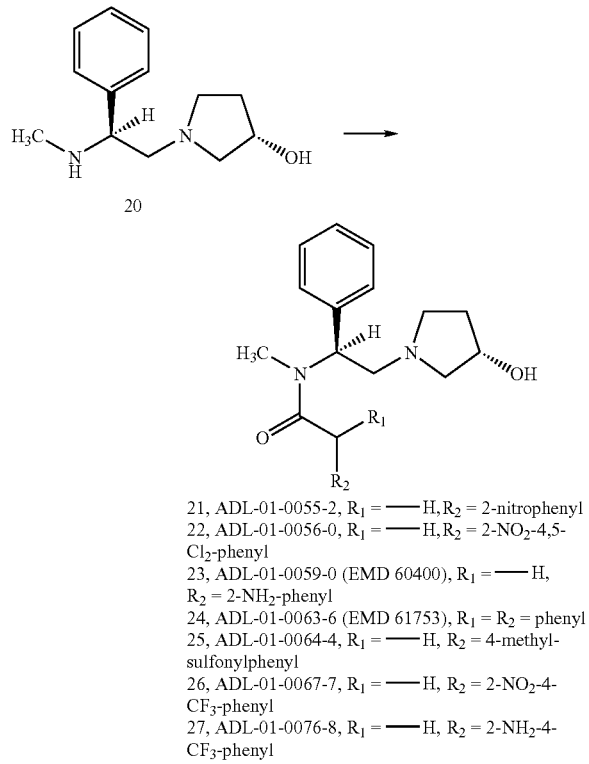

21, ADL-01-0055-2, R$_1$ = ——H, R$_2$ = 2-nitrophenyl
22, ADL-01-0056-0, R$_1$ = ——H, R$_2$ = 2-NO$_2$-4,5-Cl$_2$-phenyl
23, ADL-01-0059-0 (EMD 60400), R$_1$ = —— H, R$_2$ = 2-NH$_2$-phenyl
24, ADL-01-0063-6 (EMD 61753), R$_1$ = R$_2$ = phenyl
25, ADL-01-0064-4, R$_1$ = ——H, R$_2$ = 4-methyl-sulfonylphenyl
26, ADL-01-0067-7, R$_1$ = ——H, R$_2$ = 2-NO$_2$-4-CF$_3$-phenyl
27, ADL-01-0076-8, R$_1$ = ——H, R$_2$ = 2-NH$_2$-4-CF$_3$-phenyl Intermediate 20 was prepared via minor modifications of known methods.[7,8] Compounds 23 (EMD 60400) and 24 (EMD 61753) are known compounds that were synthesized in-house via minor modifications of reported methods.[9] Compounds 21, 22 and 25-27 were prepared by DCC coupling, following by reduction where applicable.

Ref.
(7) Costello, G. F. et al., J. Med. Chem. 1991, 34, 181-189.
(8) Naylor, A. et al., J. Med. Chem. 1994, 37, 2138-2144.
(9) Gottschlich, R. et al., Bioorg. Med. Chem. Letters 1994, 4, 677-682.

EXAMPLE 51

2-(3,4-Dichlorophenyl)-N-methyl-N-{[IS-1-[N-(S-aspartic Acid-a-amide-S-aspartic Acid-α-amido)-3-aminophenyl]-2-[1-pyrrolidinyl]ethyl}acetamide (6, ADL-01-0010-7)

With stirring in ice-H$_2$O under N$_2$, 1,3-dicyclohexylcarbodiimide (DCC, 0.353 g, 1.711 mmol) and dry CH$_2$Cl$_2$ (2 mL) were added to a mixture of 5-t-butyl ester (0.311 g, 0.538 mmol), N-Boc-L-aspartic acid-β-t-butyl ester (0.495 g, 1.711 mmol), and 1-hydroxybenzotriazole (HOBT, 0.232 g, 1.7 17 mmol) in dry CH$_2$Cl$_2$ (8 mL). After 5 min, the mixture was stirred at 25° C. under N$_2$ overnight before H$_2$O (1 mL) was added, and the mixture was filtered through celite. The 1,3-dicyclohexylurea (DCU) was washed with CH$_2$Cl$_2$ (18 mL). The filtrate was partitioned between sat'd NaHCO$_3$ and CH$_2$Cl$_2$, which was dried (Na$_2$SO$_4$), filtered through celite, and evaporated. After flash column chromatography eluting with CH$_2$Cl$_2$:2% NH$_3$:2% MeOH, the protected intermediate (0.411 g, 90%) was dissolved in 3N HCl (4 mL), AcOH (4 mL) with anisole (2 drops), and stirred at 25° C. overnight. The mixture was then evaporated to dryness, and evaporation from iPrOH then yielded ADL-01-0010-7: $^1$H NMR (HCl salt, DMSO-d$_6$) δ 2.0 (br s, 4H, —CH$_2$CH$_2$—), 2.9 (s, 3H, —NCH$_3$), 6.1 (br m, 1H, —CH—). MS (FAB) m/z 636. Anal. (C, H, N) C$_{29}$H$_{35}$N$_5$O$_7$Cl$_2$.1.5HCl.0.25iPrOH.

EXAMPLE 52

2-(3,4-Dichlorophenyl)-N-methyl-N-{[1S]-1-[N-(bis-methylsulfonamido)-3-aminophenyl]-2-[1-pyrrolidinyl]ethyl}acetamide (7, ADL-01-001 1-5)

With stirring at 25° C., a solution of methanesulfonyl chloride (MsCl. 0.25 mL, 3.2 mmol) in dry CH$_2$Cl$_2$ (0.75 mL) was added to a mixture of ADL-01-0007-3 (0.225 g, 0.554 mmol) and Et$_3$N (1 mL, 7 mmol) in dry CH$_2$Cl$_2$ (4 mL), and the mixture was stirred at 25° C. fitted with a drying tube. After 5 h, more CH$_2$Cl$_2$ (6 mL), MsCl (0.5 mL), and Et$_3$N (2 mL) were added, and the mixture was stirred at 25° C. overnight before it was partitioned between CH$_2$Cl$_2$ (50 mL) and sat'd NaHCO$_3$. The aqueous fraction was extracted with more CH$_2$Cl$_2$ (25 mL), and the combined organic fraction was dried (Na$_2$SO$_4$), filtered through celite, and evaporated. Acetonitrile was used to azeotrope off Et$_3$N before the product was gravity column chromatographed twice eluting with CH$_2$Cl$_2$:2% NH$_3$:2% MeOH. The pure product was then treated with 1.0 M HCl in Et$_2$O to yield 7.HCl (0.131 g, 39%, unoptimized): m.p. (HCl salt) 145° C. (dec); $^1$H NMR (free base, CDCl$_3$) δ 1.7 (br s, 4H, —CH$_2$CH$_2$-), 2.4-3.8 (complex, 8H, 4 —CH$_2$-), 2.7 (s, 3H, —NCH$_3$), 3.37 (s, 6H, 2-SO$_2$CH$_3$), 6.1 (m, 1H, —CH—), 7.1-7.4 (complex, 7H, aromatic). MS (FAB) n/z 562. Anal. (C, H, N) C$_{23}$H$_{29}$N$_3$O$_5$S$_2$Cl$_2$.HCl.0.75H$_2$O.

EXAMPLE 53

2-(2-Nitrophenyl)-N-methyl-N-[(1S)-1-(3-nitrophenyl)-2-(1-pyrrolidinyl)ethyl]acetamide (10, ADL-01-0115-4)

ADL-01-01 154 was prepared via the general DCC/pyr coupling procedure from 8 (1.4886 g, 5.97 mmol), 2-nitrophenylacetic acid (2.1619 g, 11.93 mmol), DCC (2.5402 g, 12.31 mmol), and pyridine (1.00 mL, 12.36 mmol). The crude product was converted to the HCl salt with Et$_2$O-HCl without chromatography and crystallized from MeOH-Et$_2$O. The first crop was recrystallized again from MeOH-Et$_2$O to yield 10HCl (1.3663 g, 51%): m.p. (HCl salt) 258-259° C.; $^1$H NMR (HCl salt, DMSO-d$_6$) δ 1.97 (br s, 4H, —CH$_2$CH$_2$—), 2.91 (s, 3H, —NCH$_3$), 3.11-4.45 (complex, 8H, 4 —CH$_2$-), 6.17 (m, 1H, —CH—), 7.51-8.25 (complex, 8H, aromatic). MS (FAB) m/z 413. Anal. (C, H, N) C$_{21}$H$_{24}$N$_4$O$_5$.HCl.0.25H$_2$O.

EXAMPLE 54

2-(2-Aminophenyl)-N-methyl-N-[(1S)-1-(3-aminophenyl)-2-(1-pyrrolidinyl)ethyl]acetamide (9, ADL-01-01 13-9)

With stirring at 55° C., Raney nickel was added in small quantities to a mixture of 10 (0.9857 g, 2.3899 mmol) and hydrazine hydrate (55%, 2 mL) in EtOH (30 mL) until gas evolution stopped in about 10 min. The mixture was then filtered through celite, and the Raney nickel was washed with hot MeOH (100 mL). The filtrate was evaporated and dried in vacuo before the residue was partitioned between sat'd NaHCO$_3$ and CH$_2$Cl$_2$, which was dried (Na$_2$SO$_4$), filtered through celite, and evaporated. The product was gravity column chromatographed eluting with CHCl$_3$:2% NH$_3$:2% MeOH before it was converted to the HCl salt with Et$_2$O—HCl to yield 9-3HCl (0.3 159 g, 29%, unoptimized): m.p. (HCl salt) 219-222° C. $^1$H NMR (HCl salt, DMSO-d$_6$) δ 1.98 (br s, 4H, —CH$_2$CH$_2$—), 2.87 (s. 3H, —NCH$_3$), 3.2-4.3 (complex, 8H, 4 —CH$_2$—), 6.1 (m, 1H, —CH—), 7.11-7.45 (complex, 8H, aromatic). MS (FAB) m/z 353. Anal. (C, H, N) C$_{21}$H$_{28}$N$_4$O.$_3$HCl.0.25H$_2$O.

EXAMPLE 55

2-(N-Diethyl phosphoramidate-2-aminophenyl)-N-methyl-N-[(1S)-1-(N-diethyl phosphoramidate-3-aminophenyl)-2-(1-pyrrolidinyl)ethyl]acetamide (11 ADL-01-0124-6)

With stirring in ice-H$_2$O under N$_2$, diethyl chlorophosphate (0.53 mL, 3.67 mmol) was added to a mixture of 9 (0.2394 g, 0.6792 mmol) and NEt(iPr)$_2$ (0.77 mL, 4.40 mmol) in dry THF (5 mL). After 10 min, the mixture was stirred at 25° C. under N$_2$ for 3.5 days before it was diluted with CH$_2$Cl$_2$, evaporated, and dried in vacuo. The residue was partitioned between sat'd NaHCO$_3$ and CH$_2$Cl$_2$. The aqueous fraction was extracted with more CH$_2$Cl$_2$, and the combined organic fraction was dried (Na$_2$SO$_4$), filtered through celite, and evaporated. The product was chromatographed eluting with CH$_2$Cl$_2$:2% NH$_3$:2% MeOH before it was converted to the HCl salt with 1.0 M HCl in Et$_2$O and crystallized from iPrOH-Et$_2$O to yield 11-HCl (0.2364 g, 53%): m.p. (HCl salt) 184-186° C.; $^1$H NMR (HCl salt, DMSO-d$_6$) δ 1.2 (m, 12H, 4 —CH$_3$), 1.96 (br s, 4H, —CH$_2$CH$_2$-), 2.81 (s, 3H, —NCH$_3$), 34 (complex, 16H, 8 —CH$_2$—), 6.05 (m, 1H, —CH—), 6.7-7.3 (complex, 9H, aromatic and 1 NH), 8.08 (d, J=9.4 Hz, 1H, NHP). MS (FAB) m/z 625. Anal. (C, H, N) C$_{29}$H$_{46}$N$_4$O$_7$P$_4$.HCl.

EXAMPLE 56

2-(N-Bis-sulfonamido-2-aminophenyl)-N-methyl-N-[(1S)-1-(N-bis-sulfonamido-3-aminophenyl)-2-(1-pyrrolidinyl)ethyl]acetamide (12, ADL-01-0126-1)

With stirring at 0° C. under N$_2$, MsCl (0.61 mL, 7.87 mmol) was added to a mixture of 9 (0.2774 g, 0.787 mmol) and Et$_3$N (2.2 mL, 15.7 mmol) in CH$_2$Cl$_2$ (8 mL). After 10-15 mm, the mixture was stirred at 25° C. under N$_2$ overnight before the mixture was partitioned between sat'd NaHCO$_3$ and CH$_2$Cl$_2$. The aqueous fraction was extracted with more CH$_2$Cl$_2$, and the combined organic fraction was dried (Na$_2$SO$_4$), filtered through celite, and evaporated. Acetonitrile was added to azeotrope off Et$_3$N. The product was flash-column chromatographed eluting with CH$_2$Cl$_2$: 2% NH$_3$ before it was converted to the HCl salt with 1.0 M HCl in Et$_2$O to yield 12-HCl (0.3564 g, 65%): m.p. (HCl salt) 180° C.; $^1$H NMR (HCl salt, DMSO-d$_6$) δ 2.0 (br s, 4H, —CH$_2$CH$_2$—), 2.76 (s, 3H, —NCH$_3$), 34.3 (complex, 8H, 4 —CH$_2$—), 3.53 (s, 12H, 4 —SO$_2$CH$_3$), 6.25 (m, 1H, —CH—), 7.3-7.6 (complex, 8H, aromatic). MS (FAB) m/z 665. Anal. (C, H, N) C$_{25}$H$_{36}$N$_4$O$_9$S$_4$.HCl.MeOH.

EXAMPLE 57

2-(2-Nitro-4,5-dichlorophenyl)-N-methyl-N-[(1S)-1-(3-nitrophenyl)-2-(1-pyrrolidinyl)ethyl]acetamide (13. ADL-01-0128-7)

ADL-01-0128-7 was prepared via the general DCC/pyr coupling procedure from 8 (0.3690 g, 1.4801 mmol), 2-nitro-4,5-dichlorophenylacetic acid (0.7301 g, 2.920 mmol), DCC (0.6213 g, 3.01 mmol), and pyridine (0.24 mL, 3.01 mmol). The crude product was converted to the HCl salt with Et$_2$O-HCl without chromatography and crystallized from MeOH to yield 13HCl (0.3232 g, 42%): m.p. (HCl salt) 165° C. (dec); $^1$H NMR (HCl salt, DMSO-d$_6$) δ 2.0 (br s, 4H, —CH$_2$CH$_2$—), 2.93 (s, 3H, —NCH$_3$), 3.1-4.3 (complex, 6H, 3 —CH$_2$—), 4.4 (s, 2H, benzylic methylene), 6.2 (m, 1H, —CH—), 7.7-7.8 (m, 2H, aromatic), 7.9 (s, 1H, aromatic), 8.14 (s, 1H, aromatic), 8.27 (d, J=7.7 Hz, 1H, aromatic), 8.43 (s, 1H, aromatic). MS (FAB) m/z 481. Anal. (C, H, N) C$_{21}$H$_{22}$N$_4$O$_5$Cl$_2$.HCl0.5MeOH.

EXAMPLE 58

2-(4-Methylsulfonylphenyl)-N-methyl-N-[(1S)-1-(3-nitrophenyl)-2-(1-pyrrolidinyl)ethyl]acetamide (14, ADL-01-0129-5)

ADL-01-0129-5 was prepared via the general DCC/pyr coupling procedure from 8 (0.5138 g, 2.061 mmol), 4-methylsulfonylphenylacetic acid (0.8825 g, 4.119 mmol), DCC (0.8771 g, 4.251 mmol), and pyridine (0.34 mL, 4.245 mmol). The crude product was gravity column chromatographed eluting with CHCl$_3$:2% NH$_3$ before it was converted to the HCl salt with 1.0 M HCl in Et$_2$O and crystallized from MeOH to yield 14-HCl (0.4695 g, 47%): m.p. (HCl salt) 276-277° C.; $^1$H NMR (HCl salt, DMSO-d$_6$) δ 2.0 (br s, 4H, —CH$_2$CH$_2$—), 2.92 (s, 3H, —NCH$_3$), 3.2 (s, 3H, —SO$_2$CH$_3$), 3.24.3 (complex, 8H, 4 —CH$_2$—), 6.25 (m, 1H, —CH—), 7.61 (d, J=7.2 Hz, 2H, aromatic), 7.75 (m, 2H, aromatic), 7.89 (d, J=7 Hz, 2H, aromatic), 8.12 (s, 1H, aromatic), 8.25 (m, 1H, aromatic). MS (FAB) m/z 446. Anal. (C, H, N) C$_{22}$H$_{27}$N$_3$O$_5$S.HCl.

EXAMPLE 59

2-(N-Butyloxycarbonyl-4-aminophenyl)-N-methyl-N-[(1S)-1-(3-nitrophenyl)-2-(1-pyrrolidinyl)ethyl]acetamide (18, ADL-01-0138-6)

ADL-01-0138-6 was prepared via the general DCC/pyr coupling method from 8 (1.9948 g, 8.001 mmol), N-Boc-4-aminophenylacetic acid (3.0589 g, 12.173 mmol), DCC (2.6602 g, 12.89 mmol), and pyridine (1.04 mL, 12.9 mmol). The crude product was gravity column chromatographed eluting with CH$_2$Cl$_2$:2% NH$_3$:1% MeOH before it was converted to the HCl salt with 1.0 M HCl in Et$_2$O and crystallized from MeOH to yield 18HCl (0.489 1 g, 12%, first crop): m.p. (HCl salt) 170° C. (dec); $^1$H NMR (HCl salt, DMSO-d$_6$) δ 1.49 (s, 9H, t-butyl), 2.01 (br s, 4H, —CH$_2$CH$_2$—), 2.83 (s, 3H, —NCH$_3$), 3.14.15 (complex, 8H, 4 —CH$_2$—), 6.27 (m, 1H, —CH—), 7.17 (d, J=8 Hz, 2H, aromatic), 7.39 (d, J=8 Hz, 2H, aromatic), 7.7 (m, 2H, aromatic), 8.09 (s, 1H, aromatic), 8.23 (d, J=6 Hz, 1H, aromatic), 9.3 (s, 1H,-35 NHBoc). MS (FAB) 483. Anal. (C, H, N) C26H34N$_4$O$_5$.HCl.0.25 H$_2$O.

EXAMPLE 60

2-(4-Aminophenyl)-N-methyl-N-[(1S)-1-(3-nitrophenyl)-2-(1-pyrrolidinyl)ethyl]acetamide (15, ADL-01-0132-9)

ADL-01-0138-6 (2.9211 g, 6.053 mmol) and anisole (2 drops) were mixed in AcOH (10 mL) and 4N HCl (10 mL) and stirred at 25° C. overnight, fitted with a drying tube. The mixture was adjusted to pH 13 with 1 N NaOH with stirring in ice-$H_2O$ and then extracted with $CH_2Cl_2$ (2×70 mL). The combined organic fraction was dried ($Na_2SO_4$), filtered through celite, and evaporated. The product was gravity column chromatographed eluting with $CHCl_3$:2% $NH_3$ before it was converted to the HCl salt with $Et_2O$—HCl to yield 15-HCl (0.5531 g, 22%, unoptimized): m.p. (HCl salt) 200° C. (dec); $^1H$ NMR (HCl salt, DMSO-$d_6$) δ 1.98 (br s, 4H, —$CH_2CH_2$—), 2.86 (s, 3H, —$NCH_3$), 3.24.3 (complex, 8H, 4 —$CH_2$—), 6.25 (m, 1H, —CH—), 7.16 (d, J=7.4 Hz, 2H, aromatic), 7.33 (d, J=7.5 Hz, 2H, aromatic), 7.7 (m, 2H, aromatic), 8.08 (s, 1H, aromatic), 8.23 (m, 1H, aromatic). MS (FAB) m/z 383. Anal. (C, H, N) $C_{21}H_{26}N_4O_3$.2HCl.0.75$H_2O$.

EXAMPLE 61

2-(N-Bis-sulfonamido-4-aminophenyl)-N-methyl-N-[(1S)-1-(3-nitrophenyl)-2-(1-pyrrolidinyl)ethyl]acetamide (16, ADL-01-0133-7)

With stirring in ice-$H_2O$ under $N_2$, a solution of MsCl (1.56 mL, 20.17 mmol) in $CH_2Cl_2$ (6 mL) was added dropwise over 2-3 min to a mixture of 15 (1.5430 g, 4.0344 mmol) and $Et_3N$ (5.6 mL, 40 mmol) in $CH_2Cl_2$ (24 mL). After 10 mn, the mixture was stirred at 25° C. under $N_2$ overnight before the mixture was partitioned between $CH_2Cl_2$ and sat'd $NaHCO_3$. The 15 aqueous fraction was extracted with more $CH_2Cl_2$, and the combined organic fraction was dried ($Na_2SO_4$), filtered through celite, and evaporated. Acetonitrile was added to azeotrope off $Et_3N$ before the crude product was flash column chromatographed eluting with $CH_2Cl_2$:2% $NH_3$. The product was converted to the HCl salt with 1.0 M HCl in $Et_2O$ and washed with hot MeOH to yield 16-HCl (1.309 1 g, 56%, first crop): m.p. (HCl salt) 257-259° C.; $^1H$ NMR (HCl salt, DMSO-$d_6$) δ 1.99 (br s, 4H, —$CH_2CH_2$—), 2.87 (s, 3H, —$NCH_3$), 3. 15-4.3 (complex, 8H, 4 —$CH_2$—), 3.51 (s, 6H, 2-$SO_2CH_3$), 6.25 (m, 1H, —CH—), 7.4 (m, 4H, aromatic), 7.7 (m, 2H, aromatic), 8.1 (s, 1H, aromatic), 8.21 (m, 1H, aromatic). MS (FAB) m/z 539. Anal. (C, H, N) $C_{23}H_{30}N_4O_7S_2$.HCl0.5$CH_2Cl_2$.

EXAMPLE 62

2-(N-Bis-sulfonamido-4-aminophenyl)-N-methyl-N-[(1S)-1-(3-aminophenyl)-2-(1-pyrrolidinyl)ethyl]acetamide (17, ADL-01-0136-0)

ADL-01-0136-0 was prepared from 16 (1.0729 g, 1.992 mmol), Raney nickel, and hydrazine 30 hydrate (2 mL) in EtOH (30 mL). The conditions were similar to those used for the preparation of 9. The product was gravity column chromatographed eluting with $CH_2Cl_2$:2% $NH_3$, and the pure fractions were converted to the HCl salt with 1.0 M HCl in $Et_2O$ to yield 17-HCl (0.1194 g, 11%, unoptimized): m.p. (HCl salt) 252-255° C.; $^1H$ NMR (HCl salt, DMSO-$d_6$) δ 2.0 (br s, 4H, —$CH_2CH_2$—), 2.86 (s, 3H, —$NCH_3$), 3.1-4.2 (complex, 8H, 4 —$CH_2$—), 3.54 (s, 6H, 2 —$SO_2CH_3$), 6.1 (m, 1H, —CH—), 6.8-7.5 (complex, 8H, aromatic). MS (FAB) m/z 509. Anal. (C, H, N) $C_{23}H_{32}N_4O_5S_2$.1.75HCl.

EXAMPLE 63

2-(N-Bis-sulfonamido-4-aminophenyl)-N-methyl-N-[(1S)-1-(N-diethyl phosphoramidate-3-aminophenyl)-2-(1-pyrrolidinyl)ethyl]acetamide (19, ADL-01-0139-4)

With stirring in ice-$H_2O$ under $N_2$, diethyl chlorophosphate (0.84 mL, 5.81 mmol) was added to a mixture of 17 (0.7383 g, 1.4514 mmol) and NEt(iPr)$_2$ (1.5 mL, 8.7 mmol) in dry THF (15 mL). After 10 min, the mixture was stirred at 25° C. under $N_2$ overnight before more THF (15 mL), NEt(iPr)$_2$ (0.76 mL), and diethyl chlorophosphate (0.42 mL) were sequentially added. After 3 h, the mixture was quenched with $H_2O$, diluted with $CH_2Cl_2$, evaporated, and dried in vacuo. The residue was partitioned between $CH_2Cl_2$ and sat'd $NaHCO_3$. The aqueous fraction was extracted with more $CH_2Cl_2$, and the combined organic fraction was dried ($Na_2SO_4$), filtered through celite, and evaporated. The crude product was flash column chromatographed eluting with $CH_2Cl_2$:2% $NH_3$:1.5% MeOH before it was converted to the HCl salt with 1.0 M HCl in $Et_2O$ and crystallized from MeOH to yield 19-HCl (0.3274 g, 33%): m.p. (HCl salt) 245-247° C.; $^1H$ NMR (HCl salt, DMSO-d $O_6$) δ 1.193 (t, J=7 Hz, 6H, 2 —$CH_3$), 1.95 (br s, 4H, —$CH_2CH_2$—), 2.81 (s, 3H, —$NCH_3$), 3.1-4.1 (complex, 12H, 6 —$CH_2$—), 3.52 (s, 6H, 2 —$SO_2CH_3$), 6.1 (m, 1H, —CH—), 6.79 (d, J=7.3 Hz, 1H, aromatic), 6.91 (s. 1H, aromatic), 6.99 (d, J=7.7 Hz, 1H, aromatic), 7.23 (d, J=7.8 Hz, 1H, aromatic), 7.36 (d. J=8.3 Hz, 2H, aromatic), 7.44 (d, J=8.6 Hz, 2H, aromatic), 8.09 (d, J=9.4 Hz, 1H, —NHP). MS (FAB) mn/z 645. Anal. (C, H, N) $C_{27}H_{41}N_4O_8S_2P$.HCl.

EXAMPLE 64

2-(2-Nitrophenyl)-N-methyl-N-{[1S]-1-phenyl-2-[1-(3S)-(3-hydroxypyrrolidinyl)]ethyl]acetamide (21, ADL-01-0055-2)

With stirring at 25° C. under $N_2$, DCC (0.160 g, 0.79 mmol) was added to a mixture of 2-nitrophenylacetic acid (0.140 g, 0.79 mmol) and pyridine (0.064 mL, 0.79 mmol) in $CH_2Cl_2$ (1.5 mL). After 3 min, a solution of 20 (0.160 g, 0.72 mmol) in $CH_2Cl_2$ (1.5 mL) was added, followed by NEt(iPr)$_2$ (0.375 mL, 2.15 mmol). The mixture was stirred at 25° C. under $N_2$ overnight before sat'd $NaHCO_3$ was added, and the mixture was filtered through celite. The DCU was washed with a little $CH_2Cl_2$, and the filtrate was partitioned between sat'd $NaHCO_3$ and $CH_2Cl_2$, which was dried ($MgSO_4$), filtered through celite, and evaporated. Toluene was added to azeotrope off pyridine. The product was flash column chromatographed eluting with $CHCl_3$:2% $NH_3$:2% MeOH before it was converted to the HCl salt with 1.0 M HCl in $Et_2O$ and crystallized from MeOH to yield 21.HCl (0.14 g, 47%): m.p. (HCl salt) 226-227° C.; $^1H$ NMR (HCl salt, DMSO-$d_6$) δ 1.8-2.4 (m, 2H,—$CH_2$), 2.86 (s, 3H, —$NCH_3$), 34.5 (complex, 8H, 4 —$CH_2$—), 5.5 (m, 1H, —CHOH), 6.1 (m, 1H, —CH—), 73-7.8 (complex, 8H, aromatic), 8.11 (d, J=8 Hz, 1H, aromatic). MS (FAB) m/z 384. Anal. (C, H, N) $C_{21}H_{25}N_3O_4$.HCl.0.5..$H_2O$.

EXAMPLE 65

2-(2-Nitro-4,5-dichlorophenyl)-N-methyl-N-{[1S]-1-phenyl-2-[1-(3S)-(3-hydroxypyrrolidinyl)] ethyl}acetamide (22, ADL-01-0056-0)

ADL-01-0056-0 was prepared from 20 (0.2 g, 0.91 mmol), 2-nitro-4,5-dichlorophenylacetic acid (0.45 g, 1.8 mmol), DCC (0.37 g, 1.8 mmol), NEt(iPr)$_2$ (0.48 mL, 2.7 mmol), and pyridine (0.15 mL, 1.8 mmol). The conditions are similar to those for the preparation of 21. The product was column chromatographed eluting with CH$_2$Cl$_2$:2% NH$_3$: 1% MeOH before it was converted to the HCl salt with 1.0 M HCl in Et$_2$O and crystallized from iPrOH to yield 22.HCl (0.060 g, 14%): m.p. (HCl salt) 23 1-233° C. (dec); $^1$H NMR (HCl salt, DMSO-d$_6$) δ 1.8-2.4 (m, 2H, —CH$_2$—), 2.85 (s, 3H, —NCH$_3$), 3.1-4.5 (complex, 8H, 4 —CH$_2$—), 5.5 (m, 1H, —CHOH), 6.1 (m, 1H, —CH—), 7.2-7.5 (m, 5H, aromatic), 7.88 (s, 1H, aromatic), 8.42 (s, 1H, aromatic). MS (FAB) m/z 452. Anal. (C, H, N) C$_{21}$H$_{23}$N$_3$O$_4$Cl$_2$.HCl.

EXAMPLE 66

2-(4-methylsulfonylphenyl)-N-methyl-N-{[1S]1-1-phenyl-2-[1-(3S)-(3-hydroxypyrrolidinyl)]] ethyl}acetamide (25, ADL-01-0064-4)

ADL-01-0064-4 was prepared from 20 (0.2 g, 0.91 mmol), 4-methylsulfonylphenylacetic acid (0.41 g, 1.8 mmol), DCC (0.37 g, 1.8 mmol), pyridine (0.15 mL, 1.8 mmol), and NEt(iPr)$_2$ (0.48 mL, 2.7 mmol). The conditions are similar to those for the preparation of 21. After stirring at 25° C. overnight, more pyridine (0.075 mL, 0.9 mmol) and DCC (0.18 g, 0.9 mmol) were added, and the reaction was worked up the next day. The product was purified by radial chromatography eluting with CH$_2$Cl$_2$:2% NH$_3$:1% MeOH before it was converted to the HCl salt with 1.0 M HCl in Et$_2$O and washed with hot iPrOH to yield 25-HCl (0.15 g, 36%): m.p. (HCl salt) 240-241° C.; $^1$H NMR (HCl salt, DMSO-d$_6$) δ 1.8-2.4 (m, 2H, —CH$_2$—), 2.8 (d, 3H, —NCH$_3$ of cis and trans amide rotamers), 3.23 (s, 3H, —SO$_2$CH$_3$), 3.1-4.5 (m, 8H, 4 —CH$_2$—), 5.5 (m, 1H, —CHOH), 6.15 (m, 1H, —CH—), 7.2-7.5 (m, 5H, aromatic), 7.55 (m, 2H, aromatic), 7.85 (m, 2H, aromatic). MS (FAB) m/z 417. Anal. (C, H, N) C$_{22}$H$_{28}$N$_2$O$_4$S.HCl.

EXAMPLE 67

2-(2-Nitro-4-trifluoromethylphenyl)-N-methyl-N-{[1S]-1-phenyl-2-[1-(3S)-(3-hydroxypyrrolidinyl)] ethyl}acetamide (26, ADL-01-0067-7)

With stirring at 25° C. under N$_2$, DCC (0.39 g, 1.9 mmol) was added to a mixture of 2-nitro-4-20 trifluoromethylphenylacetic acid (0.47 g, 1.9 mmol) and pyridine (0.15 mL, 1.9 mmol) in CH$_2$Cl$_2$ (10 mL). After 5 min, a solution of 20 (0.4 g, 1.8 mmol) in CH$_2$Cl$_2$ (5 mL) was added. After 2 h, more DCC (0.1 g, 0.5 mmol) was added, and the mixture was stirred at 25° C. overnight before more 2-nitro-4-trifluoromethylphenylacetic acid (0.045 g, 0.18 mmol) and DCC (0.1 g, 0.5 mmol) were added. After 2 h, the reaction was worked up as in the 25 preparation of 21. The product was purified by radial chromatography eluting with CH$_2$Cl$_2$:2% NH$_3$ before it was converted to the HCl salt with 1.0 M HCl in Et$_2$O and precipitated from CH$_2$Cl$_2$ to yield 26HCl (0.050 g, 5.4%): $^1$H N (HCl salt, DMSO-d$_6$) δ 1.8-2.4 (m, 2H, —CH$_2$—), 2.87 (s, 3H, —NCH$_3$), 3.1-4.5 (complex, 8H, 4 —CH$_2$—), 5.5 (m, 1H, CHOH), 6.1 (m, 1H, —CH—), 7.2-7.5 (m, 5H, aromatic), 7.82 (d, J=7.7 Hz, 1H, aromatic), 8.16 (d, J=8 Hz, 30 1H, aromatic), 8.42 (s, 1H, aromatic). MS (FAB) m/z 452. Anal. (C, H, N) C$_{22}$H$_{24}$F$_3$N$_3$O$_4$HCl.0.5H$_2$O.

EXAMPLE 68

2-(2-Amino-4-trifluoromethylphenyl)-N-methyl-N-{[1S]-1-phenyl-2-[1-(3S)-(3-hydroxypyrrolidinyl) [ethyl]acetamide (27. ADL-01-0076-8)

ADL-01-0076-8 was prepared from 26 (0.14 g, 0.31 mmol), Raney nickel, and hydrazine hydrate (0.2 mL) in EtOH (14 mL). The conditions were similar to those used for the preparation of 9. The product was purified by radial chromatography eluting with CHCl$_3$:2% NH$_3$:2% MeOH before it was converted to the HCl salt with Et$_2$O—HCl to yield 27.HCl (0.11 g, 77%): $^1$H NMR (DMSO-d$_6$) δ 1.8-2.2 (m, 2H, —CH$_2$—), 2.88 (s, 3H, —NCH$_3$), 3.1-4.5 (complex, 9H, 4 —CH$_2$— and 1 —CHOH), 6.2 (m, 1H, —CH—), 6.8-7.5 (complex, 8H, aromatic). MS (FAB) m/z 423. Anal. (C, H, N) C$_{22}$H$_{26}$N$_3$O$_2$F$_3$.HCl$_2$.5H$_2$O.

Compounds of Examples 69-91 were prepared from the appropriate arylacetic acids/acid 5 chlorides via EDCI/DIPEA or DCC/pyridine couplings, followed by reduction, deprotection, and/or derivatization via known chemistry. Intermediate A was prepared via the method reported in J. Med. Chem., 34, 1991 pp. 18 1-189, Costello, G. F. et al.,

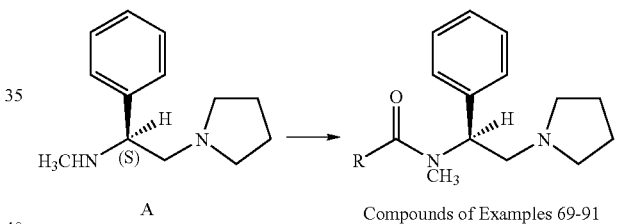

A      Compounds of Examples 69-91

General Procedure for EDCI/DIPEA Coupling.

To a solution of acid (1.1 eq.) and 1-hydroxybenzotriazole hydrate (HOBT; 1.1 eq.) in an ice-bath under N$_2$ was added 1-(3-Dimethylaminopropyl)-3-ethylcarbodiimide hydrochloride (EDCI;1.1 eq.). The mixture was stirred for 30 minutes. A solution of the amine (1.0 eq.) in dry methylene chloride was added drop-wise followed by N,N-Diisopropylethyamine (DIPEA;1.5eq.). The solution was allowed to stir at room temperature overnight. The reaction was quenched with sat. sodium bicarbonate and separated from methylene chloride. The organic layer was dried (Na$_2$SO$_4$), filtered through Celite, and evaporated. The crude product was chromatographed and converted to the HCl salt.

EXAMPLE 69

2,2-Diphenyl-N-methyl-N-[(1S)-1-phenyl-2-(1-pyrrolidinyl)ethyl]acetamide; ADL-01-0023-0

To a solution of Diphenylacetic acid (1.5 g; 7.3 mmol) and pyridine (1.0 mL; 12.2 mmol) in 20 mL of dry methylene chloride at 25 degrees under N$_2$ was added 1,3 dicyclohexylcarbodiimide, DCC (2.0 g; 9.8 mmol). After 5 minutes, 28 (1.0 g, 4.9 mmol) in 20 mL of dry methylene chloride was added and the mixture was stirred overnight. TLC (95:5 methylene chloride:methanol with 2% ammonia) indicated all of the starting material was consumed. The reaction was quenched with sat. sodium bicarbonate and filtered through a Celite plug. The plug was rinsed with methylene chloride and the aqueous layer was extracted with methylene chloride. The combined organic layers were dried ($Na_2SO_4$), filtered and concentrated in vacuo to give 2.2 g of a light brown solid. The crude product was purified by flash chromatography using a stepwise gradient of 2% to 8% MeOH: methylene chloride with 2% ammonia to afford 1.7 g (88%) of pure product which was treated with 1.0 M HCl in diethyl ether to give 29 as the HCl salt. $^1$H NMR (HCl salt, DMSO-$d_6$) δ 2.0(br s, 4H, —$CH_2CH_2$—), 2.7(s, 3H, —$NCH_3$), 6.2 (br m, 1H, —CH—), 7.1-7.5 (complex, 15H, aromatic). MS (FAB) m/z 398. Anal. (C,H,N) $C_{27}H_{30}N_2O \cdot HCl \cdot 0.75H_2O$.

EXAMPLE 70

N',N'-Diphenyl-N-methyl-N-[(1S)-1-phenyl-2-(1-pyrrolidinyl)ethyl]urea, ADL-01-0027-1

To a 0 degree solution of 28 (500 mg; 2.4 mmol) and triethylamine (731 mL; 5.2 mmol) in 10 mL of dry methylene chloride under $N_2$ was added a solution of Diphenylcarbamyl chloride (629 mg; 2.7 mmol) in 5 mL of dry methylene chloride. The solution was warmed to room temperature and stirred overnight. TLC (95:5 methylene chloride: methanol with 2% ammonia) indicated the starting material was consumed. The reaction solution was concentrated to a residue, which was pre-adsorbed onto silica and purified using a stepwise gradient of 2% to 7% MeOH: methylene chloride with 2% ammonia to afford 350 mg (36%) of pure product which was treated with 1.0M HCl in diethyl ether to give 30 as the HCl salt. $^1$H NMR (HCl salt, DMSO-$d_6$) δ 2.0 (br s, 4H, —$CH_2CH_2$—), 2.5 (s, 3H, —$NCH_3$), 5.8 (br, m, 1H, —CH—), 7.1-7.5 (complex, 15H, aromatic). MS(FAB) m/z 399. Anal. (C,H,N) $C_{29}H_{29}N_3O \cdot HCl \cdot 0.5H_2O$.

EXAMPLE 71

2-(2-Nitrophenyl)-N-methyl-N-[(1S)-1-phenyl-2-(1-pyrrolidinyl)ethyl]acetamide; ADL-01-0030-5

ADL-01-0030-5 was prepared via the procedure described in the preparation of 29 from 28 (0.6 g; 2.9 mmol), 2-nitrophenylacetic acid (0.8 g; 4.4 mmol), DCC (1.2 g; 5.8 mmol), and pyridine (0.1 mL; 1.4 mmol). The crude product was purified by flash chromatography using a stepwise gradient of 2% to 7% MeOH: methylene chloride with 2% ammonia to afford 0.2 g (20%) of pure product which was treated with 1. OM HCl in diethyl ether to give 31 as the HCl salt. $^1$H NMR (HCl salt, DMSO-$d_6$) δ 2.0 (br s, 4H, —$CH_2CH_2$—), 2.9 (s, 3H, —$NCH_3$), 6.1(br, m, 1H, —CH—) 7.3-8.1 (complex, 9H, aromatic). MS(FAB) m/z 367. Anal. (C,H,N) $C_{21}H_{25}N_3O_3 \cdot HCl$.

EXAMPLE 72

2-(2-Nitro-4,5-dichlorophenyl)-N-methyl-N-[(1S)-1-phenyl-2-(1-pyrrolidinyl)ethyl]acetamide: ADL-01-0033-974

ADL-01-0033-9 was prepared via the general EDCI/DIPEA coupling procedure from 28 (1.4 g; 6.9 mmol), 2-nitro 4,5-dichlorophenylacetic acid (1.9 g; 7.6 mmol), HOBT (1.0 g; 7.6 mmol), EDCI (1.4 g; 7.6 mmol), and pyridine (0.8 mL; 10.3 mmol). The crude product was purified by flash chromatography using a stepwise gradient of 2% to 5% MeOH: methylene chloride with 2% ammonia to afford 2.0 g (60%) of pure product which was treated with 1.0M HCl in diethyl ether to give 32 as the HCl salt. $^1$H NMR (HCl salt, DMSO-$d_6$) δ 2.0 (br, s, 4H, —$CH_2CH_2$—), 2.9 (s, 3H, —$NCH_3$), 6.1 (br, m, 1H, —CH—), 7.2-7.6 (complex, 5H, aromatic), 7.9 (s, 1H, aromatic), 8.4 (s, 1H, aromatic). MS(FAB) m/z 436. Anal. (C,H,N) $C_{21}H_{23}N_3O_3Cl_2 \cdot HCl \cdot 0.25 H_2O$.

EXAMPLE 73

2-(4-methylsulfonyl phenyl)-N-methyl-N-[(1S)-1-phenyl-2-(1-pyrrolidinyl)ethyl]acetamide: ADL-01-0036-2

ADL-01-0036-2 was prepared via the general EDCI/DIPEA coupling procedure from 28 (432 mg; 2.mmol), 4-methylsulfonylphenylacetic acid (500 mg; 2.3 mmol), HOBT (341 mg; 2.5 mmol), EDCI (483 mg; 2.5 mmol), and DIPEA (550 mL; 3.1 mmol). The crude product was purified by flash chromatography using a stepwise gradient of 2% to 4% MeOH: methylene chloride with 2% ammonia to afford 160 mg (19%) of pure product which was treated with 1.0M HCl in diethyl ether to give 33 as the HCl salt. $^1$H NMR (HCl salt, DM50-$d_6$) δ 2.0 (br, s, 4H, —$CH_2 CH_2$—), 2.9 (s, 3H, —$NCH_3$), 3.2 (s, —$SO_2CH_3$), 6.1 (br, m, 1H, —CH—), 7.3-7.5 (complex, 5H, aromatic), 7.6 (br, d, 2H, aromatic), 7.9 (br, d, 2H, aromatic). MS(FAB) m/z 400. Anal. (C,H,N) $C_{22}H_{28}N_2O_3S \cdot HCl \cdot 0.5 H_2O$.

EXAMPLE 74

2-(2-Methoxyphenyl)-N-methyl-N-1S)-1-phenyl-2-(1-pyrrolidinyl)ethyl]acetamide ADL-01-0049-5

ADL-01-0049-5 was prepared via the general EDCI/DIPEA coupling procedure from 28 (500 mg; 2.4 mmol), 2-Methoxyphenylacetic acid (610 mg; 3.6 mmol), HOBT (495 mg; 3.6 mmol), EDCI (700 mg; 3.6 mmol), and DIPEA (850 mL; 4.8 mmol). The crude product was purified by flash chromatography using a stepwise gradient of 1% to 7% MeOH: methylene chloride with 2% ammonia to afford 822 mg (96%) of pure product which was treated with 1.0M HCl in diethyl ether to give 34 as the HCl salt. $^1$H NMR (free base, $CDCl_3$) 81.8 (br, s, 4H, —$CH_2CH_2$—), 2.8 (s, 3H, —$NCH_3$), 3.8 (s, 3H, $OCH_3$), 6.1 (br, m, 1H, —CH—), 6.8-7.4 (complex, 9H, aromatic). MS(FAB) m/z 352. Anal. (C,H,N) $C_{22}H_{28}N_2O_2 \cdot HCl$.

EXAMPLE 75

2-(3-Indolyl)-N-methyl-N-(1S)-1-phenyl-2-(1-pyrrolidinyl)ethyl]acetamide; ADL-01-0054-5

ADL-01-0054-5 was prepared via the general EDCI/DIPEA coupling procedure from 28 (500 mg; 2.4 mmol), Indole-3-acetic acid (641 mg; 3.6 mmol), HOBT (494 mg; 3.6 mmol), EDCI (700 mg; 3.6 mmol), and DIPEA(637 mL; 3.6 mmol). The crude product was purified by flash chromatography using a stepwise gradient of 1% to 7% MeOH: methylene chloride to afford 761 mg (88%) of pure product which was treated with 1.0M HCl in diethyl ether to give 35 as the HCl salt. $^1$H NMR(HCl salt, $CD_3OD$) δ 2.1 (br, s, 4H, —$CH_2CH_2$—), 2.8 (s, 3H, —$NCH_3$), 6.3 (br, m, 1H, —CH—), 7.1-7.7 (complex, 9H, aromatic). MS(FAB) m/z 361. Anal. (C,H,N) $C_{23}H_{27}N_3O.HCl.1.0 H_2O$.

EXAMPLE 76

2-(α,α,α-Trifluoro-p-tolyl)-N-methyl-N-[(1S)-1-phenyl-2-(1-pyrrolidinyl)ethyl]acetamide: ADL-01-0058-6

ADL-01-0058-6 was prepared via the general EDCI/DIPEA coupling procedure from 28 (200 mg; 0.9 mmol), (α,α,α-Trifluoro-p-tolyl) acetic acid (239 mg; 1.1 mmol), HOBT (157 mg; 1.1 mmol), EDCI (223 mg; 1.1 mmol), and DIPEA (203 mL; 1.1 mmol). The crude product was purified by flash chromatography using a stepwise gradient of 1% to 2% MeOH: methylene chloride to afford 354 mg (93%) of pure product which was treated with 1.0M HCl in diethyl ether to give 36 as the HCl salt. $^1$H NMR (HCl salt, $CDCl_3$) δ 1.8 (br, s, 4H, —$CH_2CH_2$—), 3.0 (s, 3H, $NCH_3$), 6.4 (br, m, 1H, CH), 7.2-7.6 (complex, 9H, aromatic). MS(FAB) m/z 390. Anal. (C,H,N) $C_{22}H_{25}N_2OF_3.HCl$.

EXAMPLE 77

2-(2-Nitro-α,α,α-Trifluro-4-tolyl)-N-methyl-N-[(1S)-1-phenyl-2-(1-pyrrolidinyl)ethyl]acetamide; ADL-01-0062-8

ADL-01-0062-8 was prepared via the general EDCI/DIPEA coupling procedure from 28 (500 mg; 2.4 mmol), (2-Nitro-α,α,α-trifluoro-4-tolyl)acetic acid (728 mg; 2.9 mmol), HOBT (395 mg; 2.9 mmol), EDCI (559 mg; 2.9 mmol), and DIPEA (5 10 mL; 2.9 mmol). The crude product was purified by flash chromatography using a stepwise gradient of 2% to 10% MeOH:methylene chloride to afford 786 mg, (74%) of pure product which was treated with 1.0M HCl in diethyl ether to give 37 as the HCl salt. $^1$H NMR (HCl salt, $CDCl_3$) δ 2.0 (br, s, 4H, —$CH_2CH_2$), 2.9 (s, 3H, —$NCH_3$), 6.3 (br, m, 1H, CH), 7.1-7.5 (complex, 4H, aromatic), 7.8-7.9 (br, m, 2H, aromatic), 8.3-8.4 (br, s, 2H, aromatic). MS(FAB) m/z 435. Anal. (C,H,N) $Cl_2H_{24}N_3O_3F_3.HCl$.

EXAMPLE 78

2-(1-[4-Chlorobenzoyl)-5-methoxy-2-methyl indole)-N-[(1S)-1-phenyl-2-(1-pyrrolidinyl)ethyl]acetamide; ADL-01-0078-4

ADL-01-0078-4 was prepared via the general EDCI/DIPEA coupling procedure from 28 (100 mg; 0.4 mmol), (1-[p-chlorobenzoyl)-5-methoxy-2-methyl indole-3-acetic acid (189 mg; 0.5 mmol), HOBT (73 mg; 0.5 mmol), EDCI (101 mg; 0.5 mmol), and DIPEA (128 mL; 0.7 40 mmol). The crude product was purified by flash chromatography using a stepwise gradient of 2% to 5% MeOH:methylene chloride to afford 200 mg (79%) of pure product which was treated with 1.0M HCl in diethyl ether to give 38 as the HCl salt. 1H NMR (HCl salt, $CDCl_3$) 1.6-1.8 (br, m, 4H, —$CH_2CH_2$—), 2.3 (b, s, 3H, —$CH_3$), 2.9 (br, s, —$NCH_3$), 3.8 (br, s, 3H, —$OCH_3$), 6.7 (br, m, 1H, —CH), 7.1-7.6 (complex, 12H, aromatic). MS(FAB) m/z 509. Anal. 45 (C,H,N) $C_{32}H_{35}N_3O_3Cl.HCl$.

EXAMPLE 79

2-(4-Nitrophenyl)-N-methyl-N-[(1S)-1-phenyl-2-(1-pyrrolidinyl)ethyl]acetamide; ADL-01-0079-2

ADL-01-0079-2 was prepared via the general EDCI/DIPEA coupling procedure from 28 (1.5 g; 7.3 mmol), 4-Nitrophenylacetic acid (2.0 g; 11.0 mmol), HOBT 1.4 g; 11.0 mmol), EDCI (2.1 g; 11.0 mmol), and DIPEA (2.5 mL;1 4.6 mmol). The crude product was purified by flash chromatography using a stepwise gradient of 1% to 5% MeOH: methylene chloride to afford 2.5 g (93%) of pure product which was treated with 1.0M HCl in diethyl ether to give 39 as the HCl salt. $^1$H NMR (HCl salt, $CDCl_3$) δ 1.6 (br, m, 4H, —$CH_2CH_2$—), 2.8 (br, s, 3H, —$NCH_3$), 6.4 (br, m, 1H, —CH), 7.1-7.5 (complex, 7H, aromatic), 8.0 (br, d, 2h, aromatic). MS (FAB) M/Z 367. Anal. (C,H,N) $C_{21}H_{25}N_3O_3.HCl$.

EXAMPLE 80

2-(3-Nitrophenyl)-N-methyl-N-[(1S)-1-phenyl-2-(1-pyrrolidinyl)ethyl]acetamide; ADL-01-0084-2

ADL-01-0084-2 was prepared via the general EDCI/DIPEA coupling procedure from 28 (1.5 g; 7.3 mmol), 3-Nitrophenylacetic acid (2.0 g; 11.0 mmol), HOBT (1.4 g; 11.0 mmol), EDCI (2.1 g; 11.0 mmol), and DIPEA (2.5 mL; 14.6 mmol). The crude product was purified by flash chromatography using a stepwise gradient of 1% to 5% MeOH: methylene chloride with 2% ammonia to afford 2.6 g (100%) of pure product which was treated with 1.0M HCl in diethyl ether to give 40 as the HCl salt. $^1$H NMR (HCl salt, $CDCl_3$) δ 2.0 (br, m, 4H, —$CH_2CH$,—), 2.9 (br, s, 3H, —$NCH_3$), 6.3 (br, m, 1H, —CH), 7.2-7.6 (complex, 6H, aromatic), 7.8 (br, d, 1H, aromatic), 8.1-8.2 (complex, 2H, aromatic). MS(FAB) m/z 367. Anal. (C,H,N) $C_{21},H_{25}N_3O_3.HCl.0.5 H_2O$.

EXAMPLE 81

2-(2-Pyridyl)-N-methyl-N-[(1S)-1-phenyl-2-(1-pyrrolidinyl)ethyl]acetamide ADL-01-0085-9

ADL-01-0085-9 was prepared via the general EDCI/DIPEA coupling procedure from 28 (350 mg; 1.7 mmol), 2-Pyridylacetic acid hydrochloride (326 mg; 1.8 mmol), HOBT (253 mg; 1.8 mmol), EDCI (360 mg; 1.8 mmol) and DIPEA (644 mL; 3.7 mmol). The crude product was purified by flash chromatography using a stepwise gradient of 2% to 5% MeOH: methylene chloride with 2% ammonia to afford 400 mg (72%) of pure product which was treated with 1.0M HCl in diethyl ether to give 41 as the HCl salt. $^1$H NMR (free base, $CDCl_3$) δ 1.7-1.9 (br, m, 4H, —$CH_2CH_2$), 2.8 (br, s, 3H, —$NCH_3$), 6.0-6.2 (br, m, 1H, —CH), 7.1-7.8 (complex, 8H, aromatic), 8.5 (br, d, 1H, aromatic). MS(FAB) m/z 323. Anal. (C,H,N) $C_{20}H_{25}N_3O.2HCl.0.5H_2O$.

EXAMPLE 82

2-(3-Pyridyl)-N-methyl-N-[(1S)-1-phenyl-2-(1-pyrrolidinyl)ethyl]acetamide ADL-01-0100-6

ADL-01-0100-6 was prepared via the general EDCI/DIPEA coupling procedure from 28 (120 mg; 0.5 mmol), 3-Pyridylacetic acid hydrochloride (110 mg; 0.6 mmol), HOBT (85 mg; 0.6 mmol), EDCI (120 mg; 0.6 mmol), and DIPEA (280 mL; 1.5 mmol). The crude product was purified by flash chromatography using a stepwise gradient of 1% to 6% MeOH:methylene chloride with 2% ammonia to afford 142 mg (76%) of pure product which was treated with 1.0M HCl in diethyl ether to give 42 as the HCl salt. $^1$H NMR (HCl salt, CDCl$_3$) δ 2.1 (br, m, 4H, —CH$_2$CH$_2$—), 2.9 (br, s, 3H, —NCH$_3$), 6.2-6.3 (br, m, 1H, —CH), 7.2-7.3 (complex, 5H, aromatic), 7.8-7.9 (br, t, 1H, aromatic), 8.6-8.9 (complex, 3H, aromatic). MS(FAB) m/z 323. Anal. (C,H,N) C$_{21}$H$_{25}$N$_3$O.2 HCl.1.25 H$_2$O.

EXAMPLE 83

2-((±)-6-Methoxy-a-methyl-2-naphthalene)-N-[(1S)-1-phenyl-2-(1-pyrrolidinyl)ethyl]acetamide; ADL-01-0110-5

ADL-01-0110-5 was prepared via the general EDCI/DIPEA coupling procedure from 28 (200 m; 0.9 mmol), (±)-6-Methoxy-a-methyl-2-naphthaleneacetic acid (217 mg; 1.0 mmol), HOBT (142 mg; 1.0 mmol), EDCI (201 mg; 1.0 mmol), and DIPEA (256 mL; 1.4 mmol). The crude product was purified by flash chromatography using a stepwise gradient of 1% to 2% MeOH:methylene chloride with 2% ammonia to afford 130 mg(33%) of pure product which was treated with 1.0M HCl in diethyl ether to give 43 as the HCl salt. $^1$H NMR (HCl salt, CDCl$_3$) δ 1.4 (d, 3H, —CH$_3$), 2.9 (br, s, —NCH$_3$), 3.9 (s, —OCH$_3$), 5.5 (br, m, 1H, —CH), 7.0-7.7 (complex, 11H, aromatic). MS(FAB) m/z 416. Anal. (C,H,N) C$_{27}$H$_{32}$N$_2$O$_2$.HCl.0.25H$_2$O.

EXAMPLE 84

2-(α,α,α-Trifluoro-3-tolyl)N-methyl-N-[(1S)-1-phenyl-2-(1-pyrrolidinyl)ethyl]acetamide; ADL-01-0111-3

ADL-01-0111-3 was prepared via the general EDCI/DIPEA coupling procedure from 28 (200 mg; 0.9 mmol), (α,α,α-Trifluoro-m-tolyl)acetic acid (214 mg; 1.0 mmol), HOBT (142 mg; 1.0 mmol), EDCI (201 mg; 1.0 mmol), and DIPEA (256 mL; 1.4 mmol). The crude product was purified by flash chromatography using a stepwise gradient of 2% to 6% MeOH:methylene chloride to afford 250 mg (67%) of pure product which was treated with 1.0M HCl in diethyl ether to give 44 as the HCl salt. $^1$H NMR (HCl salt, CDCl$_3$) δ 2.0 (br, m, 4H, —CH$_2$CH$_2$—), 2.9 (br, s, 3H, —NCH$_3$), 6.4 (br, m, 1H), 7.1-7.7 (complex, 9H, aromatic). MS (FAB) m/z 390. Anal. (C,H,N) C$_{22}$H$_{25}$N$_2$OF$_3$.HCl.

EXAMPLE 85

2-(4-Pyridyl)-N-methyl-N-[(1S)-1-phenyl-2-(1-pyrrolidinyl)ethyl]acetamide; ADL-01-0122-0

ADL-01-0122-0 was prepared via the general EDCI/DIPEA coupling procedure from 28 (120 mg; 0.5 mmol), 4-Pyridylacetic acid hydrochloride (150 mg; 0.8 mmol), HOBT (117 mg; 0.8 mmol), EDCI (166 mg; 0.8 mmol), and DIPEA (202 mL; 1.1 mmol). The crude product was purified by flash chromatography using a stepwise gradient of 2% to 5% MeOH:methylene chloride to afford 172 mg (92%) of pure product which was treated with 1.0M HCl in diethyl ether to give 45 as the HCl salt. $^1$H NMR (HCl salt, CDCl$_3$) δ 2.1 (br, m, 4H, —CH$_2$CH$_2$—), 2.9 (br, s, —NCH$_3$), 6.3 (br, m, —CH), 7.2-7.3 (complex, 5H, aromatic), 7.8 (br, s, 2H, aromatic), 8.6 (br, s, 2H, aromatic). MS (FAB) m/z 323. Anal. (C,H,N) C$_{20}$H$_{25}$N$_3$O.1.5HCl.0.5H$_2$O.

EXAMPLE 86

2-(α,α,α-Trifluoro-2-tolyl)-N-methyl-N-[(1S)-1-phenyl-2-(1-pyrrolidinyl)ethyl]acetamide: ADL-01-0123-8

ADL-01-0123-8 was prepared via the general EDCI/DIPEA coupling procedure from 28 (200 mg; 0.9 mmol), (α,α,α-Trifluoro-o-tolyl)acetic acid (239 mg; 1.1 mmol), HOBT (157 mg; 1.1 mmol), EDCI (223 mg; 1.1 mmol), and DIPEA (203 mL; 1.1 mmol). The crude product was purified by flash chromatography using a stepwise gradient of 1% to 4% MeOH:methylene chloride with 2% ammonia to afford 339 mg (82%) of pure product which was treated with 1.0M HCl in diethyl ether to give 46 as the HCl salt. $^1$H NMR (HCl salt, CDCl$_3$) δ 2.0 (br, m, 4H —CH$_2$CH$_2$—), 2.9 (br, s, —NCH$_3$), 6.3 (br, m, 1H, —CH), 7.1-7.7 (complex, 9H, aromatic). MS (FAB) m/z 390. Anal. (C,H,N) C$_{22}$H$_{25}$N$_2$OF$_3$.HCl.

EXAMPLE 87

2(S)-(+)4-Isobutyl-α-methylphenyl)N-methyl-N-[(1S)-1-phenyl-2-(1-pyrrolidinyl)ethyl]acetamide: ADL-01-0125-3

ADL-01-0125-3 was prepared via the general EDCI/DIPEA coupling procedure from 28 (200 mg; 0.9 mmol), (S)-(+)4-Isobutyl-α-methylphenylacetic acid (217 mg; 1.0 mmol), HOBT (142 mg; 1.0 mmol), EDCI (201 mg; 1.0 mmol), and DIPEA (256 mL; 1.4 mmol). The crude product was purified by flash chromatography using a stepwise gradient of 1% to 2% MeOH:methylene chloride with 2% ammonia to afford 240 mg (66%) of pure product which was treated with 1.0M HCl in diethyl ether to give 47 as the HCl salt. $^1$H NMR (HCl salt, CDCl$_3$) δ 0.8 (d, 6H, —(CH$_3$)$_2$), 1.4(d, 2H, —CH$_3$), 2.0 (br, m, —CH$_2$CH$_2$—), 2.3-2.4 (d, 2H, —CH$_2$—), 2.9 (s, 3H, —NCH$_3$), 5.6 (br, m, 1H, —CH), 7.0 (br, q, 4H, aromatic), 7.3 (br, s, 5H, aromatic). MS(FAB) m/z 392. Anal. (C, H, N) C$_{26}$H$_{36}$N$_2$O.HCl.0.25H$_2$O.

EXAMPLE 88

2-(3,4,5-Trimethoxyphenyl)-N-methyl-B-[(1S)-1-phenyl-2-(1-pyrrolidinyl)ethyl]acetamide; ADL-01-0146-9

ADL-01-0146-9 was prepared via the general EDCI/DIPEA coupling procedure from 28 (250 mg; 1.2 mmol), 3,4,5-Trimethoxyphenylacetic acid (304 mg; 1.3 mmol), HOBT (181 mg; 1.3 mmol), EDCI (256 mg; 1.3 mmol), and DIPEA (318 mL; 1.8 mmol). The crude product was purified by flash chromatography using a stepwise gradient of 2% to 5% MeOH:methylene chloride with 2% ammonia to afford 500 mg (100%) of pure product which was treated with 1.0M HCl in diethyl ether to give 48 as the HCl salt. $^1$H NMR (free base, CDCl$_3$) δ 1.7 (br, m, 4H, —CH$_2$CH$_2$—), 2.7 (s, 3H, —NCH$_3$), 3.8 (d, 9H, —OCH$_3$), 6.0-6.2 (br, m, 1H, —CH), 6.4 (s, 2H, aromatic), 7.1-7.3 (complex, 5H, aromatic). MS (FAB) m/z 412. Anal. (C,H,N) C$_{21}$H$_{32}$N$_2$O$_4$.HCl.

EXAMPLE 89

2-(2-Aminophenyl)-N-methyl-N-[(1S)-1-phenyl-2-1-pyrrolidinyl)ethyl]acetamide ADL-01-0024-8

Raney-Nickel (50% slurry in water) was added to a mixture of 31 (2.30 g; 6.1 mmol), 2.2 mL (61.9 mmol) of hydrazine hydrate and 45 mL of abs. EtOH at 55 degrees to maintain a regular gas evolution. After 45 mm., TLC (95:5 methylene chloride:methanol w/2% ammonia) indicated that all of the starting material was consumed. The mixture was filtered through a Celite plug and rinsed with copious amounts of hot methanol. The filtrates were combined and concentrated in vacuo to afford 270 mg of a waxy solid. The crude product was purified by flash chromatography using a stepwise gradient of 1% to 8% methanol:methylene chloride with 2% ammonia to afford 2.01 g (97%) of desired product. The pure product was treated with 1.0M HCl in diethyl ether to yield 49 (ADL-01-0024-8) as the HCl salt. $^1$H NMR (HCl salt, DMSO-$d_6$) δ 2.0 (br, m, 4H, —$CH_2CH_2$—), 2.9 (s, 3H, —$NCH_3$), 6.1 (br, m, 1H, —CH), 7.2 (complex, 9H, aromatic). MS (FAB) m/z 321. Anal. (C,H,N) $C_{21}H_{27}N_3O.2HCl.0.75H_2O$.

EXAMPLE 90

2-(2-N,N-Dimethylsulfonamido-2-aminophenyl)-N-methyl-N-[(1S)-1-phenyl-2-(1-pyrrolidinyl)ethyl]acetamide; ADL-01-0060-2

To a solution of 49 (400 mg; 1.1 mmol) in 50 ml of dry methylene chloride was added 429 mL of triethylamine and MsCl (913 mL; 11.8 mmol) dissolved in 6 mL of dry methylene chloride. The dark red solution was allowed to stir overnight. TLC (95:5 methylene chloride:methanol w/2% ammonia) indicates the starting material is consumed. The reaction solution was quenched with sat. sodium bicarbonate and the layers were separated. The aqueous layer was extracted with methylene chloride and the combined organic layers were dried over anh. sodium sulfate, filtered and the solvent was concentrated in vacuo to give 700 mg of a dark brown residue. The crude product was purified by flash chromatography using a stepwise gradient of 2% to 7% methanol:methylene chloride with 2% ammonia to afford 580 mg (97%) of desired product. The pure product was treated with 1.0M HCl in diethyl ether to yield 50 (ADL-01-0060-2) as the HCl salt. $^1$H NMR (HCl salt, DMSO-$d_6$) δ 2.0 (br, m, 4H, —$CH_2CH_2$—), 2.7 (br, s, 3H, —$NCH_3$), 3.5 (br, S, (—$SO_2CH_3$)$_2$), 6.2 (br, d. 1H, —CH), 7.2-7.5 (complex, 9H, aromatic). MS (FAB) m/z 493. Anal. (C,H,N) $C_{23}H_{31}N_3O_5S_2.HCl.0.25\ H_2O$.

EXAMPLE 91

2-(N-methylsulfonamido-2-aminophenyl)-N-methyl-N-[(1S)-1-phenyl-2-(1-pyrrolidinyl)ethyl]acetamide; ADL-01-0075-O To a solution of 50 (500 mg; 1.0 mmol) in 6 mL of 2:1 MeOH:THF was added 4.0 mL of 1.0M NaOH. The solution was stirred for 20 mm., after which TLC (95:5 methylene chloride:methanol w/2% ammonia) indicates the reaction is complete. The reaction was quenched with 10% HCl and washed with water and brine. The organic layer was dried over anh. sodium sulfate, filtered and concentrated in vacuo to give 38 1 mg of a brown solid. The crude product was purified by flash chromatography using a stepwise gradient of 2% to 4% methanol: methylene chloride with 2% ammonia to afford 326 mg (80%) of desired product. The pure product was treated with 1.0M HCl in diethyl ether to yield 51 (ADL-01-0075-O) as the HCl salt. $^1$H NMR (HCl salt, CDCl$_3$) δ 2.0 (br, m, 4H, —$CH_2CH_2$—), 2.9 (br, s, 3H, —$NCH_3$), 3.0 (s, 3H, —$SO_2CH_3$), 6.3 (br, m, 1H, —CH), 7.0-7.2 (complex, 8H, aromatic), 7.5 (br, d, 1H, aromatic). MS (FAB) m/z 415. Anal. (C,H,N) $C_{22}H_{29}N_3O_3S.HCl.0.25H_2O$.

EXAMPLE 92

2-(2-Amino4,5-dichlorophenyl)-N-methyl-N-[(1S)-1-phenyl-2-(1-pyrrolidinyl)ethyl]acetamide; ADL-01-0035-4

To a solution of 32 (495 mg; 1.0 mmol) in 25 mL of abs. EtOH was added 50 mg of 10% 25 Pd/C. The mixture was placed on a Parr apparatus under 10 psi of hydrogen. After 1 h, TLC (95:5 methylene chloride:methanol) indicates no starting material remains. The mixture was filtered through a Celite plug and basified with aq. ammonium hydroxide. The solvent was concentrated in vacuo to get a residue which was dissolved in EtOAc and washed repeatedly with water. The organic layer was dried over anh. sodium sulfate, filtered and concentrated to give 200 mg of crude free base. The crude product was treated with 1.0M HCl in diethyl ether and dried in a vacuum oven @ 80 degrees overnight to recover 120 mg (30%) of 52 (ADL-01-0035-4) as the HCl salt. $^1$H NMR (HCl salt, CDCl$_3$) δ 1.6-1.7 (br, m, 4H, —$CH_2CH_2$—), 2.7 (s, 3H, —$NCH_3$), 5.9-6.1 (br, m, 1H, —CH), 7.1-7.2 (complex, 7H, aromatic). MS (FAB) m/z 406. Anal. (C,H,N) $C_{21}H_{25}N_3OCl_2.HCl.1.5H_2O$.

EXAMPLE 93

2-(N,N-Dimethysulfonamido-2-amino-4,5-dichlorophenyl)-N-methyl-N-[(1S)-1-phenyl-2-(1-pyrrolidinyl)ethyl]acetamide; ADL-01-0050-3

Same procedure as 50 using 223 mg (0.54 mmol) of 52, 0.5 mL (6.4 mmol) of MsCl, 2.0 mL (14.3 mmol) of triethylamine and 25 mL of dry methylene chloride. The crude product was purified by flash chromatography using a stepwise gradient of 1% to 3% MeOH: methylene chloride to yield 150 mg (49%) of pure product which was treated with 1.0M HCl in diethyl ether to give 53 (ADL-01-0050-3) as the HCl salt. $^1$H NMR (HCl salt, CDCl$_3$) δ 2.0 (br, m, 4H, —$CH_2CH_2$—), 2.8 (s, 3H, $NCH_3$), 3.3 (d, 6H, —($SO_2CH_3$)$_2$), 6.2 (br, m, 1H, —CH), 7.0-7.1 (complex, 2H, aromatic), 7.3 (complex, 5H, aromatic). MS (FAB) m/z 562. Anal. (C,H,N) $C_{23}H_{29}N_3O_5S_2Cl_2.HCl.0.5H_2O$.

EXAMPLE 94

2-(2-Amino,α,α,α-Trifluoro-4-toly)-N-methyl-N-[(1S)-1-phenyl-2-(1-pyrrolidinyl)ethyl]acetamide, ADL-01-0068-5

Same procedure as 49 using 710 mg(1.6 mmol) of 37, 0.5 mL (16.3 mmol) of hydrazine hydrate in 50 mL of EtOH. The recovered product, 650 mg (98% crude recovery) was not purified any further. A small amount of the desired product was treated with 10M HCl in diethyl ether to form 54 (ADL-01-0068-5) as the HCl salt. 1H NMR (HCl salt, CDCl$_3$) δ 2.0 (br, m, 4H, —$CH_2CH_2$—), 2.9 (br, s, 3H, —NCH$_3$), 6.3 (br, m, 1H, —CH), 7.2-7.5 (complex, 8H, aromatic). MS (FAB) m/z 405. Anal. (C,H,N) C$_{22}$H$_{26}$N$_3$OF$_3$.1.5HCl.

EXAMPLE 95

2-(2-N,N-Dimethylsulfonamido-2-amino-α,α,α-trifluoro-4-tolyl)-N-methyl-N-[(1S)-1-phenyl-2-(1-pyrrolidinyl)ethyl]acetamide: ADL-01-0069-3

Same procedure as 50 using 100 mg (0.24 mmol) of 54, 0.2 mL (2.4 mmol) of MsCl, 0.8 mL (6.3 mmol) of triethylamine and 13 mL of dry methylene chloride. The crude product was purified by flash chromatography using a stepwise gradient of 1% to 5% MeOH: methylene chloride to yield 110 mg (80%) of desired product. A small amount of compound was treated with 1.0M HCl in diethyl ether to give 55 (ADL-01-0069-3) as the HCl salt. 1H NMR (HCl salt, CDCl$_3$) δ 2.0 (br, m, 4H, —CH$_2$CH$_2$—), 2.9 (s, 3H, —NCH$_3$), 3.3 (d, 6H, —(SO$_2$CH$_3$)$_2$), 6.3 (br, m, 1H, —CH), 7.1-8.0 (complex, 8H, aromatic). MS (FAB) m/z 497. Anal. (C,H, N) C$_{24}$H$_{30}$N$_3$OF$_3$S$_2$.HCl.0.5H$_2$O.

EXAMPLE 96

2-(N-Methylsulfonamido-2-amino-α,α,α-trifluoro-4-tolyl)-N-methyl-N-[(1S)-1-phenyl-2-(1-pyrrolidinyl)ethyl]acetamide; ADL-01-0077-6

Same procedure as 51 using 51 mg (0.1 mmol) of 55, 30 mL of 1.0M NaOH and 1.9 mL of 2:1 MeOH:THF. The crude product was purified by flash chromatography using a stepwise gradient of 1% to 5% MeOH: methylene chloride with 2% ammonia to yield 27 mg (63%) of pure product which was treated with 1.0M HCl in diethyl ether to form 56 (ADL-01-0077-6) as the HCl salt. $^1$H NMR (HCl salt, CDCl$_3$) δ 2.0 (br, m, 4H, —CH$_2$CH$_2$—), 2.9 (br, s, 3H, —NCH$_3$), 3.1 (br, s, 3H, —SO$_2$CH$_3$), 7.1-7.3 (complex, 8H, aromatic). MS (FAB) m/z 483. Anal. (C,H,N) C$_{23}$H$_{28}$N$_3$O$_3$SF$_3$.HCl.0.25H$_2$O.

EXAMPLE 97

2-(2-Aminophenyl)-N-methyl-N-[(1S)-1-phenyl-2-(1-pyrrolidinyl)ethyl]acetamide; ADL-01-0089-1

Same procedure as 49 using 2.6 g (7.1 mmol) of 40, 2.5 mL (80.2 mmol) of hydrazine hydrate in 70 mL of EtOH. The recovered product, 1.8 g was purified by flash chromatography using a stepwise gradient of 1% to 9% MeOH: methylene chloride with 2% ammonia to yield 1.1 g (47%) of pure product which was treated with 1.0M HCl in diethyl ether to give 57 (ADL-01-0089-1) as the HCl salt. $^1$H NMR (free base, CDCl$_3$) δ 1.7-1.9 (br, m, 4H, —CH$_2$CH$_2$—), 2.7 (s, 3H, —NCH$_3$), 6.1 (br, m, 1H, —CH), 6.5-6.8 (complex, 3H, aromatic), 7.0 (m, 2H, aromatic), 7.3 (complex, 4H, aromatic. MS (FAB) m/z 337. Anal. (C,H,N) C$_{21}$H$_{27}$N$_3$O.2HCl.0.5H$_2$O.

EXAMPLE 98

2-(4-Aminophenyl)-N-methyl-N-[(1S)-1-phenyl-2-(1-pyrrolidinyl)ethyl]acetamide; ADL-01-0103-0

Same procedure as 49 using 2.3 g (6.3 mmol) of 39, 2.4 mL (75.4 mmol) of hydrazine hydrate 10 in 70 mL of EtOH. The recovered product, 1.7 g was purified by flash chromatography using a stepwise gradient of 2% to 3% MeOH: methylene chloride with 2% ammonia to yield 1.53 g (73%) of pure product. A small amount of compound was treated with 1.0M HCl in diethyl ether to give 58 (ADL-01-0103-0) as the HCl salt. $^1$H NMR (free base, CDCl$_3$) δ 1.8 (br, m, 4H, —CH$_2$CH$_2$—), 2.7 (s, 3H, —NCH$_3$), 6.1 (br, m, 1H, —CH), 6.7 (m, 2H, aromatic), 7.0 (d, 2H, aromatic), 7.3 (complex, 5H, aromatic). MS (FAB) m/z 337. Anal. (C,H,N) C$_{21}$H$_{27}$N$_3$O.2HCl.0.75H$_2$O.

EXAMPLE 99

2-(N,N-Dimethylsulfonamido-3-aminophenyl)-N-methyl-N-[(1S)-1-phenyl-2-(1-pyrrolidinyl)ethyl]acetamide ADL-01-0112-1

Same procedure as 50 using 500 mg (1.5 mmol) of 57, 1.1 mL (14.8 mmol) of MsCl, 3.0 mL (22.2 mmol) of triethylamine and 8.0 mL of dry methylene chloride. The crude product was purified by flash chromatography using a stepwise gradient of 1% to 4% MeOH: methylene chloride with 2% ammonia to yield 308 mg (42%) of pure product. A small amount of compound was treated with 1.0M HCl in diethyl ether to give 59 (ADL-01-0112-1) as the HCl salt. $^1$H NMR (free base, CDCl$_3$) δ 1.8 (br, m, 4H, —CH$_2$CH$_2$—), 2.8 (s, 3H, —NCH$_3$), 3.4 (s, 6H, —(SO$_2$CH$_3$O$_2$), 6.1 (br, m, 1H, —CH), 7.0-7.5 (complex, 9H, aromatic). MS (FAB) m/z 493. Anal. (C,H,N) C$_{23}$H$_{31}$N$_3$O$_5$S$_2$.HCl

EXAMPLE 100

2-(N,N-Dimethylsulfonamido-4-aminophenyl)-N-methyl-N-[(1S)-1-phenyl-2-(1-pyrrolidinyl)ethyl]acetamide; ADL-01-0127-9

Same procedure as 50 using 400 mg (1.2 mmol) of 58, 0.55 mL (7.1 mmol) of MsCl, 1.6 mL (11.8 mmol) of triethylamine and 12.0 ml of dry methylene chloride. The crude product was purified by flash chromatography using a stepwise gradient of 2% to 5% MeOH: methylene chloride with 2% ammonia to yield 395 mg (68%) of pure product. The compound was treated with 1.0M HCl in diethyl ether to give 60 (ADL-01-0127-9) as the HCl salt. $^1$H NMR(free base, CDCl$_3$) δ 1.8 (br, m, 4H, —CH$_2$CH$_2$—), 2.8 (s, 3H, —NCH$_3$), 3.4 (s, 6H, —(SO$_2$CH$_3$)$_2$), 6.1 (br, m, 1H, —CH), 7.0-7.5 (complex, 9H, aromatic. MS (FAB) m/z 493. Anal. (C,H,N) C$_{23}$H$_{31}$N$_3$O$_5$S$_2$.HCl.0.25H$_2$O.

EXAMPLE 101

2-(2-Hydroxyphenyl)-N-methyl-N-methyl-N-[(1S)-1-phenyl-2-(1-pyrrolidinyl)ethyl]acetamide; ADL-01-0061-0

To a solution of 34 (700 mg; 1.8 mmol) in 10 mL of dry methylene chloride @ −78 degrees was added 10.8 mL (10.8 mmol; 1.0M solution of BBr$_3$ in methylene chloride) over 15 minutes. The reaction mixture was allowed to warm to room temperature and stir overnight. TLC (95:5 methylene chloride: MeOH w/2% ammonia) indicated no starting material remained. The reaction was quenched with the addition of MeOH at 0 degrees. After 30 minutes, 3N HCl was added and the mixture was stirred for 30 minutes (white precipitate seen). The mixture was made neutral with sat. bicarbonate and extracted with methylene chloride (3×100 mL). The organic layer was dried over anh. sodium sulfate, filtered and concentrated in vacuo to give 610 mg of crude product. The crude product was purified by flash chromatography using a stepwise gradient of 2% to 3% MeOH: methylene chloride to yield 500 mg (82%) of pure product. The product was treated with 1.0M HCl in diethyl ether to give 61 (ADL-01-0061-0) as the HCl salt. $^1$H NMR (free base, CDCl$_3$) δ 1.7 (br, m, 4H, —CH$_2$CH$_2$—), 2.9 (s, 3H, —NCH$_3$), 6.1 (br, m, 1H, —CH), 6.8-7.4 (complex, 9H, aromatic). MS (FAB) m/z 338. Anal. (C,H,N) C$_{21}$H$_{26}$N$_2$O$_2$.HCl.0.5H$_2$O.

EXAMPLE 102

N-Methyl-N-[(1S)-1-phenyl-2-((3S)-3-hydroxypyrrolidine-1-yl)ethyl]-3,4,5-trimethoxyphenylacetamide HCl (A)

ADL-01-140-2

To a solution of 3,4,5-trimethoxyphenylacetic acid (1.0 g, 4.43 mmol) in 10 mL of CH$_2$Cl$_2$ under a nitrogen atmosphere was added pyridine (0.12 g, 1.5 mmol) and N,N-diisopropylethylamine (Hunig's Base) (0.57 g, 4.43 mmol). The reaction mixture was stirred at this temperature and a solution of the diamine1 (0.65 g, 3.0 mmol) in 10 mL of CH$_2$Cl$_2$ was added and the stirring was continued while warming to room temperature for 20 h. The reaction mixture was poured onto an aqueous saturated solution of NaHCO$_3$ and the mixture was stirred for 30 mm. The organic layer was separated and dried over anhydrous NaHCO$_3$. After removal of the solvent, the product was purified on a silica gel column [solvent system: CHCl$_3$: CH$_3$OH:28% NH$_4$OH (98:2:2)}. The free base was converted to the HCl 0.64 g (46%) as light pink solid; mp 230-232° C.; $^1$H—NMR (200 MHz, CDCl$_3$) δ 2.20 (m, 4H), 2.85 (s, 3H), 300-4.30 (m, 5H), 3.70 (ms, 9H), 4.50 (m, 2H), 5.30 (d, J=1.50 Hz, 1H), 6.50 (m, 3H), 7.28 (m, 5H). Anal. Calcd for C$_{24}$H$_{32}$N$_2$O$_5$.HCl.0.25H$_2$O: C, 61.40; H, 7.19; N, 5.97. Found: C, 61.36; H, 6.84; 8.96; N, 5.91.

The structure of the compound is shown hereunder.

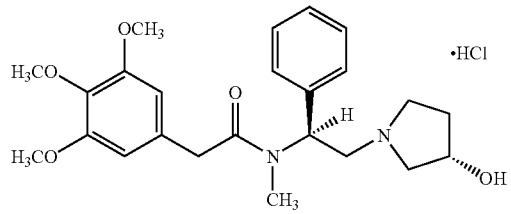

Compounds of Formula IV

Intermediates

The following intermediates were prepared

Synthesis of Diamine 3

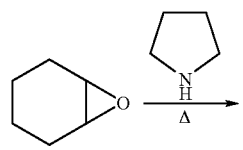

-continued

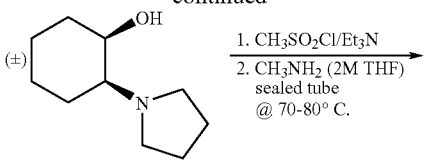

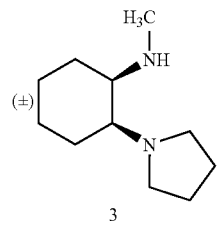

(±)-trans-2-Pyrrolidinyl-N-methylcyclohexylamine (3)

The racemic diamine (3) was prepared by a number of procedure reported in the literature.[10,11] Alternatively, the amine was also prepared from cyclohexene oxide (1) following the procedure described in Scheme I and the literature[12] in 70% overall yield as brown oil. A sample was purified by the distillation (b.p. 75-82° C./1.0 mm, lit.[2] b.p. 76-80° C./1.2 mm); $^1$H—NMR (200 MHz, CDCl$_3$) δ 1.04-1.36 (m, 4H), 1.49-1.89 (m, 8H), 2.18 (d, J=5.0 Hz, 1H), 2.52 (s, 3H), 2.56-2.70 (m, 4H), 2.80-293 (m, 1H), 7.75 (bs, 1H). The corresponding chiral amine (3) could be prepared following the literature procedures.

Ref.

(10) Szmuszkovicz, J.; Von Voigtlander, P. F. *J. Med. Chem.* 1982, 25, 1125-1126.

(11) DeCosta, B.; George, C.; Rothman, R. B.; Jacobson, A. E.; Rice, K. E. FEBS Lett. 1987, 223, 335-339.

(12) Freeman, J. P.; Michalson, E. T.; D'Andrea, S. V.; Baczynskyj, L.; Von Voigtlander, P. F.; Lahti, R. A.; Smith, M. W.; Lawson, C. F.; Scahill, T. A.; Mizsak, S. A.; Szmuszkovicz, J. *J. Med. Chem.* 1991, 34, 1891-35 1896.

Synthesis of Arylacetamides

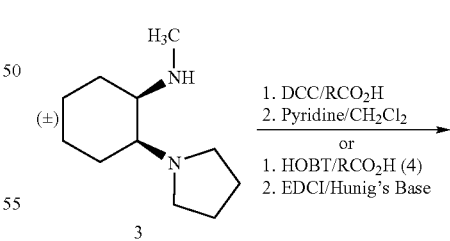

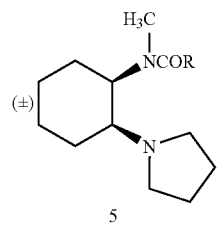

General Procedure for the Operation of Arylacetamides (±) 5 HCl

To a stirred solution of aryl acetic acid (4) (1.5 mmol) in 20 mL of dry $CH_2Cl_2$ was added pyridine (0.5 mmol) at 0→5° C. under a nitrogen atmosphere. N,N'-Dicyclohexylcarbodiimide (2.0 mmol was added in one portion and the reaction mixture was continued stirring for 30 min while warming to room temperature. A solution of the (±) 3 (1.0 mmol) in 10 mL of dry $CH_2Cl_2$ was added and the progress of the reaction was monitored by TLC in a solvent system corresponding to $CHCl_3:CH_3OH:28\%$ $NH_4OH$ (93:5:2). After disappearance of the diamine 3, the reaction mixture was quenched with saturated $NaHCO_3$ and stirring was continued for an additional 15 min. The precipitated N,N'-dicyclohexylurea (DCU) was removed by filtration and the filter cake was washed with additional amounts of $CH_2Cl_2$. The combined filtrate was evaporated to dryness and the residue was purified either on a silica gel column of using Chroatotran silica gel plates from the solvent system mentioned for each compound to give (±) 5 as free base. The hydrochloride salts were prepared from dissolving (±) 5 in a minimum amount of $CH_2Cl_2$ and addition of 2.0 equivalents of 1M etherial HCl. The solvents were removed under reduced pressure and the HCl salts were recrystallized from the solvents indicated below. The yields given below are for overall steps.

EXAMPLE 103

(±)-Trans-2-Nitro-N-methyl-N-[2-(1-pyrrolidinyl) cyclohexyl]phenylacetamide Hydrochloride [1±) 5a HCL]

ADL-01-0012-3

Prepared from 2-nitrophenylacetic acid [solvent for purification—$CH_2Cl_2:Ch_3OH:28\%$ $NH_2OH$ (98:2:2)]: yield 21% as a white solid (2-propanol); mp 267-269° C. (d); $^1H$ NMR (200 MHz, $CDCl_3$) δ 1.00-1.44 (m, 2H), 1.60-2.35 (m, 8H), 2.85 (m, 1H), 3.15 (s, 3H), 3.18-33.5 (m, 4H), 3.40 (m, 1H), 3.85 (m, 1H) 4.33 (dd, J=10.0 Hz, 2H) 4.64 (m, 1H), 7.35 (m, 1H), 7.56 (m, 2H), 8.05 (d, J=7.8 Hz, 1H), 11.02 (bs, 1H). Anal. Calcd for $C_{19}H_{27}N_3O_3.HCl$: C, 59.75; H, 7.39; Cl, 9.28; N, 11.00. Found: C, 59.98; H, 7.38; 8.96; N, 10.85.

EXAMPLE 104

(±)-trans-2-Amino-N-methyl-N-[2-(1-pyrrolidinyl) cyclohexyl]phenylacetamide Hydrochloride [(±) 5b HCl]

ADL-01-0014-9

To a solution of (±) 5a HCl (0.5 g. 1.31 mmol) in 30 mL of $CH_3OH$ was added 10% Pd/C (100 mg) and hydrogenated at 50 PSI in a Parr Apparatus at ambient temperature 3 h. The catalyst was removed by filtration through a celite pad and washed with hot CHOH and the combined filtrate was evaporated to dryness. The residue was recrystallized from 2-10 propanol to give (±) 5b HCl as a white solid, 0.45 g (95%); mp 213-215° C.; $^1H$ NMR (200 MHz, $CDCl_3$) δ 1.05-1.40 (m, 2H), 1.65-2.25 (m, 8H), 3.10 (s, 2H), 2.90-3.25 (m, 4H), 3.50 (d, J=1.20, 1H), 3.65 (m, 1H), 3.88 (m, 1H), 4.20 (d, J=12.5 Hz, 1H), 4.70 (m, 1H), 6.65 (m, 2H), 7.00 (m, 2H), 7.25 (bs, 2H). Anal Calcd for $C_{19}H_{29}N_3O.HCl.0.5H_2O$: C, 63.23; H, 8.66; N, 11.64. Found: C, 63.59; H, 8.76; N, 11.61.

EXAMPLE 105

(±)-trans-2-Nitro-4,5-dichloro-N-methyl-N-[2-(1-pyrrolidinyl)cyclohexyl], phenylacetamide Hydrochloride [(±) 5c HCl]

ADL-01-0015-6

The compound was prepared according to the literature method (DeCosta, B.; Linda, B.; Rothman, R. B.; Jacobson, A. E.; Bykov, V.; Pert, A.; Rice, K. E. FEBS Lett. 1989, 249, 178-182); $^1H$ NMR (200 MHz, $CDCl_3$) δ 1.55-2.30 (m, 8H), 3.10 (s, 3H), 2.85-3.(m, 4H), 7.70 (s, 1H), 8.13 (s, 1H). AnaL Calcd for $C_{19}H_{25}Cl_2N_3O_3.HCl$: C, 25 50.62; H, 5.81; N, 9.32. Found: C, 50.61; H, 5.61; N, 9.20.

EXAMPLE 106

(±)-trans-2-Amino-4,5-dichloro-N-methyl-N-[2-(1-pyrrolidinyl)cyclohexyl]-phenylacetamide Hydrochloride [(±) 5d HCl]

ADL-01-0016-4

Obtained from (±) 5c HCl following the literature procedure (DeCosta, B.; Linda, B.; Rothman, R. B.; Jacobson, A. E.; Bykov, V.; Pert, A.; Rice, K. E. FEBS Lett. 1989, 249, 178-182); $^1H$ NMR (200 MHz, $CDCl_3$) δ 1.10-1.40 (m, 4H), 1.48-2.20 (m, 8H), 3.00 (s, 3H), 3.10-3.30 (m, 4H), 3.55 (d, J=1.40 Hz, 1H), 3.85 (d, J=14.0 Hz, 1H), 4.50 (m, 1H), 6.75 (s, 1H). Anal. Calcd for $C_{19}H_{27}Cl_2N_3O.HCl0.75H_2O$: C, 52.54; H, 6.84; N, 9.67. Found: C, 52.561; H, 6.63; N, 9.33.

EXAMPLE 107

(±)-trans-2-Methanesulfonamido-N-methyl-N-[2-(1-pyrrolidinyl)cyclohexyl]-phenylacetamide Hydrochloride [(±) 5e HCl]

ADL-01-0025-5

To a solution of free base of (±) 5b (1.0 G, 3.2 mmol) in 40 mL of dry $CH_2Cl_2$ at 0° C. under a nitrogen atmosphere was added $Et_3N$ (1.86 g, 18.4 mmol). A solution of methanesulfonyl chloride (1.14 g, 9.92 mmol) in 15 mL of dry $CH_2Cl_2$ was added dropwise within 15 min. After 2 h at room temperature TLC [solvent system: $CHCl_3:CH_3OH: 28\%$ $NH_4OH$ (93:5:2)]showed starting material was still present. Additional amounts of $Et_3N$ (1.86 g) and methanesulfonyl chloride (1.14 g) were added and stirring was continued for another 2 h. By this time no starting material was present in the reaction mixture. After the mixture was diluted with 40 mL $CH_2Cl_2$, it was washed with saturated $NaHCO_3$, water, saturated salt solution, and dried over anhydrous $Na_2SO_4$. Removal of solvent under reduced pressure gave the bis-sulfonamide as a brown foam which was used directly in the following hydrolysis. To a solution of bis-sulfonamide (1.0 g, 2.12 mmol) in 60 mL of $CH_3OH$:THF (2:1) was added 10 M aqueous NaOH (0.96 mL, 9.6 mmol). The mixture was stirred at room temperature for 30 min and the acidified with 1N HCl. The solvent was evaporated under reduced pressure and the residue was redissolved in $CH_2Cl_2$. The $CH_2Cl_2$ layer was then washed with 5% $NaHCO_3$, saturated salt solution, and dried over anhydrous $Na_2SO_4$. Removal of solvent under reduced pressure chromatography on a silica gel column [solvent system: $CH_2Cl_2:CH_3OH:28\%$ $NH_4OH$ (95:5:2)] gave the monosulfonamide (free base) as an oil; $^1H$ NMR (2.00 MHz, CDCl$_3$) δ 1.05-1.95 (m, 12H), 2.45-2.80 (m, 5H), 2.95 (s, 3H), 3.10 (s, 3H), 3.50 (d, J=13.8 Hz, 1H), 3.65 (m, 1H), 3.85 (d, J=14.0 Hz, 1H), 4.45 (m, 1H), 7.05 (m, 1H), 7.15 (m, 2H), 7.45 (d, J=8.5 Hz, 1H). The hydrochloride salt was prepared by dissolving the free base CH$_2$Cl$_2$ and adding 1.2 equivalents of 1M etherial HCl and recrystallizing from 2-propanol to give (±) 5e HCl as a beige colored solid, 0.37 g (38%); mp 229-231° C.; $^1$H NMR (200 MHz, CDCl$_3$) δ 1.10-2.20 (m, 12H), 2.90-3.20 (m, 1H), 7.05-7.30 (m, 3H), 7.60 (d, J=8.0 Hz, 1H), 8.90 (bs, 1H). Anal. Calcd for C$_{20}$H$_{31}$N$_3$O$_3$S.HCl.0.25H$_2$O: C, 55.28; H, 7.54; N, 9.67. Found: C, 55.40; H, 7.39; N, 949.

Ref.
(13) Li, C.-S.; Black, W. C.; Chan, C.-C.; Ford-Hutchinson, A. W.; Gauthier, J.-Y.; Gordon, R.; Guay, D; Kargman, S.; Lau, C. K.; Mancini, J.; Ouimet, N.; Roy, P.; Vickers, P.; Wong, E.; Young, R. N.; Zamboni, R.; Prasit, P. *J. Med. Chem.* 1995, 38,4897-4905.

EXAMPLE 108

N-[2-(±)-trans-N-Methyl-N-[2-(1-pyrrolidinyl)cyclohexyl]-phenylacetamido]glycine Hydrochloride (±) 5f HCl]

ADL-01-0028-9

To a stirred solution of (±) 5b (free base, 1.0 g, 3.2 mmol) in 15 mL of dry DMF at room temperature under a nitrogen atmosphere was added 95% NaB (0.083 g, 3.3 mmol). After stirring at room temperature for 30 min, the turbid solution was added to a stirred solution of tert-butyl bromoacetate (0.66 g, 3.4 mmol) in 10 mL of dry DMF. The reaction mixture continued stirring for 72 hr; however TLC of the reaction mixture [solvent system: CHCl$_3$:CH$_3$OH:28% NH$_4$OH (93:5:2)] showed starting material was still present. The solvent was removed under reduced pressure and the residue was partitioned between CH$_2$Cl$_2$/water. The product was purified on a silica gel column from CH$_2$Cl$_2$:CH$_3$OH (9:1) and was recrystallized from CH$_2$Cl$_2$:Et$_2$O (1:1) to give the corresponding tert-butyl ester, 0.16 (12%); $^1$H NMR (200 MHz, CDCl$_3$) δ 1.05-1.35 (m, 4H), 1.35 (s, 9H), 1.55-2.20 (m, 8H), 2.92 (b, 4H), 3.12 (s, 3H), 3.45 (m, 1H), 3.60 (d, J=14.0 Hz, 2H), 3.78 (bt, 2H), 3.95 (m, 1H), 5.75 (b, 1H), 6.38 (d, J=6.5 Hz, 1H), 6.60 (t, J=5.5 Hz, 1H), 7.00 (m, 2H). The starting material was also recovered in 50% yield.

The tert-butyl ester (0.16 g, 0.372 mmol) was suspended in 10 mL of 4N aqueous HCl. One drop of anisole was added and the mixture was stirred at room temperature for 24 h. The solvent was evaporated under reduced pressure and the residue was redissolved in CH$_3$CN and filtered. The filtrate was evaporated under reduced pressure and the residue was recrystallized from 2-propanol:ether (1:1) to give (±) 5f HCl as a white solid, 0.070 g (42%); mp 212-214° C. (d); $^1$H NMR (200 MHz, DMSO-d$_6$) δ 1.15-2.25 (m, 12H), 2.90 (m, 1H), 3.05 (s, 3H), 3.14-3.70 (m, 6H), 3.85 (bs, 2H), 4.55 (b, 1H), 6.37 (d, J=6.0 Hz, 1H). 6.55 (t, J=5.0 Hz, 1H), 6.95 (m, 2H), 9.80 (b, 1H). Anal. Calcd for D$_{21}$H$_{31}$N$_3$O$_3$.HCl.H$_2$O: C, 58.93; H, 8.00; N, 9.81. Found: C, 58.79; H, 7.64; N, 9.43.

EXAMPLE 109

(±)-trans-4-Trifluoromethyl-N-methyl-N-[2-(1-pyrrolidinyl)cyclohexyl]-phenylacetamide Hydrochloride [(±) 5g HCl]

ADL-01-0066-9

To a solution of 4-trifluoromethylphenyl acetic acid (1.45 g, 7.08 mmol) in 10 mL of dry CH$_2$Cl$_2$ under a nitrogen atmosphere was added 1-hydroxybenzotriazole hydrate (HOBT) (0.95 g, 7.08 mmol) and stirred. The reaction mixture was cooled to 0→4 5° C. and solid EDCI ([1-(3-dimethylaminopropyl)-3-ethyl-carbodiimide HCl]) (1.35 g, 7.08 mmol) was added and stirred at this temperature for 30 mm. A solution of (±) 3 (1.0 g, 5.48 mmol) in 10 mL of dry CH$_2$Cl$_2$ was added followed by N,N-diisopropylethylamine (Hunig's Base) (0.915 g, 7.08 mmol). The reaction mixture was stirred for 24 h while warming to room temperature. The reaction mixture was then poured onto excess of ice-cold saturated aqueous NaHCO$_3$ solution and stirred for 30 min. After dilution with CH$_2$Cl$_2$, the organic layer was separated, washed with saturated salt solution, and dried over anhydrous Na$_2$SO$_4$. Removal of solvent gave a brown oil which was chromatographed on a silica gel column [solvent system: CH$_2$Cl$_2$:CH$_2$OH:28% NH$_4$OH (99:1:2) to give the desired product as free base. The hydrochloride salt was prepared from 1M etherial HCl and recrystallized from CH$_2$CL$_2$:Et$_2$0 (1:1) to give (±) 5g HCl as a cream colored solid, 0.68 g (30%); 213-215° C.; $^1$H NMR (200 MHz, CDCl$_3$) δ 1.02-1.47 (m, 4H), 1.52-2.22 (m, 8H), 2.75-2.90 (m, 2H), 2.94 (s, 3H), 3.07 (m, 1H), 3.37 (m, 1H), 3.62 (d, J=15.0 Hz, 1H), 3.77 (m, 1H), 4.17 (d, J=15.0 Hz, 1H), 4.57 (m, 1H), 7.30 (d, J=8.0 Hz, 2H), 7.38 (d, J=8.0 Hz, 2H). Anal. Calcd for C$_{20}$H$_{27}$F$_3$N$_2$O.HCl.0.25H$_2$O: C, 58.68; H, 7.02; N, 6.84. Found: C, 58.68; H, 6.84; N, 6.69.

Nitration of 4-trifluoromethylphenyl acetic acid:
General Procedure:

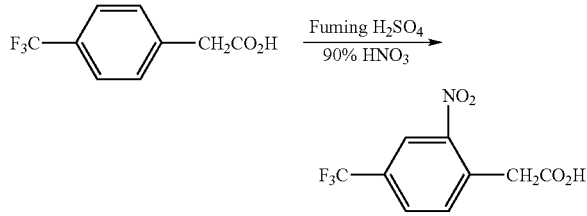

Preparation of 2-nitro-4-trifluoromethylphenyl Acetic Acid [4,R=2-NO$_2$-(4-CF$_3$)—C$_6$H$_4$CH$_2$]

To a solution of 4-trifluoromethylphenyl acetic acid (2.5 g, 12.25 mmol) in 8 mL of glacial acetic acid at 0° C. under an anhydrous atmosphere was added 5 mL of fuming H$_2$SO$_4$ (11% SO$_3$) (caution!) followed by cautious addition of 90% HNO$_3$ (3.5 mL, 73.14 mmol) within 10 mm. The reaction mixture was then stirred at room temperature for 2 h and poured into ice-water. The resulting solid was filtered and washed with cold deionized water to give the desired product after drying as off-white solid, 2.5 g (82%); $^1$H NMR (200 MHz, CDCl$_3$) δ 4.02 (s, 2H), 7.41 (d, J=8.0 Hz, 2H), 7.74 (d, J=8.0 Hz, 2H), 8.28 (s, 1H). The product was used directly in the following reactions.

EXAMPLE 110

(±)-trans-2-Nitro-4-trifluoromethyl-N-methyl-N-[2-(1-pyrrolidinyl)cyclohexyl]-phenylacetamide Hydrochloride [(±) 5h HCl]

ADL-01-0065-1

Prepared from 2-nitro-4-trifluoromethylphenyl acetic acid following the procedure described in Example II to give (±) 5h HCl as cream colored solid in 56% yield; mp 259-261° C. (d); $^1$H NMR (200 MHz, CDCl$_3$) δ 1.10-1.42 (m, 4H), 1.51-2.25 (m 8H), 2.95-3.25 (m, 3H), 3.14 (s, 3H), 3.40 (m, 1H), 3.90 (m. 1H), 4.35 (d, J=13.8 Hz, 1H), 4.55 (d, J=14.0 Hz, 1H), 4.60 (m, 1H), 7.80 (dd, J=7.8 Hz, 2H), 8.25 (s, 1H). Anal. Calcd for $C_{20}H_{26}F_3N_3O_3$.HCl.0.25H$_2$O: C, 52.86; H, 6.10; N, 9.25. Found: C, 52.85; H, 6.02; N, 9.13.

EXAMPLE 111

(±)-trans-2-Amino-4-trifluoromethyl-N-methyl-N-[2-(1-pyrrolidinyl)cyclohexyl]-phenylacetamide Hydrochloride [(±) 5i HCl]

ADL-01-0080-0

To a solution of free base 4h (0.4 g, 0.97 mmol) in 20 mL of absolute alcohol was added 2 ml of hydrazine hydrate and the reaction mixture was stirred at 50° C. under a nitrogen atmosphere. Raney®nickel (50% slurry in water) was added slowly and the progress of the reaction was monitored on TLC plates [solvent system: CHCl$_3$:CH$_3$OH:28% NH$_4$OH (99:1:2)]. If needed, more of the Raney®nickel was added to the reaction mixture. When the reaction was completed, an excess of Raney®nickel was introduced to decompose the hydrazine hydrate. The reaction mixture was filtered through a celite pad and the pad was washed with hot CH$_3$OH. The filtrate was evaporated to dryness. The residue was purified on a silica gel column [solvent system: CHCl$_3$: CH$_3$OH:28% NH$_4$OH (99:1:2)] and the hydrochloride salt was prepared from 1M etherial HCl. Recrystaflization from CH$_2$Cl$_2$:Et$_2$O (2:1) gave (±) 5i HCl as a white solid, 0.2 g (48%); mp 248-250° C. (d); $^1$H NMR (200 MHz, DMSO-d$_6$) δ 1.15-1.18 (m, 12H), 3.00 (s, 3H), 3.15-4.10 (m, 7H), 4.50 (m, 1H), 6.80 (d, J=7.8 Hz, 1H), 6.92 (s, 1H), 7.10 (d, J=8.0 Hz, 1H), 10.0 (bs, 1H). Anal. Calcd for $C_{20}H_{28}F_3N_3O$.HCl.0.5H$_2$O: C, 56.01; H, 7.05; N, 9.80. Found: C, 55.70; H, 7.03; N, 9.65.

EXAMPLE 112

(±)-trans-2-Bismethanesulfonamido-4-trifluoromethyl-N-methyl-N-[2-(1-pyrrolidinyl)cyclohexyl]-phenylacetamide Hydrochloride [(±) 5j HCl]

ADL-01-0118-8

The compound was prepared from free base (±) 5i (0.5 g, 1.30 mmol) following the procedure described in the first part of the preparation of (±) 5e. The bismethanesulfonamide was purified on a silica gel column [solvent system: CH$_2$Cl$_2$:CH$_3$OH:28% NH$_4$OH (96:2:2)] to give the desired product as a foam. The hydrochloride salt was prepared from 1M etherial HCl and recrystallized from 2-propanol:Et$_2$O (1:1) to give (±) 5j HCl as a beige colored solid, 0.23 g (30%); mp 224-226° C. (d); $^1$H NMR (200 MHz, CDCl$_3$) δ 1.12-1.51 (m, 4H). 1.53-2.24 (m, 8H), 1.82-3.17 (m, 2H), 2.98 (s, 3H), 3.32-3.56 (m, 2H), 3.28 (s, 3H), 3.33 (s, 3H), 3.77 (m, 1H), 3.97 (d, J=14.0 Hz, 1H). Anal. Calcd for $C_{22}H_{32}F_3N_3O_3S_2$.HCl: C, 45.87; H, 5.77; N, 7.29. Found: C, 45.53; H, 5.81; N, 7.00.

EXAMPLE 113

(±)-trans-2-Methanesulfonamido-4-trifluoromethyl-N-methyl-N-[2-(1-pyrrolidinyl)cyclohexyl]-phenylacetamide Hydrochloride [(±) 5k HCl]

ADL-01-0137-8

To a solution of (±) 5j HCl (0.16 g, 0.23 mmol) in 9 mL of CH$_3$OH:THF (2:1) at room temperature was added 0.12 mL of 10M aqueous NaOH and the mixture was stirred for 30 min. The reaction mixture was neutralized with 1N HCl and evaporated to dryness. The residue was redissolved in CH$_2$Cl$_2$ and basified with a saturated aqueous solution of NaHCO$_3$. The organic layer was separated, washed with water, saturated salt solution, and dried over anhydrous Na$_2$SO$_4$. Removal of solvent under reduced pressure gave the product as a free base. The hydrochloride salt was prepared from 1M etherial HCl and recrystallized from CH$_2$Cl$_2$:Et$_2$O (1:1) to give (±) 5k HCl as a beige colored solid, 0.085 g (61%); 209-211° C. (d); $^1$H NMR (200 MHz, CDCl$_3$) δ 1.15-1.24 (m, 4H), 1.50-2.10 (m, 2H), 2.90-3.10 (m, 2H), 3.05 (s, 6H), 3.55 (m, 2H), 3.80 (m, 1H), 4.64 (m, 1H), 7.20 (dd, J=7.8 Hz, 2H), 7.88 (s, 1H), 9.00 (s, 1H). Anal. Calcd for $C_{21}H_{30}F_3N_3O_3S$.HCl.0.125H$_2$O: C, 50.42; H, 6.30; N, 8.40. Found: C, 50.62; H, 6.49; N, 8.00.

EXAMPLE 114

N-[2-(±)-trans-4-Trifluoromethyl-N-methyl-N-[2-(1-pyrrolidinyl)cyclohexyl]phenylacetamido]glycine Hydrochloride [(±) 5l HCl]

ADL-01-0130-3

To a solution of free base (±) 5i (0.767, 2.0 mmol) in 10 mL of anhydrous THF under a nitrogen atmosphere at 0° C. was added N,N-diisopropylethylamine (Hunig's Base) (1.55 g, 12.0 mmol). The reaction mixture was stirred at 0° C. for 15 min then bromoacetic acid t-butyl ester (1.95 g, 10.0 mmol) was added and the reaction mixture continued to stir while warming to room temperature for 72 h. The solvent was evaporated at reduced pressure and the residue was partitioned between CH$_2$Cl$_2$ and water. The organic layer was then washed with saturated NaHCO$_3$, saturated salt solution, and dried over anhydrous Na$_2$SO$_4$. Removal of solvent gave the crude product which was purified on a silica gel column [solvent system: CHCl$_3$,CH$_3$OH:28% NH$_4$OH (96:2:2)] to give the intermediate t-butyl ester 0.477 g (40%); $^1$H NMR (200 MHz, CDCl$_3$) δ 1.05-1.25 (m, 8H), 1.40 (s, 9H), 2.15-2.75 (m, 5H), 2.85 (s, 3H), 3.60 (m, 2H), 3.75 (d, J=4.0 Hz, 2H), 4.45 (m, 1H), 5.85 (m, 1H), 6.55 (s, 1H), 6.80 (d, J=7.5 Hz, 1H), 7.10 (d, J=7.8 Hz, 1H).

The above t-butyl ester (0.47 g, 0.77 mmol) was suspended in 10 mL of aqueous 4N HCl and 10 2-3 drops of anisole was added. The reaction mixture was stirred at room temperature for 72 h and filtered. The filtrate was evaporated to dryness, redissolved in CH$_3$CN, filtered again, and concentrated. Addition of the ether gave the product which was filtered, washed with ether, and dried to give (±) 5l HCl as a beige colored solid, 0.17 g (41%); mp 178-180° C. (d); MS (FAB) 442 (M+1); $^1$H NMR (200 MHz, CDCl$_3$) δ 1.05-2.20 (m, 12H), 2.75 (s, 3H), 2.90-15 3.25 (m, 5H), 3.30-3.55 (m, 2H), 3.70-4.35(m, 4H), 4.65 (m, iH), 6.72 (s, 1H), 6.80 (m, 1H), 6.9(d, J=7.7 Hz, 1H). Anal Calcd for $C_{22}H_{30}F_3N_3O_3\cdot HCl\cdot 0.125Et_2O$: C, 55.47; H, 6.67; N, 8.62. Found: C, 55.64; H, 7.06; N, 9.00.

EXAMPLE 115

(±)-trans-3-Trifluoromethyl-N-methyl-N-[2-(1-pyrrolidinyl)cyclohexyl]-phenylacetamide Hydrochloride [(±) 5m HCl]

ADL-01-0083-4

Following Example 2, (±) 5m HCl was prepared from 3-trifluoromethylphenyl acetic acid in 67% yield as a cream colored solid; mp 245-247° C.; $^1$H NMR (200 MHz, CDCl$_3$) δ 1.15-1.55 (m, 4H), 1.60-2.30 (m, 8H), 2.80-3.05 (m, 2H), 3.00 (s, 3H), 3.18 (m, 1H), 3.45 (m, 1H), 3.75 (d, J=15.0 Hz, 1H), 3.85 (m, 1H), 4.25 (d, J=14.8 Hz. 1H), 4.65 (m, 1H), 7.40 (m, 4H). Anal Calcd for $C_{20}H_{27}F_3N_2O\cdot HCl\cdot 0.25H_2O$: C, 58.68; H, 7.02; N, 6.84. Found: C, 58.46; H, 7.17; N, 6.69.

Nitration of 3-trifluoromethylphenyl Acetic Acid:

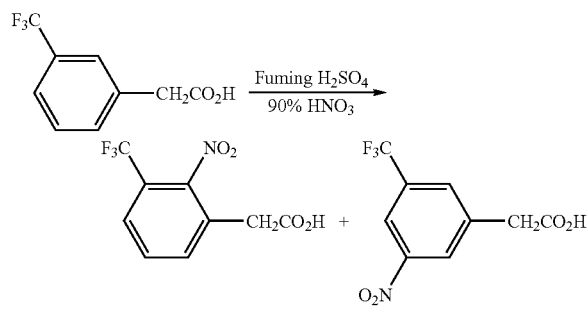

Preparation of 2-nitro-3-trifluoromethylphenyl Acetic Acid [4,R=2-NO$_2$(3-CF$_3$)—C$_6$H$_4$CH$_2$] and Preparation of 5-nitro-3-trifluoromethylphenyl Acetic Acid [4,R=5-NO$_2$(3-CF$_3$)—C$_6$H$_4$CH$_2$]

The nitration of 3-trifluorophenylacetic acid as shown earlier resulted in a 1:1 non-separable mixture of 2- and 5-nitro compounds in 66% yield. The structural assignments of the compounds were made on the basis of the $^1$H NMR spectrum. The mixture was used in the condensation reaction.

EXAMPLE 116

(±)-trans-5-Nitro-3-trifluoromethyl-N-methyl-N-[2-(1-pyrrolidinyl)cyclohexyl]-phenylacetamide Hydrochloride [(±) 5n HCl]and (±)-trans-2-Nitro-3-trifluoromethyl-N-methyl-N-[2-(1-pyrrolidinyl) cyclohexyl]-phenylacetamide Hydrochloride 5(±) 5o HCl]

ADL-01-0087-5 and ADL-01-0088-3

The compounds were prepared as shown in Example 109 and the mixture of 2- and 5-nitrophenylacetic acids to give the mixture of products. Initially the compounds were separated on a silica gel column [solvent system: CHCl$_3$: CH$_3$OH:28% NH$_{4\ OH}$ (96:2:2)] which resulted in the free base of the compounds as a pure mixture. The products were again purified on Chromatotran using a 4 mm silica gel plate [solvent system: CHCl$_3$ containing 2% NH$_4$OH]. The first product was isolated and converted to the hydrochloride salt and the salt was recrystallized from 2-propanol:ether (1:1) to give (±) 5n HCl as a cream colored solid in 10% yield; mp 236-238° C.; $^1$H NMR (200 MHz, CDCl$_3$) δ 1.15-1.55 (m, 4H, 1.65-2.30 (m, 8H), 2.85-3.20 (m, 3H), 3.10 (s, 3H), 3.40 (m, 1H), 3.70 (d, J=14.0 Hz, 1H), 3.85 (m, 1H), 4.60 (brd, 2H), 7.90 (s, 1H), 8.25 (s, 1H), 8.32 (s, 1H). Anal. Clcd for $C_{20}H_{26}F_3N_3O_3\cdot HCl$: C, 53.39; H, 6.05; N, 9.34. Found: C, 53.28; H, 6.06; N, 9.36.

The second product, (±) 5o HCl, was also isolated in 10% yield after the recrystallization of the hydrochloride salt from 2-propanol:ether (1:1) as a white solid; mp 243-245° C. (d); $^1$H NMR (200 MHz, CDCl$_3$) δ 1.10-1.50 (m, 4H), 1.55-2.20 (m, 8H), 2.90-3.20 (m, 3H), 3.10 (s, 3H), 3.44 (m, 1H), 3.65 (d, J=13.5 Hz, 1H), 3.90 (m, 1H), 4.65 (brd, 2H), 7.70 (s, 1H), 7.82 (s, 2H). Anal. Calcd for $C_{20}H_{26}F_3N_3O_3\cdot HCl\cdot H_2O$: C, 51.34; H, 6.25; N, 8.98. Found: C, 51.69; H, 6.24; N, 8.89.

EXAMPLE 117

(±)-trans-2-Trifluoromethyl-N-methyl-N-[2-(1-pyrrolidinyl)cyclohexyl]-phenylacetamide Hydrochloride [(±) 5p HCl]

ADL-01-0114-7

The compound was prepared from 2-trifluoromethylphenylacetic acid following Example 2. The hydrochloride salt was made from 1M etherial HCl and recrystallized from 2-propanol:ether (1:1) to give (±) 5p HCl in 20% yield as a white solid; mp 282-284° C. (d); $^1$H NMR (200 MHz, CDCl$_3$) δ 1.20-1.50 (m, 4), 1.55-2.30 (m, 8H), 3.85-3.04 (m, 2H), 3.08 (s, 3H), 3.10-3.27 (m, 1H), 3.40-3.60 (m, 1H), 3.90 (m, d, J=14.5 Hz, 2H), 4.26 (d, J 14.7 Hz, 1H), 4.63 (m, 1H), 7.26 (t, J=8.0 Hz, 1H), 7.45 (t, J=8.0 Hz, 1H), 7.60 (t, J=7.5 Hz, 2H). Anal. Clcd for $C_{20}H_{27}F_3N_3O\cdot HCl$: C, 59.33; H, 6.97; N, 6.92. Found: C, 59.28; H, 6.73; N, 6.84.

Nitration of 2-trifluoromethylphenyl Acetic Acid:

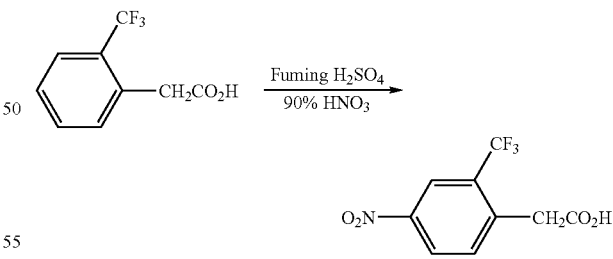

Preparation of 4-nitro-2-trifluoromethylphenyl Acetic Acid [4,R=4-NO$_2$(2-CF$_3$) C$_6$H$_4$CH$_2$]

The nitration of 2-trifluorophenylacetic acid as depicted in Scheme III gave mostly the corresponding 4-nitro derivative and only a trace amount of 6-nitro compound was detected in the proton NMR; $^1$H NMR (200 MHz, CDCl$_3$) δ 3.90 (s, 1H, 7.55 (d, J=8.4 Hz, 1H), 8.35 (dd, J=2.4, 8.0 Hz, 1H), 8.50 (d, J=2.4 Hz, 1H). The compound was used directly in the following coupling reaction.

EXAMPLE 118

(±)-trans-4-Nitro-2-trifluoromethy-N-methyl-N-[2-(1-pyrrolidinyl)cyclohexyl]-phenylacetamide Hydrochloride [(±) 5i HCl]

ADL-01-0116-2

The compound was prepared following the coupling method described in Example 109 from 4-nitro-2-trifluorophenylacetic acid. The hydrochloride salt was prepared by a known method and recrystallized from 2-propanol:ether (1:1) to give (±) 5q HCl as a beige colored solid in 37% yield; mp 265-267° C. (d); $^1$H NMR (200 MHz, CDCl$_3$) δ 1.15-1.45 (m, 4H), 1.50-2.30 (m, 8H), 2.85-3.20 (m, 3H), 3.05 (s, 3H), 3.45 (m, 1H), 3.90 (m, d, J=14.0 Hz, 2H), 4.60 (brd, 2H), 8.00 (d, J=8.0 Hz, 1H), 8.25 (dd, J=2.4, 8.0 Hz, 1H), 8,40 (d, J=2.4 Hz, 1H). Anal. Calcd for $C_{20}H_{26}F_3N_3O_3$.HCl: C, 53.39; H, 6.05; N, 9.34. Found: C, 53.29; H, 5.93; N, 30 9.17.

EXAMPLE 119

(±)-trans-4-Amino-2-trifluoromethyl-N-methyl-N-[2-(1-pyrrolidinyl)cyclohexyl]-phenylacetamide Hydrochloride [(±) 5r 2HCl]

ADL-01-0142-8

The compound was prepared from free base (±) 5q following the reduction procedure described for the preparation of (±) 5h. The free base was converted to di-hydrochloride from 1M etherial HCl and recrystallized from $CH_2Cl_2$:$CH_3OH$:$Et_2O$ (6:3:1) to give (±) 5r 2HCl as a white solid in 68% yield; mp 288-290° C. (d); $^1$H NMR (200 MHz, CDCl$_3$) δ 1.10-2.20 (m, 12H), 2.98 (s, 3H), 3.00-3.30 (m, 4), 3.50 (m, 1H), 3.80 (d, J=14.5 Hz, 1H), 4.20 (d, J=14.8 Hz, 1H), 4.50 (m, 1H), 7.50 (m, 3H). Anal. Calcd for $C_{20}H_{28}F_3N_3O$.2HCl: C, 52.64; H, 6.63; N, 9.21. Found: C, 52.67; H, 6.52; N, 9.06.

EXAMPLE 120

(±)-trans-N-Methyl-N-[2-(1-pyrrolidinyl)cyclohexyl] 2,2-diphenylacetamide Hydrochloride [(±) 5s HCl]

ADL-01-0013-1

The compound was prepared from diphenylacetic acid following the general procedure for the preparation of aryl acetamides. The hydrochloride salt was recrystallized from 2-propanol to give (±) 5s HCl as a white solid in 20% yield; mp 295-297° C. (d); $^1$H NMR (200 MHz, CDCl$_3$) δ 1.20-2.40 (m, 12H), 2.85-3.15 (m, 2H), 3.00 (s, 3H), 3.25-3.60 (m, 2H), 3.95 (m, 1H), 4.75 (m, 1H), 5.70 (s, 1H), 7.35 (m, 10H). Anal. Calcd for $C_{25}H_{32}N_2O$.HCl.0.25H$_2$O: C, 71.92; H, 8.09; N, 6.71. Found: C, 72.25; H, 8.40; N, 6.52.

EXAMPLE 121

(±)-trans-4-Methylsulfonyl-N-methyl-N-[2-(1-pyrrolidinyl)cyclohexyl]phenylacetamide Hydrochloride [(±) 5t HCl]

ADL-01-0071-9

The compound was prepared from 4-methylsulfonylphenylacetic acid to the method of Example 109 and the hydrochloride salt was recrystallized from CH$_2$Cl$_2$:Et$_2$O (1:1) to give (±) 5t HCl as a cream colored solid in 50% yield; mp 152-154° C. (d); $^1$H NMR (200 MHz, CDCl$_3$) δ 1.10-2.30 (m, 12H), 2.95 (s, 6H), 3.00-3.25 (m, 2H), 3.40 (m, 1H), 3.65 (d, J=14.5 Hz, 1H), 3.85 (m, 1H), 4.35 (d, J=14.0 Hz, 1H), 4.67 (m, 1H), 7.45 (d, J=8.0 Hz, 2H), 7.80 (d, J=8.0 Hz, 2H). Anal. Calcd for $C_{20}H_{30}N_2O_3S$.HCl.1.5H$_2$O: C, 54.35; H, 7.75; N, 6.34. Found: C, 54.20; H, 7.38; N, 6.15.

In a composition aspect, the kappa agonist compounds of the present invention are formulated into parenteral, local and topical formulations.

The compositions are formulated as injectables, as oral and rectal formulations for systemic administration, and for local and topical administration as creams, aqueous or non-aqueous suspensions, lotions, emulsions, suspensions or emulsions containing micronized particles, gels, foams, aerosols, solids and other suitable vehicles for application to the skin, eyes, lips and mucosa, as suppositories or creams for vaginal administration, and as combinations with bandages, patches, bioadhesives and dressings. The compounds may be formulated in combination with other agents, such as local anesthetics and other therapeutic agents. The other agents that may be mixed in the compositions are provided and administered prior to, simultaneously with or subsequent to administration of the compositions provided for the methods herein. Such agents include, but are not limited to: antibiotics, including cephalosporins, β-lactams, tetracyclines, vancomycins, sulfas and aminoglycosides; antivirals, including acylovir; and antifungals including clotrimazole.

In a method aspect the present invention provides methods to treat hyperalgesia by applying an amount of a compound or composition to a mammal to ameliorate or eliminate pain. Thus, the method of the present invention comprises a method of treating pain internally or externally present in the mammalian body including: internal injuries, such as those caused by accident or surgical procedures; abnormal functioning of body organs; irritation associated with inflammation following local infection, blisters, boils, or acute skin injuries, such as abrasions, burns, superficial cuts, surgical incisions, toothaches, contusions, irritations, inflammatory skin conditions, including but not limited to poison ivy, and allergic rashes and dermatitis and any condition that yields a hyperalgesic pain state and other such conditions.

Assessment of Anti-hyperalgesic Activity

The pharmacological activity of the compounds of the present invention may be assessed by several art-recognized in vitro and in vivo models. Some of the typical models are described herein.

(a) In vitro Binding Assay (Primary Screen)[14]

The initial test of these compounds is [$^3$H]diprenorphine binding to the cloned human kappa receptor. The compounds that inhibit binding by at least 80% at 1 μM are titrated and K$_i$ values are determined by Cheng-Prusoff transformations of IC$_{50}$ value is the affinity of the inhibitor for the receptor. Compounds are also tested against [$^3$H] U69593 (agonist) binding to this receptor. No compound is known to inhibit only agonist binding or antagonist binding. However, such a compound may have a unique pharmacological profile as a result of its specificity for one region of the receptor.

Initial specificity is determined by testing compounds in [$^3$H]diprenorphine binding to cloned human mu and delta receptors at 10 μM and titrating those compounds that inhibit binding by at least 80%. Compounds that do not have $K_i$, values at least 100-fold higher against mu and delta receptors may be more likely to have additional side effects and are not pursued to enable further evaluation of specific compounds.

Ref.

(14) Raynor et al., M. Pharmacol. 45: 330-334 (1994)

(b) Inflamed Knee Joint Hyperalgesia Model and Blood Pressure Response to Compression of the Inflamed Knee Joint Inflammation in a joint is often associated with hyperalgesia [pain during normal flexion and extension and during the application of gentle innocuous pressure] and/or persistent pain [resting pain; Schaible et at., (1993) *Pain* 55: 5-54]. During the course of knee joint inflammation, a cascade of events occurs, which includes: (i) synthesis and release of inflammatory mediators in the joint, (ii) release of neuropeptides from afferent fibers in the joint cavity, and (iii) increased primary afferent outflow from group II, III and IV sensory fibers [Schaible et al., (1993) *Pain* 55: 5.54]. An important result of this cascade is that there is an augmentation in the response of small, lightly myelinated and unmyelinated afferents to low intensity stimuli. In this manner, the peripheral nerve innervating inflamed tissue can evoke an exaggerated behavioral response to otherwise innocuous stimuli, i.e., a state of hyperalgesia. Thus, inflammation of the knee joint will result in increased spontaneous afferent activity, the appearance of an exaggerated discharge with joint flexion and extension [Schaible et al., (1995) *J. Neurophysiol.* 54: 1109-1122] and signs of a pain-associated autonomic reaction [Sata et al. (1984) *Neurosci. Lett.* 52: 55-601.

Injection of a mixture of kaolin and carrageenan into the knee joint induces an experimental arthritis. As exemplified below, this treatment was characterized by a reliable increase in joint volume and circumference. In the unanesthetized rat, these joint changes were accompanied by a tendency to avoid weight bearing, suggesting an ongoing pain state. According to electrophysiological studies, in the course of the development of this acute arthritis, C and Aδ units normally responding only to extreme joint distortion become activated by slight movement [Schaible et al. (1985) *J. Neurophysiol.* M: 1109-1122]. Spinal neurons with knee joint receptive fields in the deep dorsal horn of the spinal cord show clear development of hyperexcitability with the acute inflammation in the joint [Neugebauer et al., (1993) *J. Neurosci.* 70: 1365-1377]. This sensitization of group III and IV fibers was observed within 2-3 hours after injection of kaolin and carrageenan into the knee joint, a time course that closely matches the time course of the development of hyperalgesia in the rat knee joint compression model. These observations indicate that spinal cord neurons and joint primary afferent fibers become sensitized and may underlie hyperalgesia observed in this arthritic state. Such afferent input may drive autonomic responses that are typically associated with the processing of input from afferents typically activated by stimuli generated by the local inflammatory state. In addition to the above-mentioned inflamed knee joint mechanism, the blood pressure (BP) changes might also be evoked reflexively by afferent neural activity from receptors located in the skeletal muscle [Williamson et al., (1994) *J. Physiol* 475: 351-357]. This response is dependent on the changes i n intramuscular pressure and the quality of muscle mass compressed. This particular mechanical reflex, however, appears to operate independently of the pain response and appears to play a minor role in the exemplified experiments, as inflation of the cuff on the left normal knee joint had no effect upon BP. In any case, it is possible that overflow of the carrageenan from the joint capsule may serve to render surrounding tissue inflamed as well. Sensitization of C and A units was observed in the rat gastrocnemius muscle by infiltration with carrageenan [Handwerker et al. (1991) *Pain and Inflammation, Proceeding of the VIth World Congress on Pain*. Bond et al eds., Elsevier Science Publishers BV, pp. 59-70]. Based on these considerations, it appears that compression of the inflamed knee joint yields a noxious stimulus and this in turn activates a sympathetic response resulting in an increase in BP.

Local inflammation of the knee results in a state where otherwise innocuous stimuli results in a prominent autonomic response, including increased blood pressure (BP) and heart rate [see, e.g., Sata et al. (1984) *Neurosci. Lett.* 55-60]. Alternatively, neural outflow from the inflamed knee is recorded [see, e.g. Neugebauer et al (1993). *J. Neurosci.* 70: 1365-1377]. An in vitro test that measures spontaneous discharge in injured skin by topical application may also be used. [see, e.g., Andreev er al. (1994) *Neurosci.* 58: 793-798].

(c) In Vivo Evaluation of Formalin-induced Nociception

Administration of formalin into the paw results in a localized inflammation and a pain response that is moderate in intensity and continuous in duration. Unlike many other assays of nociception, the formalin assay measures tonic pain that is a result of tissue injury, and therefore is a model which is more relevant to clinical pain states in humans [see Tjolsen et al., (1991) *Pain* 51: 5-17]. In the rat the response to formalin-induced pain consists of spontaneous flinching behavior, characterized by paw lifting and paw shaking, and a rapid vibration of the paw after drawing it under the body. The flinching response can be reliably quantitated and exhibits two peaks of activity which are indicative of acute and tonic pain [Wheeler-Aceto and Cowan (1991) *Psychopharmacology* 104: 35-44]. The early or acute phase lasts from 0-5 min post-formalin and is followed by a quiescent period lasting approximately 15 min. The tonic phase occurs from 20-35 min following formalin injection and is the interval where the number of flinching responses in maximal. This model has been characterized in several species [Tjolsen et al., (1992) *Pain* 51: 5-17] and is sensitive to the analgesic effects of opiates administered by a variety of routes, including local administration directly into the paw. In addition, the test is particularly sensitive to the effects of κ agonists [Wheeler-Aceto and Cowan (1991) *Psychopharmacology* 104: 35-44].

Inflammation is induced by subcutaneous injection of 50 μl of a 5% formalin solution into the dorsal surface of the right hind paw of male Sprague-Dawley rats weighing 70-90 g. Injections of drug are given into the dorsal surface of the paw prior to formalin injection, and flinching behavior is quantitated by counting the number of responses that occur during the tonic phase of pain, lasting from 20-35 min after formalin injection. Results are expressed as the mean percent antagonism of formalin-induced flinching calculated for individual drug-treated, formalin-injected rats using the following formula:

$$\frac{(\text{mean formalin response} - \text{mean saline response}) - \text{individual response} \times 100}{\text{mean formalin response} - \text{saline response}}$$

The mean formalin response is the mean behavioral score of vehicle-treated and formalin-injected rats. The mean saline response is the pooled behavioral score from rats injected with 50 ml of saline into the paw.

(d) Randall-Selitto Test

Numerous variations and exemplifications of this assay are known to those of skill in this are [see, Randall et al. (1957) *Arch. Int. Pharmacodyn.* 111: 409-419; see, also, e.g., U.S. Pat. No. 5,434,292, U.S. Pat. No. 5,369,131, U.S. Pat. No. 5,345,943, U.S. Pat. No. 5,242,944 and U.S. Pat. No. 5,109135.

The pain threshold is measured in this method as the amount of pressure in g required to induce a flight reaction (struggle) when applied to the foot of an experimental animal exhibiting hyperalgesia, typically an inflamed paw, compared to a control, such as the same or equivalent animal in the absence of the inflammation, and/or in the absence of a test compound. Incremental pressure is applied to the paw with a wedge-shaped blunt piston onto the dorsal surface of the hind paw by means of a paw pressure analgesia meter. The pressure required to elicit paw withdrawal, the paw pressure threshold (PPT), is determined. Stein and coworkers [Stein et al. (1988) *Pharmacol. Biochem. Behav.* 31: 445-45 1; Stein et al (1989) *J. Pharmacol. Exp. Ther* 2448: 1269-1275] have developed a model of peripheral inflammation and hyperalgesia in rats, which supports the role of opiates in mediating peripheral analgesia. In this protocol, modified Freund's adjuvant is used as the inflammatory stimulus, and the paw pressure test is used to assess the response of the rat to a painful pressure stimulus. The model is sensitive to opiate agonist of the μ, δ and κ subtypes, which produce analgesia upon administration [Antonijevic et al., (1995) *J. Neurosci.* 15: 165-172; Stein et a. (1988) *Neurosci. Lett.* 84: 225-228; Stein et al., (1989) *J. Pharmacol. Exp. Ther.* 248: 1269-1275]. Histological verification of opiate receptor localization and density have confirmed that peripheral opiate receptors are accessible on primary afferent nerve fibers and are upregulated following inflammation [Hassan et al. (1993) *Neuroscience* 55. 185-193; Przewlocki et al., (1992) *Neuroscience* 48: 491-500].

Experiments are conducted in rats weighing 150-250 g at the time of inoculation. Modified Freund's complete adjuvant (FCA) is used as the inflammatory stimulus. Rats are administered an i.pl. injection of the FCA suspension into the right hind foot. Hyperalgesia and antinociception are evaluated using the paw pressure test. The rat is gently restrained and incremental pressure is applied to the paw with a wedge-shaped blunt piston onto the dorsal surface of the hind paw by means of a paw pressure analgesia meter. The pressure required to elicit paw withdrawal, the paw pressure threshold (PPT), is determined. A cutoff pressure of 250 g is used to avoid undue stress and pain to the animal. Baseline responding is established by determining the average of three consecutive trials separated by 10 sec. The same procedure is conducted on the contralateral side and the sequence of sides is alternated between animals to control for order effects. Typically injections are not made in the contralateral (noninflamed) paw; however, in selected cases drugs may be administered to the contralateral paw to evaluate the potential for drug effects in the absence of inflammation.

Analgesic activity is determined by expressing the increase in PPT resulting from the effect of the drug as a percentage of basal preinjection thresholds.

Hyperalgesia can also be produced by inflammatory stimuli such as yeast or carrageenan, endogenous inflammatory mediators such as bradykinin or prostaglandins, or other types of chemical irritants [see Hargreaves and Joris (1993) *APS Journal* 2:51-59].

(e) Acetic Acid-induced Writhing

This test identifies novel agents which exhibit peripheral analgesic activity against visceral or chemical pain [see Barber and Gottschlich (1986) *Med. Res. Rev.* 12: 525-562; Ramabadran and Bansinath (1986) *Pharm. Res.* 3: 263-270]. Injection of acetic acid into the peritoneal cavity is used as the noxious stimulus, and the number of writhing responses that occur in response to acetic acid are counted in order to quantify the response to pain. Compounds which possess analgesic activity reduce the number of writhing responses that occur. Opiate agonists of the μ and κ subtype exhibit analgesic activity in this model [Barber and Gottschlich (1986) *Med. Res. Rev.* 12: 525-562; Millan (1990) *Trends Pharmacol. Sci.* 11: 70-76]. Novel compounds which demonstrate potency and efficacy in this assay are potential drugs for the treatment of various pathological conditions involving peripheral pain. The writhing assay is adapted from the procedure originally described by Taber et al., [(1969) *J. Pharmacol. Exp. Ther.* 169: 29-38], using male CF-1 mice weighing 20-25 g. Animals are treated with various doses of drugs prior to the administration of an i.p. injection of 0.6% acetic acid solution. Mice are then placed into observation chambers and number of writhing responses, as defined by a full hindlimb extension and retraction, are recorded.

The mean number of writhing responses is calculated for vehicle-treated control mice, and the percent inhibition (% I) of writhing is calculated for each mouse that is treated with drug using the following formula:

$$\% I = \frac{100 \times (\text{mean control writhing responses} - \text{individual test responses})}{\text{mean control writhing responses}}$$

(f) Hyperalgesia Induced by Tape Stripping

The objective of this assay is to identify novel agents which exhibit peripherally—mediated analgesia in circumstances, such as burns and abrasions, which lead to hyperalgesia. In such injuries, the loss of the stratum corneum is followed by an inflammatory response (erythema) and a painful response to otherwise innocuous stimuli. Removal of the stratum corneum by repeated application and removal of cellophane tape, termed tape stripping, has been shown to be a simplified model of these injuries, which share characteristics of first degree burns [see Flynn (1985) *Percutaneous Absorption*, R. L. Bronaugh and H. I. Maibach, eds., Marcel Dekker Inc., pp. 18-42]. This method of barrier disruption avoids the application of potentially toxic chemicals and permits evaluation of peripheral analgesics following topical administration because tape stripping removes the barrier to effective topical therapy (the stratum corneum) while simultaneously resulting in inflammation and hyperalgesia. Tape stripping has been validated in humans as a model for the testing of topical agents [Pershing et al. (1994) *Antimicrob. Agents Chemother.* 38: 90-95; Roy and Flynn (1990) *Pharm. Res.* 7:842-847].

Experiments are conducted in male Sprague-Dawley rats weighing 250-300 g at the time of treatment. After anesthesia of the rat with ketamine-xylamine, a 1-3 cm² patch of rat skin is treated by repeated application and removal of tape. This procedure results in removal of the stratum corneum as determined by a glistening appearance of the skin. The tape stripped skin is evaluated for a visible erythema and for sensitivity of contact by heat or pressure stimuli using a focused beam of light, by testing in the paw pressure apparatus or by touch with von Frey hairs. The diameter of the von Frey hairs will be selected based on a diameter which causes no response in control rats but has a readily detectable response in treated rats.

Typically analgesics will be formulated in a suitable topical medium and applied to the 20 treated skin. Some rats will receive only the topical medium without analgesic to control for an effect of the topical medium alone. The presence of analgesia is determined by the latency to respond to the heat stimulus or by response to touch or pressure.

Pharmacological activities of compounds of the present invention are shown in Tables I, II, III and IV in which $K_i$: nM ($^3$H-diprenorphine and $^3$H-U-69,593) show in vitro binding assay results as described in "(a) In vitro binding assay (Primary Screen); and $A_{50}$ (µg) values; i/paw show in vivio formalin-induced nociception results as described in "(c) In vivo evaluation of formalin-induced nociception".

| Compounds | R | Ar | $K_i$, nM $^3$H-Diprenorphine | $^3$H-U-69,593 | Late Phase Formalin $A_{50}$ (µg); i.paw |
|---|---|---|---|---|---|
| GR 89696 (R) | $CO_2CH_3$ | 3,4-$Cl_2$ | 0.095, 0.10 | 1.6, 1.5 | 0.42(0.29-0.57) |
| ADL-01-0143-6 (R-1) | Bn | 3,4-$Cl_2$ | 57, 38 | 9.3, 4.1 | 53% @ 300 |
| ADL-01-0047-9 (R-2) | H | 3,4-$Cl_2$ | 14, 17 | 1.5, 1.3 | 57% @ 300 |
| ADL-01-0039-6 (R-3a) | $SO_2CH_3$ | 3,4-$Cl_2$ | 0.2, 1.3 | 0.19, 0.5 | 14(5.6-29) |
| ADL-01-0040-4 (R-3b) | $CH_2CO_2$t-Bu | 3,4-$Cl_2$ | 30% @ 1 uM | 75% @ 1 uM | Not tested |
| ADL-01-0042-0 (R-3c) | $CH_2CO_2H$ | 3,4-$Cl_2$ | 62% @ 1 uM | 23, 21 | 26% @ 300 |
| ADL-01-0048-7 (R-3d) | BnO$_2$C–CH$_2$–CH(NHBoc)–C(=O)– | 3,4-$Cl_2$ | 36% @ 1 uM | 379, 249 | Not tested. |
| ADL-01-0041-2 (R-3e) | HO$_2$C–CH$_2$–CH(NH$_2$)–C(=O)– | 3,4-$Cl_2$ | 39% @ 1 uM | 37, 28 | 22% A @ 300 |
| ADL-01-0148-5 (R-3f) | $COCH_3$ | 3,4-$Cl_2$ | 4.2, 1.4 | 0.11, 0.14 | 95% @ 300 |
| ADL-01-0149-3 (R-3g) | $PO(OEt)_2$ | 3,4-$Cl_2$ | 99, 33 | 1.3, 1.4 | 54% @ 300 |
| ADL-01-0150-1 (R-3h) | $COCF_3$ | 3,4-$Cl_2$ | 6.9, 1.8 | 0.26, 0.16 | 94% @ 300 |
| ADL-01-0151-9 (R-3i) | $CONH_2$ | 3,4-$Cl_2$ | 56, 29 | 2.9 | 68% @ 300 |
| ADL-01-0156-8 (R-3j) | CHO | 3,4-$Cl_2$ | 7.8, 6.6 | 0.55 | 65% @ 300 |
| ADL-01-0165-9 (R-3l) | $SO_2$-Tol | 3,4-$Cl_2$ | 199, 42 | 5.7, 6.6 | 24% @ 300 |
| ADL-01-0135-2 (R,S-8a) | $SO_2CH_3$ | 3,4-$Cl_2$ | 5.4, 4.0 | 0.37, 0.65 | 96% @ 300 |
| ADL-01-0117-0 (R,S-8b) | $SO_2CH_3$ | p-$SO_2CH_3$ | 41% @ 1 uM | 20.31 | Not tested. |
| ADL-01-0119-6 (R,S-8c) | $SO_2CH_3$ | o-$NO_2$ | 15% @ 1 uM | 51% @ 1 uM | Not tested. |
| ADL-01-0120-4 (R,S-8d) | $SO_2CH_3$ | p-$CF_3$ | 16, 17 | 1.3, 1.9 | 97% @ 300 |
| ADL-01-0134-5 (R,S-8e) | $SO_2CH_3$ | 3-indole | 74% @ 1 µM | 5.3, 3.2 | 716% @ 300 |
| ADL-01-0092-5 (R,S-9a) | $CO_2CH_3$ | p-$SO_2CH_3$ | 11, 9.8 | 0.37, 0.42 | 46% @ 300 |
| ADL-01-0094-1 (R,S-9b) | $CO_2CH_3$ | p-$CF_3$ | 0.49, 0.56 | 0.076, 0.13 | 98% @ 300 |
| ADL-01-0095-8 (R,S-9c) | $CO_2CH_3$ | 3-indole | 3.0, 2.5 | 0.27, 0.40 | 95% @ 300 |
| ADL-01-0096-6 (R,S-9d) | $CO_2CH_3$ | o-$NO_2$ | 37, 24 | 0.74, 0.73 | 93% @ 300 |
| ADL-01-0097-4 (R,S-9e) | $CO_2CH_3$ | o-$OCH_3$ | 7.3, 5.1 | 0.46, 1.3 | 98% @ 300 |
| ADL-01-0098-2 (R,S-9f) | $CO_2CH_3$ | o-$NH_2$ | 4.6, 3.2 | 0.67, 0.41 | 97% @ 300 |

-continued

| Compounds | R | Ar | K$_i$, nM $^3$H-Diprenorphine | K$_i$, nM $^3$H-U-69,593 | Late Phase Formalin A$_{50}$ (µg); i.paw |
|---|---|---|---|---|---|
| ADL-01-0144-4 (R,S-10a) | COCH$_3$ | p-SO$_2$CH$_3$ | 27% @ 1 µM | 2.3, 8, 16 | 6% @ 300 |
| ADL-01-0145-1 (R,S-10b) | COCH$_3$ | p-CF$_3$ | 26, 24 | 2.0, 1.3 | 89% @ 300 |
| ADL-01-0157-6 (R,S-10c) | COCH$_3$ | o-CF$_3$ | 45% @ 1 µM | 16, 15 | Not tested. |
| ADL-01-0158-4 (R,S-10d) | COCH$_3$ | m-NO$_2$ | 14, 6.8 | 0.72, 1.2 | Not tested. |
| ADL-01-0163-4 (R,S-10e) | COCH$_3$ | o-NO$_2$ | 54, 89 | 24, 25 | Not tested. |
| ADL-01-0159-2 (R,S-10f) | COCH$_3$ | p-NO$_2$ | 52, 32 | 24, 4.8 | Not tested. |
| ADL-01-0093-3 (R,S-11) | Bn | p-CF$_3$ | 2.2, 2.4 | 0.39, 0.57 | 92% @ 300 |

TABLE II

Compounds of Formula II

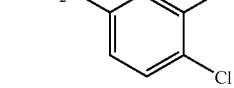

| Compounds | R, n | R' | K$_i$ (nM) κ [$^3$H] Diprenorphin | K$_i$ (nM) κ [$^3$H]U69,593 | Late Phase Formalin A$_{50}$ (µg) i.paw |
|---|---|---|---|---|---|
| ADL-01-0017-2 | 7-OCH$_3$, n = 1 | 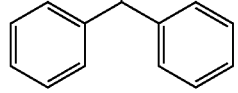 | 9.3, 2.9, 2 | 0.8 | 44% @ 300 |
| ADL-01-0020-6 | 7-OCH$_3$, n = 1 | 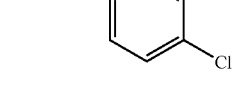 | 154, 131 | 16.23 | 124 |
| ADL-01-0018-0 | 7-OH, n = 1 | 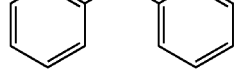 | 0.3, 0.5, 1 | 0.00, 0.3 | 7 |
| ADL-01-0021-4 | 7-OH, n = 1 | 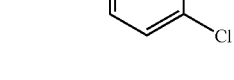 | 482, 616 | 618, 246 | Not tested. |
| ADL-01-0019-8 | 7-OCH$_2$CO$_2$H, n = 1 |  | 40, 40 | 7, 7 | 39% @ 300 |

TABLE II-continued
Compounds of Formula II
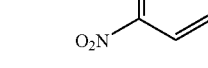
| Compounds | R, n | R' | $K_i$ (nM) κ [$^3$H] Diprenorphin | $K_i$ (nM) κ [$^3$H]U69,593 | Late Phase Formalin $A_{50}$ (μg) i.paw |
|---|---|---|---|---|---|
| ADL-01-0029-7 | 7-NO$_2$, n = 1 | 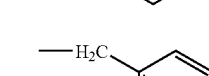 | 2.9, 2.6 | 0.8, 0.8 | 65 |
| ADL-01-0034-7 | 7-NO$_2$, n = 1 | 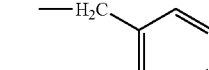 | 57% @ 1 μM | 12.8 | 40% @ 300 |
| ADL-01-0031-3 | 7-NO$_2$, n = 1 |  | 34, 22, 34 | 1.2, 0.2 | 891 |
| ADL-01-0032-1 | 7-NH$_2$, n = 1 | 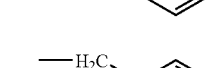 | 1, 3.5 | 0.2, 0.5 | 19 |
| ADL-01-0052-9 | 7-N(CH$_2$CO$_2$Et)$_2$, n = 1 | 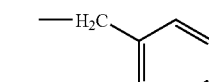 | 4.6, 4.5 | 0.9, 0.47 | 37% @ 300 |
| ADL-01-0037-0 | 7-N(CH$_2$CO$_2$tBu)$_2$, n = 1 |  | 2.8, 12 | 2, 3.7 | 155 |
| ADL-01-0044-6 | 7-N(CH$_2$CO$_2$H)$_2$, n = 1 |  | 5.2, 0.65, 5.5 | 0.8, 0.56 | 232 |
| ADL-01-0070-1 | 7-NH(CH$_2$)$_2$PO$_3$Et$_2$, n = 1 |  | 8.2, 4.2 | 1.9, 2.4 | 75% @ 300 |
| ADL-01-0053-7 | 7-NHPO$_3$Et$_2$, n = 1 |  | 3.5, 1.2 | 1, 0.3 | 34 |
| ADL-01-0090-9 | 7-SO$_2$NCH$_3$Bn, n = 1 6-OMe |  | 48, 89 | 8.0, 6.5 | Not tested. |

TABLE II-continued

Compounds of Formula II

| Compounds | R, n | R' | $K_i$ (nM) κ [$^3$H] Diprenorphin | $K_i$ (nM) κ [$^3$H]U69,593 | Late Phase Formalin $A_{50}$ (μg) i.paw |
|---|---|---|---|---|---|
| ADL-01-0099-0 | 7-SO$_2$NCH$_3$Bn, n = 1 | —H$_2$C—(3,4-diCl-phenyl) | 170, 260 | 45, 35 | Not tested. |
| ADL-01-0051-1 | —H, n = 2 | —H$_2$C—(3,4-diCl-phenyl) | 8.9, 7.9 | 4.4, 1.28 | 37% @ 300 |
| ADL-01-0107-1 | R = H, n = 0 | —H$_2$C—(3,4-diCl-phenyl) | 12, 9.5 | 0.63, 2.0 | 80% @ 300 |
| ADL-01-0109-7 | R = H, n = 0 | —H$_2$C—(4-SO$_2$CH$_3$-phenyl) | 46% @ 1 μM | 11, 29 | Not tested. |
| ADL-01-0108-9 | R = H, n = 0 | —CH(Ph)$_2$ | 29% @ 1 μM | 35, 146 | Not tested. |
| ADL-01-0104-8 | R = H, n = 0 | —H$_2$C—(2-NO$_2$-4,5-diCl-phenyl) | 4.5, 1.5 | 0.74, 0.56 | Not tested. |
| ADL-01-0106-3 | R = H, n = 0 | —H$_2$C—(2-NO$_2$-4-CF$_3$-phenyl) | 75% @ 1 μM | 7.3, 9 | Not tested. |
| ADL-01-0105-5 (±)-Niravoline | R = H, n = 0 | —H$_2$C—(3-NO$_2$-phenyl) | 13, 9.6 | 0.83, 1.8 | 41 |

TABLE III

Compounds of Formula III

| Compounds | X | R | R' | $K_i$ (nM) κ [$^3$H]Diprenorphine | $K_i$ (nM) κ [$^3$H]U69,593 | Late Phase Formalin $A_{50}$ (μg) 1.paw |
|---|---|---|---|---|---|---|
| ADL-01-0004-0 | —H | —NO$_2$ (3-5% p-NO$_2$) | —H$_2$C-(3,4-dichlorophenyl) | 0.8, 0.5 | 0.3, 0.2 | 16 |
| ADL-01-0030-5 | —H | —H | —H$_2$C-(2-nitrophenyl) | 2.9, 9.0 | 0.7, 1.0 | 29 |
| ADL-01-0055-2- | OH | R = H | —H$_2$C-(2-nitrophenyl) | 0.27, 0.95 | 0.08, 0.09 | 15 |
| ADL-01-0033-9 | —H | —H | —H$_2$C-(2-nitro-4,5-dichlorophenyl) | 0.2, 0.2 | 0.1, 0.1 | 5.3 |
| ADL-01-0056-0- | OH | R = H | —H$_2$C-(2-nitro-4,5-dichlorophenyl) | 0.08, 0.1 | 0.06, 0.08 | 27 mg 0.18 mg/kg (sc) |
| ADL-01-0062-8 | —H | —H | —H$_2$C-(2-nitro-4-trifluoromethylphenyl) | 0.064, 0.1, 0.4 | 0.13, 0.13 | 27 |
| ADL-01-0067-7- | OH | R = H | —H$_2$C-(2-nitro-4-trifluoromethylphenyl) | 0.21, 0.1 | 0.11, 0.11 | 97% @ 300 |
| ADL-01-0084-2 | —H | —H | —H$_2$C-(3-nitrophenyl) | 0.38, 0.18 | 0.1, 0.06 | 95% A @ 300 |
| ADL-01-0079-2 | —H | —H | —H$_2$C-(4-nitrophenyl) | 24% @ 1 μM | 1.2, 1.5 | Not tested. |
| ADL-01-0115-4 | —H | —NO$_2$ | —H$_2$C-(2-nitrophenyl) | 35, 128 | 3.2, 1.4 | Not tested. |

TABLE III-continued

Compounds of Formula III

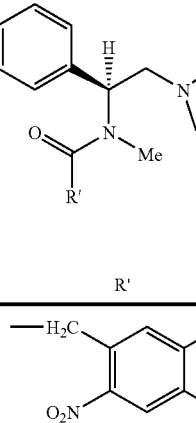

| Compounds | X | R | R' | $K_i$ (nM) κ [³H]Diprenorphine | $K_i$ (nM) κ [³H]U69,593 | Late Phase Formalin $A_{50}$ (μg) 1.paw |
|---|---|---|---|---|---|---|
| ADL-01-0128-7 | —H | —NO₂ | —H₂C-(2-NO₂, 4,5-Cl₂-phenyl) | 0.28, 0.31 | 0.08, 0.06 | Not tested. |
| ADL-01-0129-5 | —H | —NO₂ | —H₂C-(4-SO₂CH₃-phenyl) | 40, 22 | 1.9, 1.1 | Not tested. |
| ADL-01-0132-9 | —H | —NO₂ | —H₂C-(4-NH₂-phenyl) | 76% @ 1 μM | 6.2, 6.5 | Not tested. |
| ADL-01-0133-7 | —H | —NO₂ | —H₂C-(4-N(SO₂Me)₂-phenyl) | 25% @ 1 μM | 79% @ 1 μM | Not tested. |
| ADL-01-0138-6 | —H | —NO₂ | —H₂C-(4-NHBoc-phenyl) | 19% @ 1 μM | 114, 222 | Not tested. |
| ADL-01-0005-7 | —H | 2,3-Br₂ 4-NH₂ | —H₂C-(3,4-Cl₂-phenyl) | 9.4 | 2.3, 6.2 | 306 |
| ADL-01-0007-3 | —H | —NH₂ | —H₂C-(3,4-Cl₂-phenyl) | 0.20, 0.00 | 0.08, 0.02, 0.2 | 0.4 |
| ADL-01-0024-8 | —H | —H | —H₂C-(2-NH₂-phenyl) | 8.6, 7.7 | 15.14 | 65 |
| ADL-01-0089-1 | —H | —H | —H₂C-(3-NH₂-phenyl) | 13 | 0.85 | 58% @ 300 |
| ADL-01-0103-0 | —H | —H | —H₂C-(4-NH₂-phenyl) | 22 | 1.8 | 52% @ 300 |

TABLE III-continued

Compounds of Formula III

| Compounds | X | R | R' | $K_I$ (nM) κ [$^3$H]Diprenorphine | $K_I$ (nM) κ [$^3$H]U69,593 | Late Phase Formalin $A_{50}$ (μg) 1.paw |
|---|---|---|---|---|---|---|
| ADL-01-0035-4 | —H | —H | —H$_2$C—(2,4-diCl, 5-NH$_2$ phenyl) | 0.10 | 0.055 | 7 |
| ADL-01-0068-5 | —H | —H | —H$_2$C—(3-NH$_2$, 5-CF$_3$ phenyl) | 0.09 | 0.10 | 0.02 mg/kg (s.c.) 98% @ 300 |
| ADL-01-0076-8- | OH | R = H | —H$_2$C—(3-NH$_2$, 5-CF$_3$ phenyl) | 0.18 | 0.12 | 0.02 mg/kg (s.c.) 98% @ 300 |
| ADL-01-0113-9 | —H | —NH$_2$ | —H$_2$C—(2-NH$_2$ phenyl) | 20 | 2.6 | 81% @ 300 |
| ADL-01-0059-0- (EMD 60400) | OH | R = H | —H$_2$C—(2-NH$_2$ phenyl) | 0.8 | 0.175 | 33 |
| ADL-01-0136-0 | —H | —NH$_2$ | —H$_2$C—(4-N(SO$_2$Me)$_2$ phenyl) | 61% @ 1 μM | 43 | Not tested. |
| ADL-01-0008-1 | —H | —NH-a-D-Asp | —H$_2$C—(3,4-diCl phenyl) | 3.65 | 1.05 | 72 |
| ADL-01-0009-9 | —H | —NH-a-L-Asp | —H$_2$C—(3,4-diCl phenyl) | 1.9 | 0.5 | 9.1 |
| ADL-01-0010-7 | —H | —NH-a-L-(Asp)$_2$ | —H$_2$C—(3,4-diCl phenyl) | 2.0 | 0.67 | 14 |
| ADL-01-0006-5 | —H | —NH-b-L-Asp | —H$_2$C—(3,4-diCl phenyl) | 2.3 | 0.7 | 47 |

TABLE III-continued
Compounds of Formula III
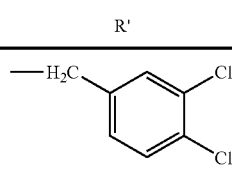
| Compounds | X | R | R' | $K_i$ (nM) κ [$^3$H]Diprenorphine | $K_i$ (nM) κ [$^3$H]U69,593 | Late Phase Formalin $A_{50}$ (μg) 1.paw |
|---|---|---|---|---|---|---|
| ADL-03-1066 | —H | —NH-g-D-Glu | 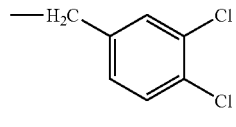 | | | 62 |
| ADL-01-0011-5 | —H—N | (SO$_2$Me)$_2$ | 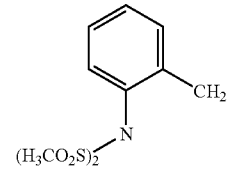 | 6.45 | 1.2 | 58 |
| ADL-01-0060-2 | —H | —H | 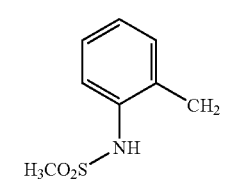 | 57% @ 1 mM | 6.4, 8.9 | 17 |
| ADL-01-0075-0 | —H | —H | 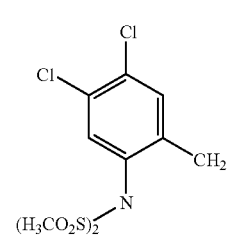 | 54, 40 | 6.8, 3.5 | 8.8 mg/kg (s.c.) 80% @ 300 |
| ADL-01-0050-3 | —H | —H | 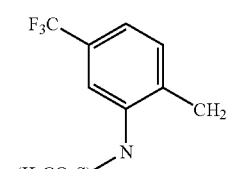 | 0.38, 0.45 | 0.01, 0.09 | 28 |
| ADL-01-0069-3 | —H | —H | 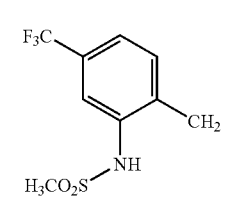 | 0.83, 0.49 | 0.29, 0.43 | Not tested. |
| ADL-01-0077-6 | —H | —H |  | 2.2, 3.8 | 0.64, 0.38 | Not tested. |

TABLE III-continued

Compounds of Formula III

| Compounds | X | R | R' | $K_i$ (nM) κ [$^3$H]Diprenorphine | $K_i$ (nM) κ [$^3$H]U69,593 | Late Phase Formalin $A_{50}$ (μg) l.paw |
|---|---|---|---|---|---|---|
| ADL-01-0112-1 | —H | —H | (H$_3$CO$_2$S)$_2$—N—C$_6$H$_4$—CH$_2$ (3-position) | 63% at 1 mM | 10.8 | 91% @ 300 |
| ADL-01-0127-9 | —H | —H | (SO$_2$CH$_3$)$_2$N—C$_6$H$_4$—CH$_2$ (4-position) | 198 | 32 | Not tested. |
| ADL-01-0126-1 | —H—N | (SO$_2$Me)$_2$ | —H$_2$C—C$_6$H$_4$—N(SO$_2$Me)$_2$ (2-position) | 7% @ 1 mM | 58% @ 1 mM | Not tested. |
| ADL-01-0124-6 | —H | —NHPO$_3$Et$_2$ | —H$_2$C—C$_6$H$_4$—NHPO$_3$Et$_2$ (2-position) | 33 | 48 | Not tested. |
| ADL-01-0139-4 | —H | —NHPO$_3$Et$_2$ | —H$_2$C—C$_6$H$_4$—N(SO$_2$Me)$_2$ (4-position) | 56% @ 1 mM | 76 | Not tested. |
| ADL-01-0063-6- (EMD 61753) | OH | R = H | CH(CH$_3$)(C$_6$H$_5$)$_2$ (diphenylethyl) | 0.52 | 0.34 | 11 mg/kg (s.c.) |
| ADL-01-0023-0 | —H | —H | dibenzyl (diphenylmethane) | 25, 18 | 4.8, 3.0 | 67 |
| ADL-01-0027-1 | —H | —H | diphenylamino | 55, 42, 60 | 7.7, 15 | 174 |

·HCl

TABLE III-continued

Compounds of Formula III

| Compounds | X | R | R' | $K_i$ (nM) κ [$^3$H]Diprenorphine | $K_i$ (nM) κ [$^3$H]U69,593 | Late Phase Formalin $A_{50}$ (µg) 1.paw |
|---|---|---|---|---|---|---|
| ADL-01-0036-2 | —H | —H | H$_3$CO$_2$S—C$_6$H$_4$—CH$_2$— | 0.2, 0.17 | 0.21, 1.7 | 27 |
| ADL-01-0064-4- | OH | R = H | —H$_2$C—C$_6$H$_4$—SO$_2$Me | 0.23 | 0.16 | Not tested. |
| ADL-01-0049-5 | —H | —H | 2-OCH$_3$-C$_6$H$_4$-CH$_2$— | 5.4, 3.7 | 0.36, 0.39 | 39 |
| ADL-01-0061-0 | —H | —H | 2-OH-C$_6$H$_4$-CH$_2$— | 0.43, 0.88 | 0.33, 0.38 | 29 |
| ADL-01-0054-5 | —H | —H | (1H-indol-3-yl)methyl | 0.94, 0.28 | 0.5, 0.07, 0.06 | 13 |
| ADL-01-0058-6 | —H | —H | 4-F$_3$C-C$_6$H$_4$-CH$_2$— | 0.12, 0.013 | 0.050, 0.060 | 0.009 mg/kg (s.c.) 92% @ 300 |
| ADL-01-0111-3 | —H | —H | 3-F$_3$C-C$_6$H$_4$-CH$_2$— | 0.30 | 0.12 | 97% @ 300 |
| ADL-01-0123-8 | —H | —H | 2-CF$_3$-C$_6$H$_4$-CH$_2$— | 1.3 | 0.18 | 98% @ 300 |
| ADL-01-0085-9 | —H | —H | (pyridin-2-yl)methyl | 22, 13 | 3.3, 1.3 | 90% @ 300 |

TABLE III-continued
Compounds of Formula III
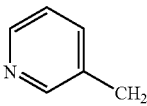
| Compounds | X | R | R' | $K_I$ (nM) κ [$^3$H]Diprenorphine | $K_I$ (nM) κ [$^3$H]U69,593 | Late Phase Formalin $A_{50}$ (μg) 1.paw |
|---|---|---|---|---|---|---|
| ADL-01-0100-6 | —H | —H | 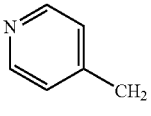 | 65% @ 1 mM | 98% @ 1 mM | 43% @ 300 |
| ADL-01-0122-0 | —H | —H | 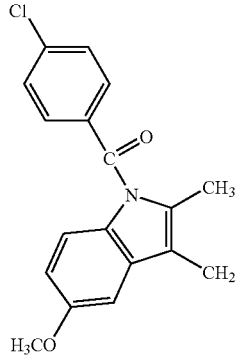 | 52 | 4.8 | 51% @ 300 |
| ADL-01-0078-4 | —H | —H | 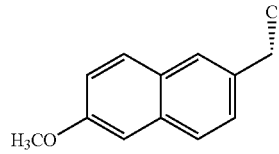 | 5.4, 4.9 | 2.2, 1.2 | Not tested. |
| ADL-01-0110-5 | —H | —H | 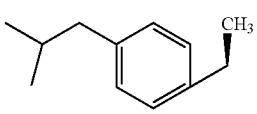 | 75% at 1 mM | 9.0 | 32% @ 300 |
| ADL-01-0125-3 | —H | —H | 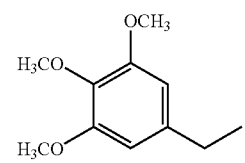 | 19 | 2.2 | 40% @ 300 |
| ADL-01-0146-9 | —H | —H | 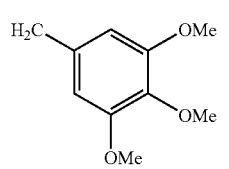 | 100% @ 1 mM | 91% @ 1 mM | 94% @ 300 |
| ADL-01-0140-2- | OH | R = H |  | 1.06 | 0.36 | 89% @ 300 |

TABLE IV

Compounds of Formula IV

| Compounds | R | $K_i$ (nM) diprenorphine | $K_i$ (nM) U-69593 | Late Phase Formalin $A_{50}$ (µg) i.paw |
|---|---|---|---|---|
| U-50488 | 2,4-dichlorobenzyl (H₂C–C₆H₃(Cl)₂) | 4.3 | 0.6 | 91 |
| ADL-01-0012-3 (5a) | 2-NO₂-benzyl | 596 | 100 | Not tested. |
| ADL-01-0014-9 (5b) | 2-NH₂-benzyl | 1031 | 433 | Not tested. |
| ADL-01-0015-6 (5c) | 2-NO₂-4,5-dichlorobenzyl | 6.7 | 1.4 | 40 |
| ADL-01-0016-4 (5d) | 2-NH₂-4,5-dichlorobenzyl | 10.6 | 1.7 | 47 |
| ADL-01-0025-5 (5e) | 2-NHSO₂CH₃-benzyl | 3185 | 675 | Not tested. |
| ADL-01-0028-9 (5f) | 2-NHCH₂CO₂H-benzyl | 14% @ 1 µM | 866 | Not tested. |
| ADL-01-0066-9 (5g) | 4-CF₃-benzyl | 77% @ 1 µM | 3.75 | 59% @ 300 |

TABLE IV-continued

Compounds of Formula IV (±) [structure: N-methyl, N-COR substituted cyclohexane with pyrrolidine] 5a-t

| Compounds | R | $K_i$ (nM) diprenorphine | $K_i$ (nM) U-69593 | Late Phase Formalin $A_{50}$ (μg) i.paw |
|---|---|---|---|---|
| ADL-01-0065-1 (5h) | 2-CH₂-, 3-NO₂, 5-CF₃ phenyl | 59% @ 1 μM | 13.4 | 58% @ 300 |
| ADL-01-0080-0 (5i) | 2-CH₂-, 3-NH₂, 5-CF₃ phenyl | 43% @ 1 μM | 5.4 | 73% @ 300 |
| ADL-01-0118-8 (5j) | 2-CH₂-, 3-N(SO₂CH₃)₂, 5-CF₃ phenyl | 13% @ 1 μM | 48% @ 1 μM | Not tested. |
| ADL-01-0137-8 (5k) | 2-CH₂-, 3-NHSO₂CH₃, 5-CF₃ phenyl | 16% @ 1 μM | 216.0 | Not tested. |
| ADL-01-0130-3 (5l) | 2-CH₂-, 3-NHCH₂CO₂H, 5-CF₃ phenyl | 43.5 | 2.35 | 80% @ 300 |
| ADL-01-0083-4 (5m) | 3-CH₂-, 3'-CF₃ phenyl | 192.5 | 11.25 | 80% @ 300 |
| ADL-01-0087-5 (5n) | 3-CH₂-, 5-CF₃, 3-NO₂ phenyl | 61% @ 1 μM | 10.85 | 70% @ 300 |
| ADL-01-0088-3 (5o) | 2-CH₂-, 3-NO₂, 2'-CF₃ phenyl | 5.65 | 1.4 | 86% @ 300 |

TABLE IV-continued

Compounds of Formula IV

| Compounds | R | $K_1$ (nM) diprenorphine | $K_1$ (nM) U-69593 | Late Phase Formalin $A_{50}$ (μg) i.paw |
|---|---|---|---|---|
| ADL-01-0114-7 (5p) | 2-CF₃-benzyl | 53% @ 1 μM | 25.0 | Not tested. |
| ADL-01-0116-2 (5q) | 3-CF₃-4-NO₂-benzyl | 77% @ 1 μM | 6.4 | Not tested. |
| ADL-01-0142-8 (5r) | 3-CF₃-4-NH₂-benzyl | 50% @ 1 μM | 21.0 | Not tested. |
| ADL-01-0013-1 (5s) | diphenylmethyl | 1171 | 330 | Not tested. |
| ADL-01-0071-9 (5t) | 4-SO₂CH₃-benzyl | 40% @ 1 μM | 96 | 46% @ 300 |

Assessment and Testing of Anti-pruritic Activity

The formulations of the present invention for anti-pruritic activity were tested as follows.

Testing for Anti-Pruritic Activity

Testing was performed in a mouse scratch model under blind conditions

Groups of 8-10 male Swiss albino mice (Hilltop Lab Animals, Inc., Scottsdale, Pa.), weighing 2.5-2.6 g, were used in the testing. They were housed under controlled temperature of 23-25° C. Food and water were freely available. Before the experiments, the mice were weighed, put into individual boxes and allowed to acclimate for 30 min.

Materials

Vehicle used to dissolve the test compounds: 20% v/v cremaphor EL.

To induce scratching Compound 48/80 (Sigma, St. Louis, USA) was used which has been shown to produce an itch sensation in humans (Armstrong et al., *J. Physiol.*, 120: 326, (1953).

The compounds to be tested for anti-pruritic activity were dissolved in the vehicle of 20% v/v cremaphor EL.

Method

100 μl of the vehicle (3-5 doses, n=8-10) was injected s.c. into the back of the neck of mice 20 min before challenging them with 100 μl of Compound 48/80 (2 mg/ml; 50 μg) injected s.c. into the back of the neck. One minute later the mice were observed for 30 min. and the number of hindleg scratching movements directed to the neck was counted.

The vehicle-injected mice scratched 79±16 times in the 30 min after the standard challenge with Compound 48/80.

To each mouse of a group of 8-10 mice previously subjected to the standard challenge, various doses of the compounds to be tested for anti-pruritic activity were administered s.c. into the back of the neck. One minute later the mice were observed for 30 min and the number of hindleg scratching movements directed to the neck was counted.

For each group of 8-10 mice, the mean values for scratching were normalized to relative % antagonism of scratching and then plotted vs. dose of test compounds. Interval estimates of mean $A_{50}$ were determined by nonlinear regression analysis (Kaleidagraph) and mean % inhibition of scratching was calculated.

Compounds tested have shown dose-dependent anti-pruritic activity in the range of from about 15 to 95% based on doses of from about 0.05 to 10.0 mg/kg, s.c.

FORMULATIONS OF THE PRESENT INVENTION

Effective concentrations of one or more of the compounds of the present invention or pharmaceutically acceptable derivatives thereof are mixed with a suitable pharmaceutical carrier or vehicle for systemic, topical or local administration. Compounds are included in an amount effective for reducing the hyperalgesic state or other symptoms for which treatment is contemplated. The concentration of active compound in the composition will depend on absorption, inactivation, excretion rates of the active compound, the dosage schedule, and amount administered as well as other factors known to those of skill in the art. For topical and local administration, the dosages are higher, typically at least about 5 to 10 fold, than the amount delivered when administered systemically or orally.

The compounds of the present invention possess analgesic activity and can be used for the relief of pain without loss of consciousness. For example, compounds can be used to treat muscle spasm, arthritis and other musculoskeletal conditions, e.g., bursitis, relieve mild to moderate postoperative and postpartum pain, dysmenorrhea and pain of traumatic origin. Additionally, the compounds of the present invention can be administered for the treatment of severe pain, e.g., pain associated with adenocarcinoma, amputation of a limb, and third degree burns over a major portion of the body in animals and humans.

Selected compounds of the present invention have activity as narcotic antagonists. They can be used to counteract or prevent excessive central nervous system depression and respiratory depression resulting from the administration of morphine or other morphine-like drugs, e.g., hydromorphone, oxymorphone, methadone and meperidine. The compounds are also capable of inducing an abstinence syndrome in narcotic addicted subjects, i.e., induce withdrawal effects for diagnostic purposes.

The dosage of the compound of Formulas I, II, III, IV and V for analgesic purposes is from about 0.001 to about 20 mg/kg body weight of the patient. The compounds of Formulas I, II, III, IV and V are conveniently prepared in 5, 10, 25, 50, 75, 100 and 200 mg dosage units for administration for 1 to 4 times a day. Preferred unit dosages are from 0.05 to 10 mg/kg body weight of the patient.

The compounds are administered orally, parentally, rectally and topically.

Pharmaceutical carriers or vehicles suitable for administration of the compounds and for the methods provided herein include any such carriers known to those skilled in the art to be suitable for the particular mode of administration. In addition, the compounds may be formulated as the sole pharmaceutically active ingredient in the composition or may be combined with other active ingredients.

a) Systemic Formulations

The formulations of the present invention are provided for administration to humans and animals in unit dosage forms, such as tablets, capsules, pills, powders, granules, sterile parenteral solutions or suspensions, and oral solutions or suspensions, and oil-water emulsions containing suitable quantities of a compound of Formulas I, II, III, IV and V or pharmacologically acceptable salts thereof.

Pharmaceutical dosage unit forms are prepared to provide from about 0.05 mg to about 500 mg and preferably from about 1.0 to about 200 mg of the essential active ingredient or a combination of essential ingredients per dosage unit form.

Oral pharmaceutical dosage forms are either solid or liquid. The solid dosage forms are tablets, capsules, granules, and bulk powders. Types of oral tablets include compressed, chewable lozenges and tablets which may be enteric-coated, sugar coated or film-coated. Capsules may be hard or soft gelatin capsules, while granules and powders may be provided in non-effervescent or effervescent form with the combination of other ingredients known to those skilled in the art.

Pharmaceutically acceptable carriers utilized in tablets are binders, lubricants, diluents, disintegrating agents, coloring agents, flavoring agents, and wetting agents. Enteric-coated tablets, due to their enteric-coating, resist the action of stomach acid and dissolve or disintegrate in the neutral or alkaline intestines. Sugar-coated tablets are compressed tablets to which different layers of pharmaceutically acceptable substances have been applied. Film-coated tablets are compressed tablets which have been coated with water soluble polymers. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar-coated, multiple compressed and chewable tablets. Flavoring and sweetening agents are especially useful in the formation of chewable tablets and lozenges.

Examples of binders include glucose solution, acacia mucilage, gelatin solution, sucrose and starch paste. Lubricants include talc, starch, magnesium of calcium stearate, lycopodium and stearic acid. Diluents include, for example, lactose, sucrose, starch, kaolin, salt, mannitol and dicalcium phosphate. Disintegrating agents include corn starch, potato starch, bentonite, methylcellulose, agar and carboxymethylcellulose. Coloring agents include, for example, any of the approved certified water soluble FD and C dyes, mixtures thereof, and water insoluble FD and D dyes suspended on alumina hydrate. Sweetening agents include sucrose, lactose, mannitol and artificial sweetening agents such as sodium cyclamate and saccharin, and any number of spray dried flavors. Flavoring agents include natural flavors extracted from plants such as fruits and synthetic blends of compounds which produce a pleasant sensation. Wetting agents include propylene glycol monostearate, sorbitan monooleate, diethylene glycol monolaurate and polyoxyethylene laural ether. Enteric-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substance used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Diluents include lactose and sucrose. Sweetening agents include sucrose, syrups, glycerin and artificial sweetening agents such as sodium cyclamate and saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants and fruits, and synthetic blends of compounds which produce a pleasant taste sensation.

Parenteral administration of the formulations of the present invention includes intravenous, subcutaneous and intramuscular administrations.

Preparations for parenteral administration include sterile solutions ready for injection, sterile dry soluble products ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylceluose, hydroxypopyl methylcellulose and polyvinylpyrrolidone. Emulsifying agents include Polysorbatye 80 (Tween 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, wight and condition of the patient or animal as is known in the art.

The unit-dose parenteral preparations are packaged in an ampoule or a syringe with a needle.

All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Pharmaceutical dosage forms for rectal administration are rectal suppositories, capsules and tablets for systemic effect.

Rectal suppositories as used herein mean solid bodies for insertion into the rectum which melt or soften at body temperature releasing one or more pharmacologically or therapeutically active ingredients.

Pharmaceutically acceptable substances utilized in rectal suppositories are bases or vehicles and agents to raise the melting point.

Examples of bases include cocoa butter (theobroma oil), glycerin-gelatin, corbowax, (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm.

Tablets and capsules for rectal administration are manufactured using the same pharmaceutically acceptable substance and by the same methods as for formulations for oral administration.

The pharmaceutically and therapeutically active compounds of Formulas I, II, III and IV are administered orally, parenterally or rectally in unit-dosage forms or multiple-dosage forms. Unit-dose forms as used herein refers to physically discrete units suitable for human and animal subjects and packaged individually as is know in the art. Each unit-dose contains a predetermined quantity of the therapeutically active compound sufficient to produce the desired therapeutic effect in association with the required pharmaceutical carrier, vehicle or diluent. Examples of unit-dose forms include ampoules and syringes, individually packaged tablet or capsule. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Compounds of the present invention in formulations may be included with other active compounds to obtain desired combinations of properties. Other active compounds with known pharmacological properties include analgesics such as aspirin, phenacetin acetaminophen, propoxyphene, pentazocine, codeine, meperidine, oxycodone, mefenemic acid, and ibuprofen; muscle relaxants such as methocarbamol, orphenadrine, carisoprodol, meprobamate, chlorphenesin carbamate, diazepam, chlordiazepoxide and chlorzoxazone;

analeptics such as caffeine, methylphenidate and pentylenetetrazol; corticosteroids such as methylprednisolone, prednisone, prednisolone and dexamethasone; antihistamines such as chlorpheniramine, cyproheptadine, promethazine and pyrilamine.

b) Local and Topical Formulations

Typically a therapeutically effective dosage is formulated to contain a concentration of at least about 0.1% w/w up to about 50% w/w or more, preferably more than 1% w/w of the active compound to the treated tissue. The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the hyperalgesic or other condition and may be empirically determined.

Compounds are typically included at concentrations 0.001% w/w or greater than 1% w/w up to 50% w/w or higher. The concentration is generally greater than the concentration for systemic administration of the compound. Preferable concentrations are in the range of 0.01% w/w to about 25% w/w, more preferably 1% w/w to 25% w/w, yet more preferably greater than about 1% w/w to about 10% w/w, and most preferably greater than 1% w/w up to about 5% w/w. Aqueous suspensions and formulations contain 1% w/w or more.

The resulting mixture may be a solution, suspension, emulsion or the like and are formulated as creams, gels, ointments, emulsions, solutions, elixirs, lotions, suspensions, tinctures, pastes, foams, aerosols, irrigations, sprays, suppositories, bandages, or any other formulations suitable for topical or local administration.

The route of administration herein is topical or local administration, and compositions are formulated in a manner suitable for each route of administration. Preferred modes of administration include topical application to the skin, eyes or mucosa, and local application to the joints, such as by intra-articular injection. Thus, typical vehicles are those suitable for pharmaceutical or cosmetic application to body surfaces or for local injection.

Pharmaceutical and cosmetic carriers or vehicles suitable for administration of the compounds provided herein include any such carriers known to those skilled in the art to be suitable for the particular mode of administration. In addition, the compounds may be formulated as the sole pharmaceutically active ingredient in the composition or may be combined with other active ingredients. The active compound is included in the carrier in an amount sufficient to exert a therapeutically useful effect in the absence of serious toxic effects on the treated individual. The effective concentration may be determined empirically by testing the compounds using in vitro and in vivo systems, including the animal models described herein.

For topical administration, the compounds may be formulated in compositions in the form of gels, creams, lotions, solids, solutions or suspensions, or aerosols. Compositions for treating human skin are formulated for topical application with an anti-hyperalgesic effective amount of one or more of the compounds selected as described herein, in an effective concentration range [by weight], between about 0.1% and 80%, preferably 0.1 to 50%, more preferably greater than about 1% up to about 50% or more in a cream, ointment, lotion, gel, solution or solid base or vehicle known in the art to be non-toxic and dermatologically acceptable or suitable for application to the mucosa. Aqueous suspensions are preferably formulated at concentrations greater than about 1% w/w, more preferably 2% w/w.

To formulate a composition, the weight fraction of compound is dissolved, suspended, dispersed or otherwise mixed in a selected vehicle at an effective concentration such that the hyperalgesic condition is relieved or ameliorated. Generally, emollient or lubricating vehicles that help hydrate the skin are more preferred than volatile vehicles, such as ethanol, that dry the skin. Examples of suitable bases or vehicles for preparing compositions for use with human skin are petrolatum, petrolatum plus volatile silicones, lanolin, cold cream [USP], and hydrophilic ointment [USP].

The choice of an acceptable vehicle is largely determined by the mode of application and tissue to be treated. Suitable pharmaceutically and dermatologically acceptable vehicles for topical application include those suited for use and include lotions, creams, solution, gels, tapes and the like. Generally, the vehicle is either organic in nature or an aqueous emulsion and capable of having the selected compound or compounds, which may be micronized, dispersed, suspended or dissolved therein. The vehicle may include pharmaceutically-acceptable emollients, skin penetration enhancers, coloring agents, fragrances, emulsifiers, thickening agents, and solvents.

For local internal administration, such as intra-articular administration, the compounds are preferably formulated as a suspension in an aqueous-based medium, such as isotonically buffered saline or are combined with a biocompatible support or bioadhesive intended for internal administration.

Lotions

The lotions contain an effective concentration of one or more of the compounds. The effective concentration is preferably effective to deliver am anti-hyperalgesic amount, typically at a concentration of between about 0.1-50% w/w or more of one or more of the compounds provided herein. The lotions also contain from 1% to 50% w/w, preferably from 3% to 15% w/w of an emollient and the balance water, a suitable buffer, a C2 or C3 alcohol, or a mixture of water of the buffer and the alcohol. Any emollients known to those of skill in the art as suitable for application to human skin may be used. These include, but are not limited to, the following:

(a) Hydrocarbon oils and waxes, including mineral oil, petrolatum, paraffin, ceresin, ozokerite, microcrystalline wax, polyethylene, and perhydrosqualene.

(b) Silicone oils, including dimethylpolysioxanes, methylphenylpolysioxanes, water-soluble and alcohol-soluble silicone-glycol copolymers.

(c) Triglyceride fats and oils, including those derived from vegetable, animal and marine sources. Examples include, but are not limited to, castor oil, safflower oil, cotton seed oil, corn oil, olive oil, cod liver oil, almond oil, avocado oil, palm oil, sesame oil and soybean oil.

(d) Acetoglyceride esters, such as acetylated monoglycerides.

(e) Ethoxylated glycerides, such as ethoxylated glyceryl monostearate.

(f) Alkyl esters of fatty acids having 10 to 20 carbon atoms. Methyl, isopropyl and butyl esters of fatty acids are useful herein. Examples include, but are not limited to, hexyl laurate, isohexyl laurate, isohexyl palmitate, isopropyl palmitate, isopropyl myristate, decyl oleate, isodecyl oleate, hexadecyl stearate, decyl stearate, isopropyl isostearate diisopropyl adipate, diisohexyl adipate, dihexyldecyl adipate, diisopropyl sebacate, lauryl lactate, myristyl lactate, and cetyl lactate.

(g) Alkenyl esters of fatty acids having 10 to 20 carbon atoms. Examples thereof include, but are not limited to, oleyl myristate, oleyl stearate, and oleyl oleate.

(h) Fatty acids having 9 to 22 carbon atoms. Suitable examples include, but are not limited to pelargonic, lauric, myristic, palmitic, stearic, isostearic, hydroxystearic, oleic, linoleic, ricinoleic, arachidonic, behenic, and erucic acids.

(i) Fatty alcohols having 10 to 20 carbon atoms, such as but not limited to, lauryl, myristyl, cetyl, hexadecyl, stearyl, isostearyl, hydroxystearyl, oleyl, ricinoleyl, behenyl, erucyl, and 2-octyl dodecyl alcohols.

(j) Fatty alcohol ethers, including, but not limited to, ethoxylated fatty alcohols of 10 to 20 carbon atoms, such as, but are not limited to, the lauryl cetyl, stearyl, isostearyl, oleyl, and cholesterol alcohols having attached thereto from 1 to 50 ethylene oxide groups or 1 to 50 propylene oxide groups or mixtures thereof.

(k) Ether-esters, such as fatty acid esters of ethoxylated fatty alcohols.

(l) Lanolin and derivatives, including but not limited to, lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated hydrogenated lanolin, ethoxylated sorbitol lanolin, and liquid and semisolid lanolin absorption bases.

(m) Polyhydric alcohols and polyether derivatives, including, but not limited to, propylene glycol, dipropylene glycol, polypropylene glycol [M.W. 2000-4000], polyoxyethylene polyoxypropylene glycols, polyoxypropylene polyoxyethylene glycols, glycerol, ethoxylated glycerol, propoxylated glycerol, sorbitol, ethoxylated sorbitol, hydroxypropyl sorbitol, polyethylene glycol [M.W. 200-6000], methoxy polyethylene glycols 350, 550, 750, 2000, 5000, poly)ethylene oxide) homopolymers [M.W. 100,000-5,000,000], polyalkylene glycols and derivatives, hexylene glycol (2-methyl-2,4-pentanediol), 1,3-butylene glycol, 1,2, 6-hexanetriol, ethohexadiol USP (2-ethyl-1,3-hexanediol), $C_{15}$-$C_{18}$ vicinal glycol and polyoxypropylene derivatives of trimethylolpropane.

(n) Polyhydric alcohol esters, including, but not limited to, ethylene glycol mono- and di-fatty acid esters, diethylene glycol mono- and di-fatty acid esters, polyethylene glycol [M.W. 200-6000], mono- and di-fatty esters, propylene glycol mono- and di-fatty acid esters, polypropylene glycol 2000 monooleate, polypropylene glycol 200 monostearate, ethoxylated propylene glycol monostearate, glyceryl mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters.

(o) Wax esters, including, but not limited to, beeswax, spermaceti, myristyl myristate, and stearyl stearate and beeswax derivatives, including, but not limited to, polyoxyethylene sorbitol beeswax, which are reaction products of beeswax with ethoxylated sorbitol of varying ethylene oxide content that form a mixture of ether-esters.

(p) Vegetable waxes, including, but not limited to, carnauba and candelilla waxes.

(q) Phospholipids, such as lecithin and derivatives.

(r) Sterols, including, but not limited to, cholesterol and cholesterol fatty acid esters.

(s) Amides, such as fatty acid amides, ethoxylated fatty acid amides, and solid fatty acid alkanolamides.

The lotions further preferably contain from 1% w/w to 10% w/w, more preferably from 2% w/w to 5% w/w, of an emulsifier. The emulsifiers can be nonionic, anionic or cationic. Examples of satisfactory nonionic emulsifiers include, but are not limited to, fatty alcohols having 10 to 20 carbon atoms, fatty alcohols having 10 to 20 carbon atoms condensed with 2 to 20 moles of ethylene oxide or propylene oxide, alkyl phenols with 6 to 12 carbon atoms in the alkyl chain condensed with 2 to 20 moles of ethylene oxide, mono- and di-fatty acid esters of ethylene oxides, mono- and di-fatty acid esters of ethylene glycol wherein the fatty acid moiety contains from 10 to 20 carbon atoms, diethylene glycol, polyethylene glycols of molecular weight 200 to 6000, propylene glycols of molecular weight 200 to 3000, glycerol, sorbitol, sorbitan, polyoxyethylene sorbitol, polyoxyethylene sorbitan and hydrophilic wax esters. Suitable anionic emulsifiers include, but are not limited to, the fatty acid soaps, e.g., sodium, potassium and triethanolamine soaps, wherein the fatty acid moiety contains from 10 to 20 carbon atoms. Other suitable anionic emulsifiers include, but are not limited to, the alkali metal, ammonium or substituted ammonium alkyl sulfates, alkyl arylsulfonates, and alkyl ethoxy ether sulfonates having 10 to 30 carbon atoms in the alkyl moiety. The alkyl ethoxy ether sulfonates contain form 1 to 50 ethylene oxide units. Among satisfactory cationic emulsifiers are quaternary ammonium, morpholinium and pyridinium compounds. Certain of the emollients described in preceding paragraphs also have emulsifying properties. When a lotion is formulated containing such an emollient, an additional emulsifier is not needed, though it can be included in the composition.

The balance of the lotion is water or a C2 or C3 alcohol, or a mixture of water and the alcohol. The lotions are formulated by simply admixing all of the components together. Preferably, the compound is dissolved, suspended or otherwise uniformly dispersed in the mixture.

Other conventional components of such lotions may be included. One such additive is a thickening agent at a level from 1% to 10% w/w of the composition. Examples of suitable thickening agents include, but are not limited to cross-linked carboxypolymethylene polymers, ethyl celluloses, polyethylene glycols, gum, tragacanth, gum kharaya, xanthan gums and bentonite, hydroxyethyl cellulose, and hydroxypropyl cellulose.

Creams

The creams are formulated to contain concentrations effective to deliver an anti-hyperalgesic effective amount of the compound to the treated tissue, typically at between about 0.1%, preferably at greater than 1% up to and greater than 50%, preferably between about 3% and 50%, more preferably between about 5% and 15% of one or more of the compounds provided herein. The creams also contain from 5% to 50%, preferably from 10% to 25%, of an emollient and the remainder is water or other suitable non-toxic carrier, such as an isotonic buffer. The emollients, as described above for the lotions, can also be used in the cream compositions. The cream may also contain a suitable emulsifier, as described above. The emulsifier is included in the composition at a level from 3% to 50%, preferably from 5% to 20%.

Solutions and Suspensions for Topical and Local Administration

The solutions are formulated to contain an amount of one or more compounds effective to deliver an anti-hyperalgesic amount, typically at a concentration of between about 0.1-50% w/w, preferably at least more than 1% w/w, more preferably more than 2% w/w of one or more of the compounds provided herein. The balance is water, a suitable organic solvent or other suitable solvent or buffer. Suitable organic materials useful as the solvent or a part of a solvent system are as follows: propylene glycol, polyethylene glycol [M.W. 200-600], polypropylene glycol [M.W. 425-2025], glycerine, sorbitol esters, 1,2,6-hexanetriol, ethanol, isopropanol, diethyl tartrate, butanediol and mixtures thereof. Such solvent systems can also contain water.

Solutions or suspensions used for local application can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid [EDTA]; buffers, such as acetates, citrates and phosphates; and agents for the adjustment of tonicity such as sodium chloride or dextrose. Liquid preparations can be enclosed in ampoules, disposable syringes or multiple dose vials made of glass, plastic or other suitable material. Suitable carriers may include physiological saline or phosphate buffered saline [PBS], and the suspensions and solutions may contain thickening and solubilizing agents, such as glucose, polyethylene glycol, and polypropylene glycol and mixtures thereof. Liposomal suspensions, may also be suitable as pharmaceutically acceptable carriers. These may be prepared according to methods known to those skilled in the art.

These compositions that are formulated as solutions or suspensions may be applied to the skin, or may be formulated as an aerosol or foam and applied to the skin as a spray-on. The aerosol compositions typically contain from 25% to 80% w/w, preferably from 30% to 50% w/w, of a suitable propellant. Examples of such propellants are the chlorinated, fluorinated and chlorofluorinated lower molecular weight hydrocarbons. Nitrous oxide, carbon dioxide, butane, and propane are also molecular weight hydrocarbons. Nitrous oxide, carbon dioxide, butane, and propane are also used as propellant gases. These propellants are used as understood in the art in a quantity and under a pressure suitable to expel the contents of the container.

Suitably prepared solutions and suspension may also be topically applied to the eyes and mucosa. Solutions, particularly those intended for ophthalmic use, may be formulated as 0.01%-10% w/w isotonic solutions, pH about 5-7, with appropriate salts, and preferably containing one or more of the compounds herein at a concentration of about 0.1% w/w, preferably greater than 1% w/w, up to 50% w/w or more. Suitable ophthalmic solutions are known [see, e.g., U.S. Pat. No. 5,116,868, which describes typical compositions of ophthalmic irrigation solutions and solutions for topical application]. Such solutions, which have a pH adjusted to about 7.4, contain, for example, 90-100 mM sodium chloride, 4-6 mM dibasic potassium phosphate, 4-6 mM dibasic sodium phosphate, 8-12 mM sodium citrate, 0.5-1.5 mM magnesium chloride, 1.5-2.5 mM calcium chloride, 15-25 mM sodium acetate, 10-20 mM D,L-sodium β-hydroxybutyrate and 5-5.5 mM glucose.

The active compounds of the present invention can also be mixed with other active materials that do not impair the desired action, or with materials that supplement the desired action, including viscoelastic materials, such as hyaluronic acid, which is sold under the trademark HEALON [solution of a high molecular weight (MW of about 3 million) fraction of sodium hyaluronate; manufactured by Pharmacia, Inc., see, e.g., U.S. Pat. Nos. 5,292,362, 5,282,851, 5,273,056, 5,229,127, 4,517,295 and 4,328,803], VISCOAT [fluorine-containing (meth) acrylates, such as, 1H, 2H, 2H-heptadecafluorodecylmethacrylate; see, e.g., U.S. Pat. Nos. 5,278,126, 5,273,751 5,214,080; commercially available from Alcon Surgical, Inc.], ORCOLON [see, e.g., U.S. Pat. No. 5,273,056; commercially available form Optical Radiation Corporation], methylcellulose, methyl hyaluronate, polyacrylamide and polymethacrylamide [see, e.g., U.S. Pat. No. 5,273,751]. The viscoelastic materials are present generally in amounts ranging from about 0.5 to 5.0% w/w, preferably 1 to 3% w/w of the conjugate material and serve to coat and protect the treated tissues. The compositions may also include a dye, such as methylene blue of other inert dye, so that the composition can be seen when injected into the eye or contacted with the surgical site during surgery.

Gels

Gel compositions can be formulated by simply admixing a suitable thickening agent to the previously described solution or suspension composition. Examples of suitable thickening agents have been previously described with respect to the lotions.

The gelled compositions contain an effective amount of one or more of an antihyperalgesic amount, typically at a concentration of between about 0.1-50% w/w or more of one or more of the compounds provided therein; from 5% to 75% w/w, preferably from 10% to 50% w/w, of an organic solvent as previously described; from 0.5% to 20% w/w, preferably from 1% to 10% w/w of the thickening agent; the balance being water or other aqueous carrier.

Solids

Compositions of solid forms may be formulated as stick-type compositions intended for application to the lips or other parts of the body. Such compositions contain an effective amount of one or more of the compounds provided therein. The amount is typically an amount effective to deliver an anti-hyperalgesic amount, typically at a concentration of between about 0.1-50% w/w or more of one or more of the compounds provided herein. The solids also contain from about 40% to 98% w/w, preferably form about 50% to 90% w/w, of the previously described emollients. This composition can further contain from 1% to 20% w/w, preferably from 5% to 15% w/w, of a suitable thickening agent, and, if desired or needed, emulsifiers and water or buffers. Thickening agents previously described with respect to lotions are suitably employed in the composition in solid form.

Other ingredients such as preservatives, including methylparaben or ethyl-paraben, perfumes, dyes or the like, that are known in the art to provide desirable stability, fragrance or color, or other desirable properties, such as shielding from actinic rays from the sun, to compositions for application to the skin may also be employed in a composition for such topical application.

Additional Ingredients

Other active ingredients include, but are not limited to, antibiotics, antivirals, antifungals, anti-inflammatories, including steroidal and non-steroidal anti-inflammatories, anesthetics and mixtures thereof. Such additional ingredients include any of the following:

a. Antibacterial Agents

Aminoglycosides, such as Amikacin, Apramycin, Arbekacin, Bambermycins, Butirosin, Dibekacin, Dihydrostreptomycin, Fortimicin(s), Fradiomycin, Gentamicin, Ispamicin, Kanamycin, Micronomicin, Neomycin, Neomycin Undecylenate, Netilmicin, Paromomycin, Ribostamycin, Sisomicin, Spectinomycin, Streptomycin, Streptonicozid and Tobramycin;

Amphenicols, such as Azidamfenicol, Chloramphenicol, Chloramphenicol Palmirate, Chloramphenicol Pantothenate, Florfenicol, Thiamphenicol;

Ansamycins, such as Rifamide, Rifampin, Rifamycin and Rifaximin;

β-Lactams;

Carbapenems, such as Imipenem;

Cephalosporins, such as 1-Carba (dethia) Cephalosporin, Cefactor, Cefadroxil, Cefamandole, Cefatrizine, Cefazedone, Cefazolin, Cefixime, Cefmenoxime, Cefodizime, Cefonicid, Cefoperazone, Ceforanide, Cefotaxime, Cefotiam, Cefpimizole, Cefpirimide, Cefpodoxime Proxetil, Cefroxadine, Cefsulodin, Ceftazidime, Cefteram, Ceftezole, Ceftibuten, Ceftizoxime, Ceftriaxone, Cefuroxime, Cefuzonam, Cephacetnile Sodium, Cephalexin, Cephaloglycin, Cephaloridine, Cephalosporin, Cephalothin, Cephapirin Sodium, Cephradine and Pivcefalexin;

Cephamycins such as Cefbuperazone, Cefmetazole, Cefminox, Cefetan and Cefoxitin;

Monobactams such as Aztreonam, Carumonam and Tigemonan;

Oxacephems such as Flomoxef and Moxolactam;

Penicillins such as Amidinocillin, Amdinocillin, Pivoxil, Amoxicillin, Ampicillan, Apaldillin, Aspoxidillin, Azidocillan, Azlocillan, Bacampidillin, Benzylpenicillinic Acid, Benzylpenicillin, Carbenidillin, Carfecillin, Carindadillin, Clometocillin, Cloxacillin, Cyclacillin, Dicloxacillin, Diphenidillin, Epicillin, Fenbenidillin, Floxidillin, Hetadillin, Lenampicillin, Metampidillin, Methidillin, Mezlodillin, Nafcillin, Oxacillin, Penamecillin, Penethamate Hydriodide, Penicillin G Benethamine, Penicillin G Benzathine, Penicillin G Benzhydrylamine, Penicillin G Calcium, Penicillin G Hydragamine, Penicillin G Potassium, Penicillin G Procaine, Penicillin N, Penicillin 0, Penicillin V, Penicillin V Benzathine, Penicillin V Hydrabamine, Penimepicycline, Phenethicillin, Piperacillin, Pivapicillin, Propidillin, Quinadillin, Sulbenidillin, Talampicillin, Temocillin and Ticarcillin;

Lincosamides such as Clindamycin and Lincomycin;

Macrolides such as Azithromycin, Carbomycin, Clarithromycin, Erythromycin(s) and Derivatives, Josamycin, Leucomycins, Midecamycins, Miokamycin, Oleandomycin, Primycin, Rokitamycin, Rosaramicin, Roxithromycin, Spiramycin and Troleandomycin;

Polypeptides such as Amphomycin, Bacitracin, Capreomycin, Colistin, Enduracidin, Enviomycin, Fusafungine, Gramicidin(s), Gramicidin S, Mikamycin, Polymyxin, Polymyxin βMethanesulfonic Acid, Pristinamycin, Ristocetin, Teicoplanin, Thiostrepton, Tuberactinomycin, Tyrocidine, Tyrothricin, Vancomycin, Viomycin(s), Virginiamycin and Zinc Bacitracin;

Tetracyclines such as Spicycline, Chlortetracydline, Clomocycline, Demeclocydline, Doxycycline, Guamecydline, Lymecycline, Meclocycline, Methacycline, Minocycline, Oxytetracycline, Penimepicydline, Pipacycline, Rolitetracydline, Sancycline, Senociclin and Tetracycline; and others such as Cycloserine, Mupirocin, Tuberin.

b. Synthetic Antibacterials 2,4-Diaminopyrimidines such as Brodimoprim, Tetroxoprim and Trimethoprim; Nitrofurans such as Furaltadone, Furazolium, Nifuradene, Nifuratel, Nifurfoline, Nifurpirinol, Nifurprazine, Nifurtoinol and Nitrofurantoin;

Quinolones and analogs thereof, such as Amifloxacin, Cinoxacin, Ciprofloxacin, Difloxacin, Enoxacin, Fleroxacin, Flumequine, Lomefloxacin, Mioxacin, Nalidixic Acid, Norfioxacin, Ofloxacin, Oxolinic Acid, Perfioxacin, Pipemnidic Acid, Piromidic Acid, Rosoxacin, Temafloxacin and Tosufloxacin;

Sulfonamides such as Acetyl Sulfamethoxypyrazine, Acetyl Suffisoxazole, Azosulfamide, Benzylsulfamide, Chloramine-β, Chloramine-T, Dichloramine-T, Formosulfathiazole, $N^2$-Formyl-suffisomidine, $N^4$-B-D-Glucosylsulfanilamide, Mafenide, 4'-(Methyl-sulfamoyl)sulfanilanilide, p-Nitrosulfathiazole, Noprylsulfamide, Phthalylsulfacetamide, Phthalylsulfathiazole, Salazosulfadimidine, Succinylsulfathiazole, Sulfabenzamide, Sulfacetamide, Sulfachiorpyridazine, Sulfachrysoidine, Sulfacytine, Sulfadiazine, Sulfadicramide, Sulfadimethoxine, Sulfadoxine, Sulfaethidole, Sulfaguanidine, Sulfaguanol, Sulfalene, Sulfaloxic Acid, Sulfamerazine, Sulfameter, Sulfamethazine, Sulfamethizole, Sulfamethomidine, Sulfamethoxazole, Sulfamethoxypyridazine, Sulfametrole, sulfamidochrysoidine, Sulfamoxole, Sulfanilamide, Sulfanilamidomethanesulfonic Acid Triethanolamine Salt, 4-Sulfanilamidosalicycic Acid, $N^4$-Sulfanilylsulfanilamide, Sulfanilylurea, N-Sulfanilyl-3,4-xylamide, Sulfanitran, Sulfaperine, Sulfaphenazole, Sulfaproxyline, Sulfapyrazine, Sulfapyridine, Sulfasomizole, Sulfasymazine, Sulfathiazole, Sulfathiourea, Sulfatolamide, Sulfisomidine and Sulfisoxazole;

Sulfones, such as Acedapsone, Acediasulfone, Acetosulfone, Dapsone, Diathymosulfone, Glucosulfone, Solasulfone, Succisulfone, Sulfanilic Acid, p-Sulfanilylbenzylamine, p.p'-sulfonyldianihine-N,N' digalactoside, Sulfoxone and Thiazolsulfone;

Others such as Clofoctol, Hexedine, Magainins, Methenamine, Methenamine Anhydromethylene-citrate, Methenamine Hippurate, Methenamine Mandelate, Methenamine Sulfosalicylate, Nitroxoline, Squalamine and Xibornol.

c. Antifungal (antibiotics)

Polyenes such as Amphotericin-B, Candicidin, Dermostatin, Filipin, Fungichromin, Hachimycin, Hamycin, Lucensomycin, Mepartricin, Natamycin, Nystatin, Peciocin, Perimycin; and others, such as Azaserine, Gniseofulvin, Oligomycins, Pyrrolnitrin, Siccanin, Tubercidin and Viridin.

d. Antifungal (Synthetic)

Allylamines such as Naftifine and terbinafine;

Imidazoles such as Bifonazole, Butoconazole, Chlordantoin, Chlormidazole, Cloconazole, Clotrimazole, Econazole, Enilconazole, Finticonazole, Isoconazole, Ketoconazole, Miconazole, Omoconazole, Oxiconazole Nitrate, Sulconazole and Tioconazole;

Triazoles such as Fluconazole, Itraconazole, Terconazole;

Others such as Acrisorcin, Amorolfine, Biphenamine, Bromosalicylchloranihide, Buclosamide, Chiophenesin, Ciclopirox, Cloxyquin, Coparaffinate, Diamthazole, Dihydrochloride, Exalamide, Flucytosine, Halethazole, Hexetidine, Loflucarban, Nifuratel, Potassium Iodide, Propionic Acid, Pyrithione, Salicylanilide, Sulbentine, Tenonitrozole, Tolciclate, Tolindate, Tolnaftate, Tricetin, Ujothion, and Undecylenic Acid.

e. Antiglaucoma Agents

Antiglaucoma agents, such as Dapiprazoke, Dichlorphenamide, Dipivefrin and Piocarpine.

f. Anti-inflammatory Agents

Corticosteroids, aminoarylcarboxylic Acid Derivatives such as Etofenamate, Meclofenamic Acid, Mefanamic Acid. Niflumic Acid;

Arylacetic Acid Derivatives such as Acemetacin, Amfenac, Cinmetacin, Clopirac, Diclofenac, Fenclofenac, Fenclorac, Fenclozic Acid, Fentiazac, Glucametacin, Isozepac, Lonazolac, Metiazinic Acid, Oxametacine, Proglumetacin, Sulindac, Tiaramide and Tolmetin;

Arylbutyric Acid Derivatives such as Butibufen and Fenbufen:

Arylcarboxylic Acids such as Clidanac, Ketorolac and Tinoridine;

Arylpropionic Acid Derivatives such as Bucloxic Acid, Carprofen, Fenoprofen, Flunoxaprofen, Ibuprofen, Ibuproxam, Oxaprozin, Piketoprofen, Pirprofen, Pranoprofen, Protizinic Acid and Tiaprofenic Acid;

Pyrazoles such as Mepirizole;

Pyrazolones such as Clofezone, Feprazone, Mofebutazone, Oxyphenbutazone, Phenylbutazone, Phenyl Pyrazolidininones, Suxibuzone and Thiazolinobutazone;

Salicylic Acid Derivatives such as Bromosaligenin, Fendosal, Glycol Salicylate, Mesalamine, 1-Naphthyl Salicylate, Olsalazine and Sulfasalazine;

Thiazinecarboxamides such as Droxicam, Isoxicam and Piroxicam;

Others such as e-Acetanmidocaproic Acid, S-Adenosylmethionine, 3-Amino-4-hydroxybutynic Acid, Amixetrine, Bendazac, Bucolome, Carbazones, Difenpiramide, Ditazol, Guaiazulene, Heterocycic Aminoalkyl Esters of Mycophenolic Acid and Derivatives, Nabumetone, Nimesulide, Orgotein, Oxaceprol, Oxazole Derivatives, Paranyline, Pifoxinie, 2-substituted-4, 6-di-tertiary-butyl-s-hydroxy-1, 3-pyrimidines, Proquazone and Tenidap.

g. Antiseptics

Guanidines such as Alexidine, Ambazone, Chiorhexidine and Picloxydine;

Halogens/Halogen Compounds such as Bornyl Chloride, Calcium Iodate, Iodine, Iodine Monochloride, Iodine Trichloride, Iodoform, Povidone-Iodine, Sodium Hypochlorite, Sodium Iodate, Syniclosene, Thymol Iodide, Triclocarban, Triclosan and Troclosene Potassium;

Nitrofurans such as Furazolidone, 2-(Methoxymethyl)-5-Nitrofuran, Nidroxyzone, Nifuroxime, Nifurzide and Nitrofurazone;

Phenols such as Acetomeroctol, Chioroxylenol, Hexachlorophene, 1-Naphthyl Salicylate, 2,4,6-Tribromo-m-cresol and 3',4,5-Trichlorosalicylanilide;

Quinolines such as Aminoquinuride, Chloroxine, Chlorquinaldol, Cloxyquin, Ethylhydrocupreine, Halquinol, Hydrastine, 8-Hydroxyquinoline and Sulfate; and others, such as Boric Acid, Chloroazodin, m-Cresyl Acetate, Cupric sulfate and Ichthamniol.

h. Antivirals

Purines/Pyrimidinones, such as 2-Acetyl-Pyridine 5-((2-pynidylamino)thiocarbonyl) Thiocarbonohydrazone, Acyclovir, Dideoxyadenosine, Dideoxycytidine, Dideoxyinosine, Edoxudine, Floxuridine, Ganciclovir, Idoxuridine, MADU, Pyridinone, Trifluridine, Vidrarbine and Zidovudline;

Others such as Acetylleucine Monoethanolamine, Acridinamine, Alkylisooxazoles, Amantadine, Amidinomycin, Cuminaldehyde Thiosemicarbzone, Foscarnet Sodium, Kethoxal, Lysozynie, Methisazone, Moroxydine, Podophyllotoxin, Ribavirin, Rimantadine, Stalhimycin, Statolon, Thymosins, Tromantadine and Xenazoic Acid.

Combinations and Kits

The compounds and compositions containing the compounds may also be coated on bandages, mixed with bioadhesives or included in dressings. Thus, combinations of bandages, bioadhesives, dressings and other such materials and the compositions formulated as described herein are provided. Kits containing these combinations, which may also include compositions containing the above listed agents, are also provided.

Articles of Manufacture

The compounds and compositions provided herein may be packaged as articles of manufacture containing packaging material, one or more of the compounds provided herein, which is effective for ameliorating peripheral hyperalgesia, within the packaging material, and a label that indicates that the compound, N-oxide, acid, salt or other derivative thereof is used for treating hyperalgesic conditions.

Methods of Treatment

Compositions for use with human skin preferably may be applied at least once per day, or if necessary, to achieve the desired result, more often, to the areas of the skin for which treatment is sought. It is understood that the precise treatment regimen depends upon the individual treated and may be ascertained empirically depending upon the formulation, and particularly, the age of the treated individual. Any regimen is acceptable as long as the desired anti-hyperalgesic effects are achieved without substantial deleterious or sustained undesirable side effects.

The methods for treating human skin are practiced by applying to the skin, preferably at least daily, a composition suitable for human skin treatment or treatment of mucosal membranes and other body surface tissues, including the vagina, rectum, mouth, eyes and other such tissues. The compositions may be injected into joints or other inflamed areas.

Compositions may be combined with bandages, bioadhesives and other dressings and applied to the body in combination therewith.

The following examples are included for illustrative purposes only and are not intended to limit the scope of the invention.

EXAMPLE A

| Capsules | |
|---|---|
| Active Compound | 2.5 gm |
| Corn starch | 23.0 gm |
| Lactose | 145.0 gm |

EXAMPLE A-continued

| Capsules | |
|---|---|
| Talc | 15.0 gm |
| Magnesium stearate | 3.0 gm |

The ingredients were mixed and were encapsulated using techniques practiced in the art.

EXAMPLE B

| Tablet | |
|---|---|
| Active Compound | 150 gm |
| Lactose | 125 gm |
| Corn starch | 50 gm |
| Magnesium stearate | 2.0 gm |
| Liquid Petrolatum | 2.0 gm |

The ingredients were mixed, then put through U.S. Standard Screens to produce fine granules. The granules were compressed into tablets, each tablet containing about 150 mg of an active compound of the present invention.

EXAMPLE C

| Syrup | |
|---|---|
| Active Compound | 25 gm |
| Lemon Oil | 2 ml |
| Sucrose | 650 gm |
| Citric Acid | 4 gm |
| Benzoic Acid | 3 gm |
| Tragacanth | 16 gm |
| Deionized water q.s. | 1000 ml |

The ingredients, without the active compound, are dispersed in water to make about 800 to 900 ml of solution. The active compound is then added and the solution is stirred into a syrup. Water is then added to make 1000 ml of the syrup.

EXAMPLE D

| Parenteral Solution | |
|---|---|
| Active Compound | 30 gm |
| Methylparaben | 3 gm |
| Propylparaben | 1 gm |
| Lidocaine | 5 gm |
| Deionized water q.s. | 1000 ml |

The ingredients are dissolved in water to provide a solution followed by sterilization by filtration.

EXAMPLE E

| Rectal Suppository | |
|---|---|
| Active Compound | 80 gm |
| Propylene glycol | 95 gm |
| Polyethylene glycol 4000 | 1800 gm |

The active compound is added to the propylene glycol and milled until a finely divided uniform mixture is formed. The polyethylene glycol 4000 is melted and the propylene glycol dispersion is added with stirring to obtain a suspension. The suspension is poured into molds, allowed to solidify and removed from the molds for packaging.

EXAMPLE F

| Water-washable ointment | |
|---|---|
| Active Compound | 1.4% w/w |
| Lanolin alcohol | 0.15 w/w |
| Emulsifying wax NF | 7.5% w/w |
| PEG-20 glycenides | 5.0% w/w |
| Petrolatum | 86.0% w/w |

The ingredients are melted together and mixed well until the resulting ointment congeals.

EXAMPLE G

| Oil-in-water cream | |
|---|---|
| Active Compound | 10.0% w/w |
| Benzyl alcohol | 4.0% w/w |
| Propylene glycol | 10.0% w/w |
| Polyethylene glycol 400 | 10.0% w/w |
| Petrolatum | 20.0% w/w |
| Stearyl alcohol | 10.0% w/w |
| Poloxamer | 10.0% w/w |
| Water q.s. | 100 |
| Buffer to pH | 7.0% w/w |

In preparing the oil-in-water cream, water, propylene glycol and polyethylene glycol 400 are heated to about 70 to 80° C., followed by adding a mixture of petrolatum, stearyl alcohol and poloxamer and the mixture is stirred until homogeneous. The active compound in benzyl alcohol is added and the mixture is homogenized. The pH is then adjusted with a buffer to about 7.0.

EXAMPLE H

| Aqueous gel | |
|---|---|
| Active Compound | 10.0% w/w |
| Benzyl alcohol | 4.0% w/w |
| Hydroxyethyl cellulose | 3.0% w/w |
| Water q.s. | 100 |
| Buffer to pH | 7.0% w/w |

The aqueous gel is prepared by mixing the active compound, benzyl alcohol and adding the mixture to buffered water. Hydroxyethyl cellulose is then added with stirring until the mixture gels.

Having described the invention with reference to its preferred embodiments, it is to be understood that modifications within the scope of the invention will be apparent to those skilled in the art.

What is claimed is:

1. A compound which is:
2-(4-Methylsulfonylphenyl)-N-methyl-N-{[1S]-1-phenyl-2-[1-(3S)-(3-hydroxy-pyrrolidinyl)]ethyl}acetamide;
or a pharmaceutically acceptable salt thereof.

2. A pharmaceutical composition comprising a compound of claim 1 and a pharmaceutically acceptable carrier.

3. A method of treating hyperalgesia in a patient comprising administering to said patient an effective amount of a compound according to claim 1.

4. A method of treating hyperalgesia in a patient comprising administering to said patient an effective amount of the pharmaceutical composition according to claim 2.

* * * * *